(12) United States Patent
Shelton, IV et al.

(10) Patent No.: US 7,845,537 B2
(45) Date of Patent: Dec. 7, 2010

(54) SURGICAL INSTRUMENT HAVING RECORDING CAPABILITIES

(75) Inventors: Frederick E. Shelton, IV, New Vienna, OH (US); John N. Ouwerkerk, Cinncinnati, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1347 days.

(21) Appl. No.: 11/343,803

(22) Filed: Jan. 31, 2006

(65) Prior Publication Data

US 2007/0175964 A1 Aug. 2, 2007

(51) Int. Cl.
*A61B 17/04* (2006.01)
(52) U.S. Cl. ............... 227/180.1; 227/19; 227/175.1; 227/177.1; 227/179.1
(58) Field of Classification Search ............... 227/180.1, 227/19, 175.1, 177.1, 179.1
See application file for complete search history.

(56) References Cited

U.S. PATENT DOCUMENTS

| | | | |
|---|---|---|---|
| 66,052 A | 6/1867 | Smith | |
| 2,037,727 A | 4/1936 | Chapelle | |
| 2,214,870 A | 9/1940 | West | |
| 2,853,074 A | 9/1958 | Olson | |
| 3,078,465 A | 2/1963 | Bobrov | |
| 3,269,630 A | 8/1966 | Fleischer | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,819,100 A | 6/1974 | Noiles et al. | |
| 3,892,228 A | 7/1975 | Mitsui | |
| 3,894,174 A | 7/1975 | Cartun | |
| 3,940,844 A | 3/1976 | Colby et al. | |
| 4,213,562 A | 7/1980 | Garrett et al. | |
| 4,305,539 A | 12/1981 | Korolkov et al. | |
| 4,331,277 A | 5/1982 | Green | |
| 4,347,450 A | 8/1982 | Colligan | |
| 4,349,028 A | 9/1982 | Green | |

(Continued)

FOREIGN PATENT DOCUMENTS

CA 2458946 A1 3/2003

(Continued)

OTHER PUBLICATIONS

U.S. Appl. No. 11/329,020, "Surgical Instrument Having An Articulating End Effector," by Geoffrey C. Hueil, Joseph C. Hueil, Kenneth E. Hogue, Christoph L. Gillum, and Douglas J. Siebenaler, filed Jan. 10, 2006.

(Continued)

*Primary Examiner*—Brian D Nash

(57) ABSTRACT

A surgical instrument. The surgical instrument has an end effector and a trigger in communication with the end effector. The surgical instrument also has a first sensor and an externally accessible memory device in communication with the first sensor. The first sensor has an output that represents a first condition of either the trigger or the end effector. The memory device is configured to record the output of the first sensor. In various embodiments, memory device may include an output port and/or a removable storage medium.

13 Claims, 51 Drawing Sheets

U.S. PATENT DOCUMENTS

| | | | |
|---|---|---|---|
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,442,964 A | 4/1984 | Becht |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,565,189 A | 1/1986 | Mabuchi |
| 4,566,620 A | 1/1986 | Green et al. |
| 4,573,622 A | 3/1986 | Green et al. |
| 4,580,712 A | 4/1986 | Green |
| 4,591,085 A | 5/1986 | Di Giovanni |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,619,262 A | 10/1986 | Taylor |
| 4,629,107 A | 12/1986 | Fedotov et al. |
| 4,655,222 A | 4/1987 | Florez et al. |
| 4,664,305 A | 5/1987 | Blake, III et al. |
| 4,665,916 A | 5/1987 | Green |
| 4,671,445 A | 6/1987 | Barker et al. |
| 4,709,120 A | 11/1987 | Pearson |
| 4,715,520 A | 12/1987 | Roehr, Jr. et al. |
| 4,728,020 A | 3/1988 | Green et al. |
| 4,728,876 A | 3/1988 | Mongeon et al. |
| 4,729,260 A | 3/1988 | Dudden |
| 4,752,024 A | 6/1988 | Green et al. |
| 4,754,909 A | 7/1988 | Barker et al. |
| 4,767,044 A | 8/1988 | Green |
| 4,790,225 A | 12/1988 | Moody et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 5,027,834 A | 7/1991 | Pruitt |
| 5,031,814 A | 7/1991 | Tompkins et al. |
| 5,040,715 A | 8/1991 | Green et al. |
| 5,061,269 A | 10/1991 | Muller |
| 5,065,929 A | 11/1991 | Schulze et al. |
| 5,071,430 A | 12/1991 | de Salis et al. |
| 5,080,556 A | 1/1992 | Carreno |
| 5,083,695 A | 1/1992 | Foslien et al. |
| 5,084,057 A | 1/1992 | Green et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,158,567 A | 10/1992 | Green |
| 5,171,247 A | 12/1992 | Hughett et al. |
| 5,171,249 A | 12/1992 | Stefanchik et al. |
| 5,188,111 A | 2/1993 | Yates et al. |
| 5,200,280 A | 4/1993 | Karasa |
| 5,207,697 A | 5/1993 | Carusillo et al. |
| 5,211,649 A | 5/1993 | Kohler et al. |
| 5,221,036 A | 6/1993 | Takase |
| 5,222,975 A | 6/1993 | Crainich |
| 5,240,163 A | 8/1993 | Stein et al. |
| 5,246,156 A | 9/1993 | Rothfuss et al. |
| 5,253,793 A | 10/1993 | Green et al. |
| 5,258,009 A | 11/1993 | Conners |
| RE34,519 E | 1/1994 | Fox et al. |
| 5,275,323 A | 1/1994 | Schulze et al. |
| 5,275,608 A | 1/1994 | Forman et al. |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,309,927 A | 5/1994 | Welch |
| 5,318,221 A | 6/1994 | Green et al. |
| 5,330,502 A | 7/1994 | Hassler et al. |
| 5,332,142 A | 7/1994 | Robinson et al. |
| 5,339,799 A | 8/1994 | Kami et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,379,933 A | 1/1995 | Green et al. |
| 5,383,880 A | 1/1995 | Hooven |
| 5,383,881 A | 1/1995 | Green et al. |
| 5,389,098 A | 2/1995 | Tsuruta et al. |
| 5,391,180 A | 2/1995 | Tovey et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,344 A | 4/1995 | Williamson et al. |
| 5,409,498 A | 4/1995 | Braddock et al. |
| 5,413,267 A | 5/1995 | Solyntjes et al. |
| 5,413,268 A | 5/1995 | Green et al. |
| 5,415,335 A | 5/1995 | Knodell, Jr. |
| 5,417,361 A | 5/1995 | Williamson, IV |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,445,304 A | 8/1995 | Plyley et al. |
| 5,447,513 A | 9/1995 | Davison et al. |
| 5,449,365 A | 9/1995 | Green et al. |
| 5,456,401 A | 10/1995 | Green et al. |
| 5,458,579 A | 10/1995 | Chodorow et al. |
| 5,462,215 A | 10/1995 | Viola et al. |
| 5,465,895 A | 11/1995 | Knodel et al. |
| 5,465,896 A | 11/1995 | Allen et al. |
| 5,467,911 A | 11/1995 | Tsuruta et al. |
| 5,470,006 A | 11/1995 | Rodak |
| 5,470,007 A | 11/1995 | Plyley et al. |
| 5,472,132 A | 12/1995 | Savage et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |

| Patent | Date | Inventor |
|---|---|---|
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,518,163 A | 5/1996 | Hooven |
| 5,518,164 A | 5/1996 | Hooven |
| 5,522,817 A | 6/1996 | Sander et al. |
| 5,527,320 A | 6/1996 | Carruthers et al. |
| 5,529,235 A | 6/1996 | Boiarski et al. |
| 5,533,581 A | 7/1996 | Barth et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,628 A | 8/1996 | Cooper et al. |
| 5,553,675 A | 9/1996 | Pitzen et al. |
| 5,553,765 A | 9/1996 | Knodel et al. |
| 5,554,169 A | 9/1996 | Green et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,574,431 A | 11/1996 | McKeown et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,618,303 A | 4/1997 | Marlow et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,700,270 A | 12/1997 | Peyser et al. |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |
| 5,747,953 A | 5/1998 | Philipp |
| 5,749,893 A | 5/1998 | Vidal et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,810,811 A | 9/1998 | Yates et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |

| | | | |
|---|---|---|---|
| 5,823,066 A | 10/1998 | Huitema et al. | |
| 5,826,776 A | 10/1998 | Schulze et al. | |
| 5,829,662 A | 11/1998 | Allen et al. | |
| 5,833,690 A | 11/1998 | Yates et al. | |
| 5,833,695 A | 11/1998 | Yoon | |
| 5,836,503 A | 11/1998 | Ehrenfels et al. | |
| 5,836,960 A | 11/1998 | Kolesa et al. | |
| 5,839,639 A | 11/1998 | Sauer et al. | |
| 5,843,132 A | 12/1998 | Ilvento | |
| 5,855,311 A | 1/1999 | Hamblin et al. | |
| 5,865,361 A | 2/1999 | Milliman et al. | |
| 5,868,760 A | 2/1999 | McGuckin, Jr. | |
| 5,871,135 A | 2/1999 | Williamson, IV et al. | |
| 5,873,885 A | 2/1999 | Weidenbenner | |
| 5,876,401 A | 3/1999 | Schulze et al. | |
| 5,878,937 A | 3/1999 | Green et al. | |
| 5,878,938 A | 3/1999 | Bittner et al. | |
| 5,893,506 A | 4/1999 | Powell | |
| 5,894,979 A | 4/1999 | Powell | |
| 5,897,562 A | 4/1999 | Bolanos et al. | |
| 5,901,895 A | 5/1999 | Heaton et al. | |
| 5,904,693 A | 5/1999 | Dicesare et al. | |
| 5,906,625 A | 5/1999 | Bito et al. | |
| 5,908,427 A | 6/1999 | McKean et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,919,198 A | 7/1999 | Graves, Jr. et al. | |
| 5,931,853 A | 8/1999 | McEwen et al. | |
| 5,938,667 A | 8/1999 | Peyser et al. | |
| 5,941,442 A | 8/1999 | Geiste et al. | |
| 5,948,030 A | 9/1999 | Miller et al. | |
| 5,951,552 A | 9/1999 | Long et al. | |
| 5,951,574 A | 9/1999 | Stefanchik et al. | |
| 5,954,259 A | 9/1999 | Viola et al. | |
| 5,988,479 A | 11/1999 | Palmer | |
| 6,010,054 A | 1/2000 | Johnson et al. | |
| 6,017,356 A | 1/2000 | Frederick et al. | |
| 6,022,352 A | 2/2000 | Vandewalle | |
| 6,024,741 A | 2/2000 | Williamson, IV et al. | |
| 6,024,748 A | 2/2000 | Manzo et al. | |
| 6,032,849 A | 3/2000 | Mastri et al. | |
| 6,045,560 A | 4/2000 | McKean et al. | |
| 6,050,472 A | 4/2000 | Shibata | |
| 6,077,286 A | 6/2000 | Cuschieri et al. | |
| 6,079,606 A | 6/2000 | Milliman et al. | |
| 6,082,577 A | 7/2000 | Coates et al. | |
| 6,083,234 A | 7/2000 | Nicholas et al. | |
| 6,083,242 A | 7/2000 | Cook | |
| 6,086,600 A | 7/2000 | Kortenbach | |
| 6,099,537 A | 8/2000 | Sugai et al. | |
| 6,099,551 A | 8/2000 | Gabbay | |
| 6,102,271 A | 8/2000 | Longo et al. | |
| 6,109,500 A | 8/2000 | Alli et al. | |
| 6,119,913 A | 9/2000 | Adams et al. | |
| H1904 H | 10/2000 | Yates et al. | |
| 6,126,058 A | 10/2000 | Adams et al. | |
| 6,126,670 A | 10/2000 | Walker et al. | |
| 6,131,789 A | 10/2000 | Schulze et al. | |
| 6,155,473 A | 12/2000 | Tompkins et al. | |
| 6,156,056 A | 12/2000 | Kearns et al. | |
| 6,162,208 A | 12/2000 | Hipps | |
| 6,171,330 B1 | 1/2001 | Benchetrit | |
| 6,202,914 B1 | 3/2001 | Geiste et al. | |
| 6,214,028 B1 | 4/2001 | Yoon et al. | |
| 6,223,835 B1 | 5/2001 | Habedank et al. | |
| 6,228,084 B1 | 5/2001 | Kirwan, Jr. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,270,508 B1 | 8/2001 | Klieman et al. | |
| 6,273,897 B1 | 8/2001 | Dalessandro et al. | |
| 6,302,311 B1 | 10/2001 | Adams et al. | |
| 6,309,403 B1 | 10/2001 | Minor et al. | |
| 6,315,184 B1 | 11/2001 | Whitman | |
| 6,320,123 B1 | 11/2001 | Reimers | |
| 6,325,810 B1 | 12/2001 | Hamilton et al. | |
| 6,330,965 B1 | 12/2001 | Milliman et al. | |
| 6,358,224 B1 | 3/2002 | Tims et al. | |
| 6,387,113 B1 | 5/2002 | Hawkins et al. | |
| 6,416,486 B1 | 7/2002 | Wampler | |
| RE37,814 E | 8/2002 | Allgeyer | |
| 6,436,107 B1 | 8/2002 | Wang et al. | |
| 6,436,122 B1 | 8/2002 | Frank et al. | |
| 6,443,973 B1 | 9/2002 | Whitman | |
| 6,471,106 B1 * | 10/2002 | Reining | 227/8 |
| 6,488,197 B1 | 12/2002 | Whitman | |
| 6,491,201 B1 | 12/2002 | Whitman | |
| 6,503,257 B2 | 1/2003 | Grant et al. | |
| 6,505,768 B2 | 1/2003 | Whitman | |
| 6,511,468 B1 | 1/2003 | Cragg et al. | |
| 6,517,565 B1 | 2/2003 | Whitman et al. | |
| 6,522,101 B2 | 2/2003 | Malackowski | |
| 6,550,546 B2 | 4/2003 | Thurler et al. | |
| 6,569,171 B2 | 5/2003 | DeGuillebon et al. | |
| 6,578,751 B2 | 6/2003 | Hartwick | |
| 6,588,643 B2 | 7/2003 | Bolduc et al. | |
| 6,592,597 B2 | 7/2003 | Grant et al. | |
| 6,601,749 B2 | 8/2003 | Sullivan et al. | |
| 6,602,252 B2 | 8/2003 | Mollenauer | |
| 6,616,686 B2 | 9/2003 | Coleman et al. | |
| 6,619,529 B2 | 9/2003 | Green et al. | |
| 6,620,166 B1 | 9/2003 | Wenstrom, Jr. et al. | |
| 6,629,988 B2 | 10/2003 | Weadock | |
| 6,636,412 B2 * | 10/2003 | Smith | 361/232 |
| 6,638,108 B2 | 10/2003 | Tachi | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,681,978 B2 | 1/2004 | Geiste et al. | |
| 6,681,979 B2 | 1/2004 | Whitman | |
| 6,682,528 B2 | 1/2004 | Frazier et al. | |
| 6,695,199 B2 | 2/2004 | Whitman | |
| 6,698,643 B2 | 3/2004 | Whitman | |
| 6,705,503 B1 | 3/2004 | Pedicini et al. | |
| 6,716,232 B1 | 4/2004 | Vidal et al. | |
| 6,716,233 B1 | 4/2004 | Whitman | |
| 6,723,087 B2 | 4/2004 | O'Neill et al. | |
| 6,752,768 B2 | 6/2004 | Burdorff et al. | |
| 6,752,816 B2 | 6/2004 | Culp et al. | |
| 6,755,338 B2 | 6/2004 | Hahnen et al. | |
| 6,773,438 B1 | 8/2004 | Knodel et al. | |
| 6,786,382 B1 | 9/2004 | Hoffman et al. | |
| 6,786,896 B1 | 9/2004 | Madani et al. | |
| 6,793,652 B1 | 9/2004 | Whitman et al. | |
| 6,805,273 B2 | 10/2004 | Bilotti et al. | |
| 6,806,808 B1 | 10/2004 | Watters et al. | |
| 6,814,741 B2 | 11/2004 | Bowman et al. | |
| 6,817,508 B1 | 11/2004 | Racenet et al. | |
| 6,817,509 B2 | 11/2004 | Geiste et al. | |
| 6,821,273 B2 | 11/2004 | Mollenauer | |
| 6,828,902 B2 | 12/2004 | Casden | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,905,497 B2 | 6/2005 | Truckai et al. | |
| 6,945,444 B2 | 9/2005 | Gresham et al. | |

| | | | | | | |
|---|---|---|---|---|---|---|
| 6,953,138 | B1 | 10/2005 | Dworak et al. | 7,431,189 B2 | 10/2008 | Shelton, IV et al. |
| 6,953,139 | B2 | 10/2005 | Milliman et al. | 7,431,730 B2 | 10/2008 | Viola |
| 6,959,852 | B2 | 11/2005 | Shelton, IV et al. | 7,434,715 B2 | 10/2008 | Shelton, IV et al. |
| 6,964,363 | B2 | 11/2005 | Wales et al. | 7,434,717 B2 | 10/2008 | Shelton, IV et al. |
| 6,978,921 | B2 | 12/2005 | Shelton et al. | 7,438,209 B1 | 10/2008 | Hess et al. |
| 6,978,922 | B2 | 12/2005 | Bilotti et al. | 7,441,684 B2 | 10/2008 | Shelton, IV et al. |
| 6,981,628 | B2 | 1/2006 | Wales et al. | 7,441,685 B1 | 10/2008 | Boudreaux |
| 6,981,941 | B2 | 1/2006 | Whitman et al. | 7,448,525 B2 | 11/2008 | Shelton, IV et al. |
| 6,986,451 | B1 | 1/2006 | Mastri et al. | 7,464,847 B2 | 12/2008 | Viola et al. |
| 6,988,649 | B2 | 1/2006 | Shelton, IV et al. | 7,467,740 B2 | 12/2008 | Shelton, IV et al. |
| 6,988,650 | B2 | 1/2006 | Schwemberger et al. | 7,472,815 B2 | 1/2009 | Shelton, IV et al. |
| 7,000,818 | B2 | 2/2006 | Shelton, IV et al. | 7,481,824 B2 | 1/2009 | Boudreaux et al. |
| 7,000,819 | B2 | 2/2006 | Swayze et al. | 7,490,749 B2 | 2/2009 | Schall et al. |
| 7,008,435 | B2 | 3/2006 | Cummins | 7,494,039 B2 | 2/2009 | Racenet et al. |
| 7,032,799 | B2 | 4/2006 | Viola et al. | 7,500,979 B2 | 3/2009 | Hueil et al. |
| 7,036,680 | B1 | 5/2006 | Flannery | 7,506,790 B2 | 3/2009 | Shelton, IV |
| 7,044,352 | B2 | 5/2006 | Shelton, IV et al. | 7,506,791 B2 | 3/2009 | Omaits et al. |
| 7,044,353 | B2 | 5/2006 | Mastri et al. | 7,510,107 B2 | 3/2009 | Timm et al. |
| 7,048,687 | B1 | 5/2006 | Reuss et al. | 7,546,940 B2 | 6/2009 | Milliman et al. |
| 7,055,730 | B2 | 6/2006 | Ehrenfels et al. | 7,552,854 B2 | 6/2009 | Wixey et al. |
| 7,056,330 | B2 | 6/2006 | Gayton | 7,631,793 B2 | 12/2009 | Rethy et al. |
| 7,059,508 | B2 | 6/2006 | Shelton, IV et al. | 7,641,093 B2 | 1/2010 | Doll et al. |
| 7,066,944 | B2 | 6/2006 | Laufer et al. | 7,665,646 B2 | 2/2010 | Prommersberger |
| 7,070,083 | B2 | 7/2006 | Jankowski | 2002/0049454 A1 | 4/2002 | Whitman et al. |
| 7,075,770 | B1 * | 7/2006 | Smith .................. 361/232 | 2002/0117534 A1 | 8/2002 | Green et al. |
| 7,077,856 | B2 | 7/2006 | Whitman | 2002/0134811 A1 * | 9/2002 | Napier et al. ............... 227/131 |
| 7,080,769 | B2 | 7/2006 | Vresh et al. | 2002/0165541 A1 | 11/2002 | Whitman |
| 7,090,673 | B2 | 8/2006 | Dycus et al. | 2003/0105478 A1 | 6/2003 | Whitman et al. |
| 7,090,684 | B2 | 8/2006 | McGuckin, Jr. et al. | 2003/0130677 A1 | 7/2003 | Whitman et al. |
| 7,097,089 | B2 | 8/2006 | Marczyk | 2003/0216778 A1 | 11/2003 | Weadock |
| 7,098,794 | B2 | 8/2006 | Lindsay et al. | 2004/0006372 A1 | 1/2004 | Racenet et al. |
| 7,108,709 | B2 | 9/2006 | Cummins | 2004/0028502 A1 | 2/2004 | Cummins |
| 7,114,642 | B2 | 10/2006 | Whitman | 2004/0034369 A1 | 2/2004 | Sauer et al. |
| 7,118,582 | B1 | 10/2006 | Wang et al. | 2004/0094597 A1 | 5/2004 | Whitman et al. |
| 7,121,446 | B2 | 10/2006 | Arad et al. | 2004/0097987 A1 | 5/2004 | Pugsley et al. |
| 7,122,028 | B2 | 10/2006 | Looper et al. | 2004/0108357 A1 | 6/2004 | Milliman et al. |
| 7,128,253 | B2 | 10/2006 | Mastri et al. | 2004/0111081 A1 | 6/2004 | Whitman et al. |
| 7,128,254 | B2 | 10/2006 | Shelton, IV et al. | 2004/0116952 A1 | 6/2004 | Sakurai et al. |
| 7,140,527 | B2 | 11/2006 | Ehrenfels et al. | 2004/0122471 A1 | 6/2004 | Toby et al. |
| 7,143,924 | B2 | 12/2006 | Scirica et al. | 2004/0164123 A1 | 8/2004 | Racenet et al. |
| 7,143,925 | B2 | 12/2006 | Shelton, IV et al. | 2004/0167572 A1 | 8/2004 | Roth et al. |
| 7,143,926 | B2 | 12/2006 | Shelton, IV et al. | 2004/0173659 A1 | 9/2004 | Green et al. |
| 7,159,750 | B2 | 1/2007 | Racenet et al. | 2004/0222268 A1 | 11/2004 | Bilotti et al. |
| 7,168,604 | B2 | 1/2007 | Milliman et al. | 2004/0230214 A1 | 11/2004 | Donofrio et al. |
| 7,172,104 | B2 | 2/2007 | Scirica et al. | 2004/0232199 A1 | 11/2004 | Shelton, IV et al. |
| 7,188,758 | B2 | 3/2007 | Viola et al. | 2004/0232201 A1 | 11/2004 | Wenchell et al. |
| 7,207,233 | B2 | 4/2007 | Wadge | 2004/0243151 A1 | 12/2004 | Demmy et al. |
| 7,207,471 | B2 | 4/2007 | Heinrich et al. | 2004/0243176 A1 | 12/2004 | Hahnen et al. |
| 7,207,472 | B2 | 4/2007 | Wukusick et al. | 2004/0254608 A1 | 12/2004 | Huitema et al. |
| 7,210,609 | B2 | 5/2007 | Leiboff et al. | 2005/0006431 A1 | 1/2005 | Shelton et al. |
| 7,220,272 | B2 | 5/2007 | Weadock | 2005/0006434 A1 | 1/2005 | Wales et al. |
| 7,225,964 | B2 | 6/2007 | Mastri et al. | 2005/0021026 A1 | 1/2005 | Baily |
| 7,241,288 | B2 | 7/2007 | Braun | 2005/0023324 A1 | 2/2005 | Doll et al. |
| 7,246,734 | B2 | 7/2007 | Shelton, IV | 2005/0033357 A1 | 2/2005 | Braun |
| 7,258,262 | B2 | 8/2007 | Mastri et al. | 2005/0059997 A1 | 3/2005 | Bauman et al. |
| 7,278,563 | B1 | 10/2007 | Green | 2005/0070958 A1 | 3/2005 | Swayze et al. |
| 7,295,907 | B2 | 11/2007 | Lu et al. | 2005/0072827 A1 | 4/2005 | Mollenauer |
| 7,296,724 | B2 | 11/2007 | Green et al. | 2005/0103819 A1 | 5/2005 | Racenet et al. |
| 7,297,149 | B2 | 11/2007 | Vitali et al. | 2005/0107824 A1 | 5/2005 | Hillstead et al. |
| 7,300,450 | B2 | 11/2007 | Vleugels et al. | 2005/0119669 A1 | 6/2005 | Demmy |
| 7,303,106 | B2 | 12/2007 | Milliman et al. | 2005/0125009 A1 | 6/2005 | Perry et al. |
| 7,303,107 | B2 | 12/2007 | Milliman et al. | 2005/0131390 A1 | 6/2005 | Heinrich et al. |
| 7,303,108 | B2 | 12/2007 | Shelton, IV | 2005/0131457 A1 | 6/2005 | Douglas et al. |
| 7,328,829 | B2 | 2/2008 | Arad et al. | 2005/0143759 A1 | 6/2005 | Kelly |
| 7,343,920 | B2 | 3/2008 | Toby et al. | 2005/0165415 A1 | 7/2005 | Wales |
| 7,398,907 | B2 | 7/2008 | Racenet et al. | 2005/0171522 A1 | 8/2005 | Christopherson |
| 7,398,908 | B2 | 7/2008 | Holsten et al. | 2005/0173490 A1 | 8/2005 | Shelton, IV |
| 7,404,508 | B2 | 7/2008 | Smith et al. | 2005/0178813 A1 | 8/2005 | Swayze et al. |
| 7,404,509 | B2 | 7/2008 | Ortiz et al. | 2005/0184121 A1 | 8/2005 | Heinrich |
| 7,407,078 | B2 | 8/2008 | Shelton, IV et al. | 2005/0187576 A1 | 8/2005 | Whitman et al. |
| 7,410,086 | B2 | 8/2008 | Ortiz et al. | 2005/0189397 A1 | 9/2005 | Jankowski |
| 7,422,136 | B1 | 9/2008 | Marczyk | 2005/0192609 A1 | 9/2005 | Whitman et al. |
| 7,424,965 | B2 | 9/2008 | Racenet et al. | 2005/0192628 A1 | 9/2005 | Viola |

| | | | | | |
|---|---|---|---|---|---|
| 2005/0203550 A1 | 9/2005 | Laufer et al. | 2007/0175958 A1 | 8/2007 | Shelton, IV et al. |
| 2005/0216055 A1 | 9/2005 | Scirica et al. | 2007/0175959 A1 | 8/2007 | Shelton, IV et al. |
| 2005/0230453 A1 | 10/2005 | Viola | 2007/0175960 A1 | 8/2007 | Shelton, IV et al. |
| 2005/0240222 A1 | 10/2005 | Shipp | 2007/0175961 A1 | 8/2007 | Shelton, IV et al. |
| 2005/0263562 A1 | 12/2005 | Shelton, IV et al. | 2007/0175962 A1 | 8/2007 | Shelton, IV et al. |
| 2005/0263563 A1 | 12/2005 | Racenet et al. | 2007/0179476 A1 | 8/2007 | Shelton, IV et al. |
| 2005/0274768 A1 | 12/2005 | Cummins et al. | 2007/0181632 A1 | 8/2007 | Milliman |
| 2006/0008787 A1 | 1/2006 | Hayman et al. | 2007/0194079 A1 | 8/2007 | Hueil et al. |
| 2006/0011699 A1 | 1/2006 | Olson et al. | 2007/0194080 A1 | 8/2007 | Swayze et al. |
| 2006/0025811 A1 | 2/2006 | Shelton, IV | 2007/0194081 A1 | 8/2007 | Hueil et al. |
| 2006/0025812 A1 | 2/2006 | Shelton, IV | 2007/0194082 A1 | 8/2007 | Morgan et al. |
| 2006/0025813 A1 | 2/2006 | Shelton et al. | 2007/0233053 A1 | 10/2007 | Shelton, IV et al. |
| 2006/0025816 A1 | 2/2006 | Shelton | 2007/0246505 A1 | 10/2007 | Pace-Floridia et al. |
| 2006/0047303 A1 | 3/2006 | Ortiz et al. | 2007/0295780 A1 | 12/2007 | Shelton et al. |
| 2006/0047307 A1 | 3/2006 | Ortiz et al. | 2008/0029570 A1 | 2/2008 | Shelton et al. |
| 2006/0047308 A1 | 3/2006 | Ortiz et al. | 2008/0029573 A1 | 2/2008 | Shelton et al. |
| 2006/0049229 A1 | 3/2006 | Milliman et al. | 2008/0029574 A1 | 2/2008 | Shelton et al. |
| 2006/0052825 A1 | 3/2006 | Ransick et al. | 2008/0029575 A1 | 2/2008 | Shelton et al. |
| 2006/0060630 A1 | 3/2006 | Shelton, IV et al. | 2008/0029576 A1 | 2/2008 | Shelton et al. |
| 2006/0085033 A1 | 4/2006 | Criscuolo et al. | 2008/0035701 A1 | 2/2008 | Racenet et al. |
| 2006/0086032 A1* | 4/2006 | Valencic et al. ............ 42/70.01 | 2008/0041916 A1 | 2/2008 | Milliman et al. |
| 2006/0087442 A1 | 4/2006 | Smith et al. | 2008/0041917 A1 | 2/2008 | Racenet et al. |
| 2006/0100643 A1 | 5/2006 | Laufer et al. | 2008/0078800 A1 | 4/2008 | Hess et al. |
| 2006/0108393 A1 | 5/2006 | Heinrich et al. | 2008/0078801 A1 | 4/2008 | Shelton et al. |
| 2006/0122636 A1 | 6/2006 | Bailly et al. | 2008/0078802 A1 | 4/2008 | Hess et al. |
| 2006/0142772 A1 | 6/2006 | Ralph et al. | 2008/0078803 A1 | 4/2008 | Shelton et al. |
| 2006/0151567 A1 | 7/2006 | Roy | 2008/0078804 A1 | 4/2008 | Shelton et al. |
| 2006/0180634 A1 | 8/2006 | Shelton, IV et al. | 2008/0078806 A1 | 4/2008 | Omaits et al. |
| 2006/0190028 A1 | 8/2006 | Wales et al. | 2008/0078807 A1 | 4/2008 | Hess et al. |
| 2006/0190029 A1 | 8/2006 | Wales | 2008/0078808 A1 | 4/2008 | Hess et al. |
| 2006/0190031 A1 | 8/2006 | Wales et al. | 2008/0082115 A1 | 4/2008 | Morgan et al. |
| 2006/0212069 A1 | 9/2006 | Shelton, IV | 2008/0082124 A1 | 4/2008 | Hess et al. |
| 2006/0226196 A1 | 10/2006 | Hueil et al. | 2008/0082125 A1 | 4/2008 | Murray et al. |
| 2006/0229665 A1 | 10/2006 | Wales et al. | 2008/0082126 A1 | 4/2008 | Murray et al. |
| 2006/0241655 A1 | 10/2006 | Viola | 2008/0083813 A1 | 4/2008 | Zemlok et al. |
| 2006/0241692 A1 | 10/2006 | McGuckin, Jr. et al. | 2008/0140115 A1 | 6/2008 | Stopek |
| 2006/0273135 A1 | 12/2006 | Beetel | 2008/0164296 A1 | 7/2008 | Shelton et al. |
| 2006/0278680 A1* | 12/2006 | Viola et al. ............... 227/176.1 | 2008/0167522 A1 | 7/2008 | Giordano et al. |
| 2006/0278681 A1 | 12/2006 | Viola et al. | 2008/0167644 A1 | 7/2008 | Shelton et al. |
| 2006/0289602 A1 | 12/2006 | Wales et al. | 2008/0167670 A1 | 7/2008 | Shelton et al. |
| 2007/0023476 A1* | 2/2007 | Whitman et al. ......... 227/175.1 | 2008/0167671 A1 | 7/2008 | Giordano et al. |
| 2007/0023477 A1 | 2/2007 | Whitman et al. | 2008/0167672 A1 | 7/2008 | Giordano et al. |
| 2007/0027469 A1 | 2/2007 | Smith et al. | 2008/0167736 A1 | 7/2008 | Swayze et al. |
| 2007/0034666 A1 | 2/2007 | Holsten et al. | 2008/0169328 A1 | 7/2008 | Shelton |
| 2007/0034668 A1 | 2/2007 | Holsten et al. | 2008/0169329 A1 | 7/2008 | Shelton et al. |
| 2007/0045379 A1 | 3/2007 | Shelton | 2008/0169330 A1 | 7/2008 | Shelton et al. |
| 2007/0055219 A1 | 3/2007 | Whitman et al. | 2008/0169331 A1 | 7/2008 | Shelton et al. |
| 2007/0070574 A1* | 3/2007 | Nerheim et al. ............. 361/232 | 2008/0169332 A1 | 7/2008 | Shelton et al. |
| 2007/0073340 A1 | 3/2007 | Shelton, IV et al. | 2008/0169333 A1 | 7/2008 | Shelton et al. |
| 2007/0073341 A1 | 3/2007 | Smith | 2008/0197167 A1* | 8/2008 | Viola et al. ............... 227/176.1 |
| 2007/0075114 A1 | 4/2007 | Shelton, IV et al. | 2008/0210738 A1 | 9/2008 | Shelton et al. |
| 2007/0083234 A1 | 4/2007 | Shelton, IV et al. | 2008/0237296 A1 | 10/2008 | Boudreaux et al. |
| 2007/0084897 A1 | 4/2007 | Shelton, IV et al. | 2008/0251568 A1 | 10/2008 | Zemlok et al. |
| 2007/0102452 A1 | 5/2007 | Shelton, IV et al. | 2008/0290134 A1 | 11/2008 | Bettuchi et al. |
| 2007/0102453 A1 | 5/2007 | Morgan et al. | 2008/0296343 A1 | 12/2008 | Schall et al. |
| 2007/0102472 A1 | 5/2007 | Shelton, IV | 2008/0296345 A1 | 12/2008 | Shelton, IV et al. |
| 2007/0102473 A1* | 5/2007 | Shelton et al. ............ 227/175.1 | 2008/0296346 A1 | 12/2008 | Shelton, IV et al. |
| 2007/0102474 A1* | 5/2007 | Shelton et al. ............ 227/175.1 | 2008/0296347 A1 | 12/2008 | Shelton, IV et al. |
| 2007/0102475 A1 | 5/2007 | Ortiz et al. | 2008/0300579 A1 | 12/2008 | Broehl et al. |
| 2007/0102476 A1 | 5/2007 | Shelton, IV et al. | 2008/0300580 A1 | 12/2008 | Shelton, IV et al. |
| 2007/0106317 A1 | 5/2007 | Shelton, IV et al. | 2008/0300613 A1 | 12/2008 | Shelton, IV et al. |
| 2007/0114261 A1 | 5/2007 | Ortiz et al. | 2008/0308601 A1 | 12/2008 | Timm et al. |
| 2007/0125826 A1* | 6/2007 | Shelton, IV ............... 227/175.1 | 2008/0308602 A1 | 12/2008 | Timm et al. |
| 2007/0170225 A1 | 7/2007 | Shelton, IV et al. | 2008/0308603 A1 | 12/2008 | Shelton, IV et al. |
| 2007/0173813 A1 | 7/2007 | Odom | 2008/0308606 A1 | 12/2008 | Timm et al. |
| 2007/0175949 A1 | 8/2007 | Shelton, IV et al. | 2008/0308607 A1 | 12/2008 | Timm et al. |
| 2007/0175950 A1 | 8/2007 | Shelton, IV et al. | 2008/0308608 A1 | 12/2008 | Prommersberger |
| 2007/0175951 A1 | 8/2007 | Shelton, IV et al. | 2008/0314954 A1 | 12/2008 | Boudreaux |
| 2007/0175952 A1 | 8/2007 | Shelton, IV et al. | 2008/0314955 A1 | 12/2008 | Boudreaux et al. |
| 2007/0175953 A1 | 8/2007 | Shelton, IV et al. | 2008/0314956 A1 | 12/2008 | Boudreaux |
| 2007/0175955 A1 | 8/2007 | Shelton, IV et al. | 2008/0314957 A1 | 12/2008 | Boudreaux |
| 2007/0175956 A1 | 8/2007 | Swayze et al. | 2008/0314960 A1 | 12/2008 | Marczyk et al. |
| 2007/0175957 A1 | 8/2007 | Shelton, IV et al. | 2008/0314961 A1 | 12/2008 | Boudreaux et al. |

| | | | | | | |
|---|---|---|---|---|---|---|
| 2008/0314962 | A1 | 12/2008 | Boudreaux | DE | 20121753 U1 | 4/2003 |
| 2009/0001121 | A1 | 1/2009 | Hess et al. | DE | 10314072 A1 | 10/2004 |
| 2009/0001122 | A1 | 1/2009 | Prommersberger et al. | EP | 0122046 A1 | 10/1984 |
| 2009/0001123 | A1 | 1/2009 | Morgan et al. | EP | 0070230 B1 | 10/1985 |
| 2009/0001124 | A1 | 1/2009 | Hess et al. | EP | 0033548 B1 | 5/1986 |
| 2009/0001125 | A1 | 1/2009 | Hess et al. | EP | 0276104 A2 | 7/1988 |
| 2009/0001126 | A1 | 1/2009 | Hess et al. | EP | 0552050 | 7/1993 |
| 2009/0001128 | A1 | 1/2009 | Weisenburgh, II et al. | EP | 0552423 | 7/1993 |
| 2009/0001130 | A1 | 1/2009 | Hess et al. | EP | 0639349 A2 | 2/1994 |
| 2009/0005807 | A1 | 1/2009 | Hess et al. | EP | 0324636 B1 | 3/1994 |
| 2009/0005808 | A1 | 1/2009 | Hess et al. | EP | 0593920 A1 | 4/1994 |
| 2009/0005809 | A1 | 1/2009 | Hess et al. | EP | 0600182 A2 | 6/1994 |
| 2009/0012556 | A1 | 1/2009 | Boudreaux et al. | EP | 0630612 A1 | 12/1994 |
| 2009/0076534 | A1 | 3/2009 | Shelton, IV et al. | EP | 0634144 | 1/1995 |
| 2009/0090763 | A1 | 4/2009 | Zemlok et al. | EP | 0646356 A2 | 4/1995 |
| 2009/0200355 | A1 | 8/2009 | Baxter, III et al. | EP | 0646357 A1 | 4/1995 |
| 2009/0206123 | A1 | 8/2009 | Doll et al. | EP | 0653189 A2 | 5/1995 |
| 2009/0206124 | A1 | 8/2009 | Hall et al. | EP | 0669104 A1 | 8/1995 |
| 2009/0206125 | A1 | 8/2009 | Huitema et al. | EP | 0511470 B1 | 10/1995 |
| 2009/0206126 | A1 | 8/2009 | Huitema et al. | EP | 0679367 A2 | 11/1995 |
| 2009/0206128 | A1 | 8/2009 | Hueil et al. | EP | 0392547 B1 | 12/1995 |
| 2009/0206129 | A1 | 8/2009 | Doll et al. | EP | 0685204 A1 | 12/1995 |
| 2009/0206130 | A1 | 8/2009 | Hall et al. | EP | 0699418 A1 | 3/1996 |
| 2009/0206131 | A1 | 8/2009 | Weisenburgh, II et al. | EP | 0702937 A1 | 3/1996 |
| 2009/0206132 | A1 | 8/2009 | Hueil et al. | EP | 0705571 A1 | 4/1996 |
| 2009/0206133 | A1 | 8/2009 | Morgan et al. | EP | 0484677 B2 | 6/1996 |
| 2009/0206134 | A1 | 8/2009 | Swayze et al. | EP | 0541987 B1 | 7/1996 |
| 2009/0206135 | A1 | 8/2009 | Hall et al. | EP | 0667119 B1 | 7/1996 |
| 2009/0206136 | A1 | 8/2009 | Moore et al. | EP | 0770355 A1 | 5/1997 |
| 2009/0206137 | A1 | 8/2009 | Hall et al. | EP | 0503662 B1 | 6/1997 |
| 2009/0206138 | A1 | 8/2009 | Smith et al. | EP | 0578425 B1 | 9/1997 |
| 2009/0206139 | A1 | 8/2009 | Hall et al. | EP | 0625335 B1 | 11/1997 |
| 2009/0206140 | A1 | 8/2009 | Scheib et al. | EP | 0592244 B1 | 1/1998 |
| 2009/0206141 | A1 | 8/2009 | Huitema et al. | EP | 0648476 B1 | 1/1998 |
| 2009/0206142 | A1 | 8/2009 | Huitema et al. | EP | 0676173 B1 | 9/1998 |
| 2009/0206143 | A1 | 8/2009 | Huitema et al. | EP | 0603472 B1 | 11/1998 |
| 2009/0206144 | A1 | 8/2009 | Doll et al. | EP | 0605351 B1 | 11/1998 |
| 2009/0209946 | A1 | 8/2009 | Swayze et al. | EP | 0878169 A1 | 11/1998 |
| 2009/0218384 | A1 | 9/2009 | Aranyi | EP | 0879742 A1 | 11/1998 |
| 2009/0242610 | A1 | 10/2009 | Shelton, IV et al. | EP | 0760230 B1 | 2/1999 |
| 2009/0255974 | A1 | 10/2009 | Viola | EP | 0537572 B1 | 6/1999 |
| 2009/0255975 | A1 | 10/2009 | Zemlok et al. | EP | 1090592 A1 | 4/2001 |
| 2009/0255976 | A1 | 10/2009 | Marczyk et al. | EP | 1256318 B1 | 5/2001 |
| 2009/0255977 | A1 | 10/2009 | Zemlok | EP | 0908152 B1 | 1/2002 |
| 2009/0255978 | A1 | 10/2009 | Viola et al. | EP | 0872213 B1 | 5/2002 |
| 2009/0289096 | A1 | 11/2009 | Shelton, IV et al. | EP | 1238634 A2 | 9/2002 |
| 2009/0292283 | A1 | 11/2009 | Odom | EP | 0656188 B1 | 1/2003 |
| 2010/0032470 | A1 | 2/2010 | Hess et al. | EP | 0829235 B1 | 6/2003 |
| 2010/0065605 | A1 | 3/2010 | Shelton, VI et al. | EP | 0813843 B1 | 10/2003 |
| 2010/0065609 | A1 | 3/2010 | Schwemberger | EP | 0741996 B1 | 2/2004 |
| 2010/0069942 | A1 | 3/2010 | Shelton, IV | EP | 0705570 B1 | 4/2004 |
| 2010/0072251 | A1 | 3/2010 | Baxter, III et al. | EP | 1086713 B1 | 5/2004 |
| 2010/0072252 | A1 | 3/2010 | Baxter, III et al. | EP | 1426012 | 6/2004 |
| 2010/0072253 | A1 | 3/2010 | Baxter, III et al. | EP | 0888749 B1 | 9/2004 |
| 2010/0072256 | A1 | 3/2010 | Baxter, III et al. | EP | 1477119 A1 | 11/2004 |
| 2010/0076474 | A1 | 3/2010 | Yates et al. | EP | 1479345 A1 | 11/2004 |
| 2010/0076475 | A1 | 3/2010 | Yates et al. | EP | 1479347 A1 | 11/2004 |
| 2010/0089970 | A1 | 4/2010 | Smith et al. | EP | 1479348 A1 | 11/2004 |
| 2010/0089974 | A1 | 4/2010 | Shelton, IV | EP | 1520521 A1 | 4/2005 |
| 2010/0096435 | A1 | 4/2010 | Fuchs et al. | EP | 1520523 A1 | 4/2005 |
| 2010/0133317 | A1 | 6/2010 | Shelton, IV et al. | EP | 1520525 A1 | 4/2005 |
| 2010/0133318 | A1 | 6/2010 | Boudreaux | EP | 1522264 A1 | 4/2005 |
| | | | | EP | 1550408 A1 | 7/2005 |
| | | FOREIGN PATENT DOCUMENTS | | EP | 1557129 A1 | 7/2005 |
| | | | | EP | 1064883 B1 | 8/2005 |
| CA | | 2512960 A1 | 1/2006 | EP | 1157666 B1 | 9/2005 |
| CA | | 2514274 A1 | 1/2006 | EP | 1621138 A2 | 2/2006 |
| DE | | 273689 C | 5/1914 | EP | 1621139 A2 | 2/2006 |
| DE | | 1775926 A | 1/1972 | EP | 1621141 A2 | 2/2006 |
| DE | | 9412228 U | 9/1994 | EP | 1621145 A2 | 2/2006 |
| DE | | 19924311 A1 | 11/2000 | EP | 1621151 A2 | 2/2006 |
| DE | | 69328576 T2 | 1/2001 | EP | 1652481 A2 | 5/2006 |
| DE | | 20112837 U1 | 10/2001 | EP | 1382303 B1 | 6/2006 |

| | | | | | | |
|---|---|---|---|---|---|---|
| EP | 1045672 | B1 | 8/2006 | WO | WO 00/72765 A1 | 12/2000 |
| EP | 1617768 | B1 | 8/2006 | WO | WO-0105702 | 1/2001 |
| EP | 1702567 | A2 | 9/2006 | WO | WO 01/10482 A1 | 2/2001 |
| EP | 1129665 | B1 | 11/2006 | WO | WO 01/54594 A1 | 8/2001 |
| EP | 1256317 | B1 | 12/2006 | WO | WO 01/62158 A2 | 8/2001 |
| EP | 1728473 | A1 | 12/2006 | WO | WO 01/62162 A1 | 8/2001 |
| EP | 1728475 | A2 | 12/2006 | WO | WO-0162164 | 8/2001 |
| EP | 1479346 | B1 | 1/2007 | WO | WO 01/91646 A1 | 12/2001 |
| EP | 1484024 | B1 | 1/2007 | WO | WO 02/07608 A2 | 1/2002 |
| EP | 1754445 | A2 | 2/2007 | WO | WO 02/07618 A1 | 1/2002 |
| EP | 1759812 | A1 | 3/2007 | WO | WO 02/17799 A1 | 3/2002 |
| EP | 1769756 | A1 | 4/2007 | WO | WO 02/19920 A1 | 3/2002 |
| EP | 1769758 | A1 | 4/2007 | WO | WO 02/30297 A2 | 4/2002 |
| EP | 1785097 | A2 | 5/2007 | WO | WO 02/32322 A2 | 4/2002 |
| EP | 1790293 | A2 | 5/2007 | WO | WO-0243571 | 6/2002 |
| EP | 1800610 | A1 | 6/2007 | WO | WO 02/058568 A1 | 8/2002 |
| EP | 1300117 | B1 | 8/2007 | WO | WO 02/060328 A1 | 8/2002 |
| EP | 1813199 | A1 | 8/2007 | WO | WO 02/067785 A2 | 9/2002 |
| EP | 1813201 | A1 | 8/2007 | WO | WO 02/098302 A1 | 12/2002 |
| EP | 1813203 | A2 | 8/2007 | WO | WO-03000138 | 1/2003 |
| EP | 1813207 | A1 | 8/2007 | WO | WO-03001329 | 1/2003 |
| EP | 1813209 | A1 | 8/2007 | WO | WO 03/013363 A1 | 2/2003 |
| EP | 1402821 | B1 | 12/2007 | WO | WO 03/020106 A2 | 3/2003 |
| EP | 1872727 | A1 | 1/2008 | WO | WO 03/020139 A2 | 3/2003 |
| EP | 1839596 | A2 | 2/2008 | WO | WO 03/079909 A3 | 3/2003 |
| EP | 1897502 | A1 | 3/2008 | WO | WO 03/030743 A2 | 4/2003 |
| EP | 1702568 | B1 | 7/2008 | WO | WO 03/037193 A1 | 5/2003 |
| EP | 1970014 | A1 | 9/2008 | WO | WO 03/047436 A3 | 6/2003 |
| EP | 1980213 | A2 | 10/2008 | WO | WO 03/057048 A1 | 7/2003 |
| EP | 1759645 | B1 | 11/2008 | WO | WO 03/057058 A1 | 7/2003 |
| EP | 1693008 | B1 | 12/2008 | WO | WO-03063694 | 8/2003 |
| EP | 2000102 | A2 | 12/2008 | WO | WO-03077769 | 9/2003 |
| EP | 1749486 | B1 | 3/2009 | WO | WO 03/082126 A1 | 10/2003 |
| EP | 2090256 | A2 | 8/2009 | WO | WO 03/088845 A2 | 10/2003 |
| EP | 1813206 | B1 | 4/2010 | WO | WO 03/090630 A2 | 11/2003 |
| FR | 999646 | A | 2/1952 | WO | WO 03/094743 A1 | 11/2003 |
| FR | 1112936 | A | 3/1956 | WO | WO 03/094745 A1 | 11/2003 |
| FR | 2765794 | A | 1/1999 | WO | WO 03/094746 A1 | 11/2003 |
| GB | 939929 | A | 10/1963 | WO | WO 03/094747 A1 | 11/2003 |
| GB | 1210522 | A | 10/1970 | WO | WO 03/101313 A1 | 12/2003 |
| GB | 2336214 | A | 10/1999 | WO | WO 03/105698 A2 | 12/2003 |
| JP | 6007357 | A | 1/1994 | WO | WO 03/105702 A2 | 12/2003 |
| JP | 7051273 | A | 2/1995 | WO | WO 2004/006980 A2 | 1/2004 |
| JP | 8033641 | A | 2/1996 | WO | WO 2004/028585 A2 | 4/2004 |
| JP | 8229050 | A | 9/1996 | WO | WO 2004/032754 A2 | 4/2004 |
| JP | 2000287987 | A | 10/2000 | WO | WO 2004/032760 A2 | 4/2004 |
| JP | 2001286477 | A | 10/2001 | WO | WO 2004/032762 A1 | 4/2004 |
| JP | 2002369820 | A | 12/2002 | WO | WO 2004/032763 A2 | 4/2004 |
| JP | 2005505322 | T | 2/2005 | WO | WO 2004/047653 A2 | 6/2004 |
| JP | 2005103293 | A | 4/2005 | WO | WO 2004/049956 A2 | 6/2004 |
| RU | 2187249 | C2 | 8/2002 | WO | WO 2004/086987 A1 | 10/2004 |
| RU | 2225170 | C2 | 3/2004 | WO | WO 2004/096057 A2 | 11/2004 |
| SU | 1377053 | A1 | 2/1988 | WO | WO 2004/105621 A1 | 12/2004 |
| SU | 1561964 | A1 | 5/1990 | WO | WO 2004/112618 A2 | 12/2004 |
| SU | 1722476 | A1 | 3/1992 | WO | WO 2004/112652 A2 | 12/2004 |
| WO | WO 93/08755 | A1 | 5/1993 | WO | WO 2005/027983 A2 | 3/2005 |
| WO | WO 95/18572 | A1 | 7/1995 | WO | WO 2005/037329 A2 | 4/2005 |
| WO | WO 95/23557 | A1 | 9/1995 | WO | WO 2005/078892 A1 | 8/2005 |
| WO | WO 95/29639 | A1 | 11/1995 | WO | WO 2005/096954 A2 | 10/2005 |
| WO | WO 96/22055 | A1 | 7/1996 | WO | WO 2005/112808 A1 | 12/2005 |
| WO | WO 96/35464 | A1 | 11/1996 | WO | WO 2005/115251 A2 | 12/2005 |
| WO | WO 97/34533 | A1 | 9/1997 | WO | WO 2006/044490 A2 | 4/2006 |
| WO | WO 97/39688 | A2 | 10/1997 | WO | WO 2006/044581 A2 | 4/2006 |
| WO | WO 98/17180 | A1 | 4/1998 | WO | WO 2006/044810 A2 | 4/2006 |
| WO | WO 98/30153 | A1 | 7/1998 | WO | WO 2006/083748 A2 | 8/2006 |
| WO | WO 99/12483 | A1 | 3/1999 | WO | WO 2006/115958 A1 | 11/2006 |
| WO | WO 99/15086 | A1 | 4/1999 | WO | WO 2006/132992 A1 | 12/2006 |
| WO | WO 99/34744 | A1 | 7/1999 | WO | WO 2007/002180 A2 | 1/2007 |
| WO | WO 99/45849 | A1 | 9/1999 | WO | WO 2007/016290 A2 | 2/2007 |
| WO | WO 00/24322 | A1 | 5/2000 | WO | WO 2007/018898 A2 | 2/2007 |
| WO | WO 00/57796 | A1 | 10/2000 | WO | WO 2007/098220 A2 | 8/2007 |
| WO | WO 00/64365 | A1 | 11/2000 | WO | WO 2007/121579 A1 | 11/2007 |
| WO | WO 00/72762 | A1 | 12/2000 | WO | WO 2007/137304 A2 | 11/2007 |

| WO | WO 2007/139734 | A2 | 12/2007 |
| WO | WO 2007/142625 | A2 | 12/2007 |
| WO | WO 2008/039270 | A1 | 4/2008 |
| WO | WO 2008/045383 | A2 | 4/2008 |

OTHER PUBLICATIONS

U.S. Appl. No. 11/267,811, "Surgical Stapling Instruments Structured For Pump-Assisted Delivery Of Medical Agents," by Frederick E. Shelton, IV and Jerome R. Morgan, filed Nov. 4, 2005.

U.S. Appl. No. 11/267,383, "Surgical Stapling Instruments Structured For Delivery of Medical Agents," by Jerome R. Morgan and Frederick E. Shelton, IV, filed Nov. 4, 2005.

Singapore Examination Report for Application No. 200700736-2, dated Jan. 19, 2009 (11 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

U.S. Appl. No. 12/124,655, filed May 21, 2008.
U.S. Appl. No. 12/032,024, filed Feb. 15, 2008.
European Search Report, Application No. 07250373.3, dated Jul. 4, 2007 (8 pages).
Office Action issued on Apr. 10, 2007 in U.S. Appl. No. 11/343,439.
Office Action issued on Jun. 13, 2007 in U.S. Appl. No. 11/343,447.
Office Action issued on Mar. 7, 2007 in U.S. Appl. No. 11/343,573.
Office Action issued on Jul. 5, 2007 in U.S. Appl. No. 11/343,498.
Office Action issued on Jun. 20, 2007 in U.S. Appl. No. 11/343,562.
Office Action issued on Jun. 28, 2007 in U.S. Appl. No. 11/344,024.
Office Action issued on Apr. 5, 2007 in U.S. Appl. No. 11/343,321.
Office Action issued on May 16, 2007 in U.S. Appl. No. 11/343,563.
Office Action issued on Feb. 2, 2007 in U.S. Appl. No. 11/344,020.
Office Action issued on Feb. 13, 2007 in U.S. Appl. No. 11/344,021.
Office Action issued on Jun. 18, 2007 in U.S. Appl. No. 11/343,545.
Office Action issued on Jun. 25, 2007 in U.S. Appl. No. 11/343,546.
Office Action issued on Jul. 19, 2007 in U.S. Appl. No. 11/344,021.
Office Action issued on Jul. 20, 2007 in U.S. Appl. No. 11/344,035.
Office Action issued on Jul. 25, 2007 in U.S. Appl. No. 11/344,020.
Office Action issued on Aug. 8, 2007 in U.S. Appl. No. 11/343,573.
The Sodem Aseptic Battery Transfer Kit, Sodem Systems, 2000, 3 pages.
"Biomedical Coatings," Fort Wayne Metals, Research Products Corporation, obtained online at wwww.fwmetals.com on Jun. 21, 2010 (1 page).

* cited by examiner

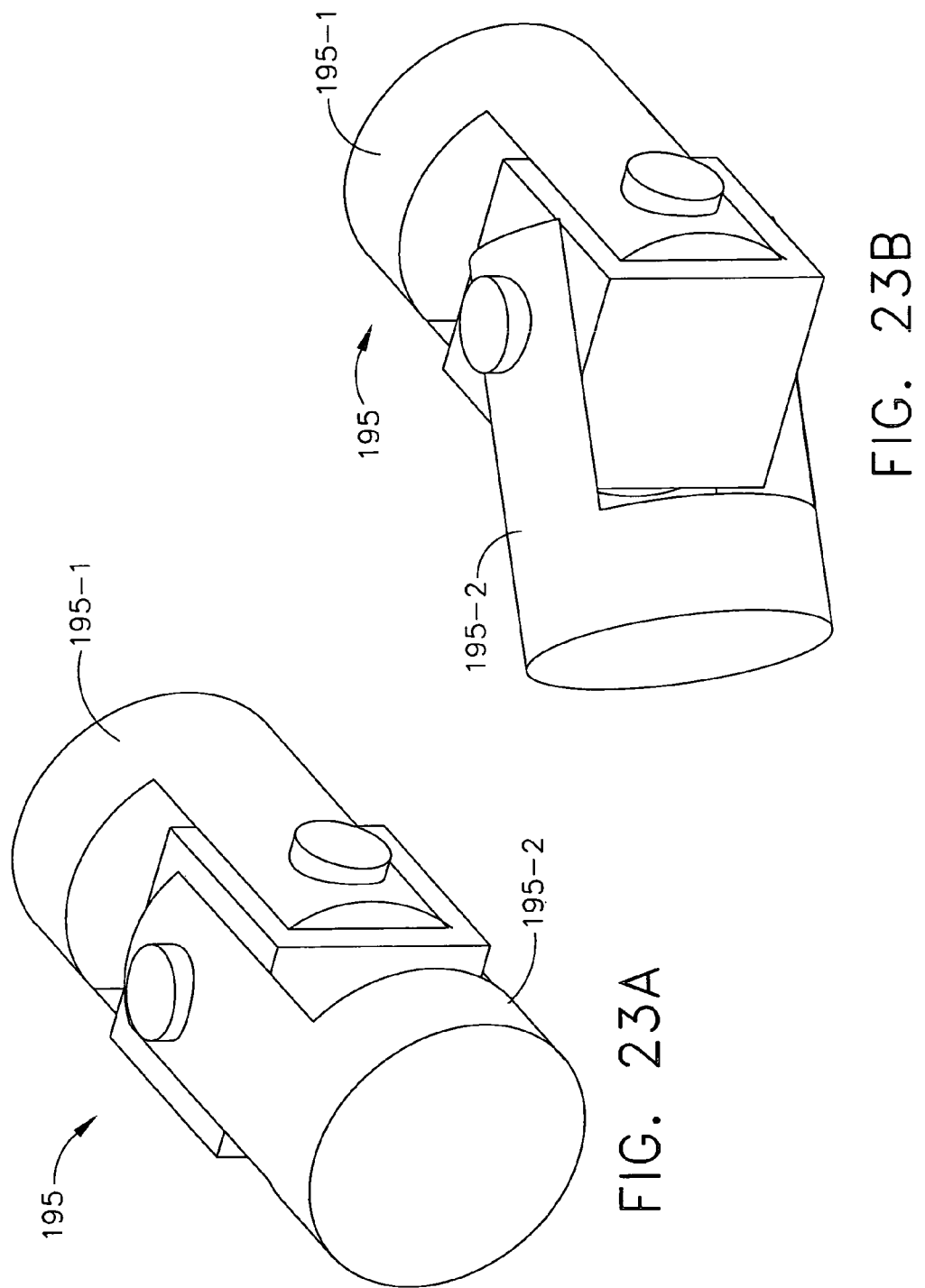

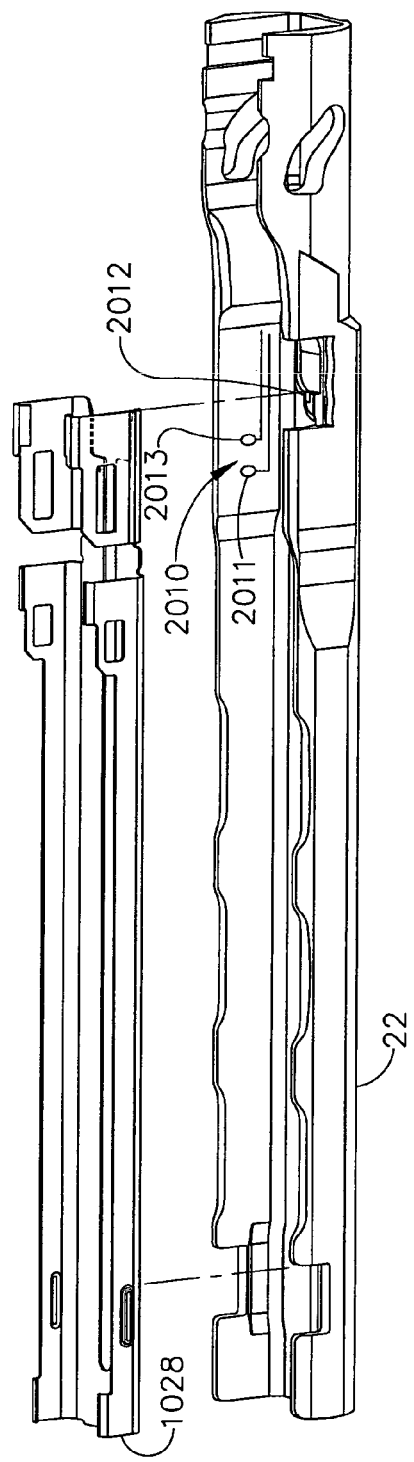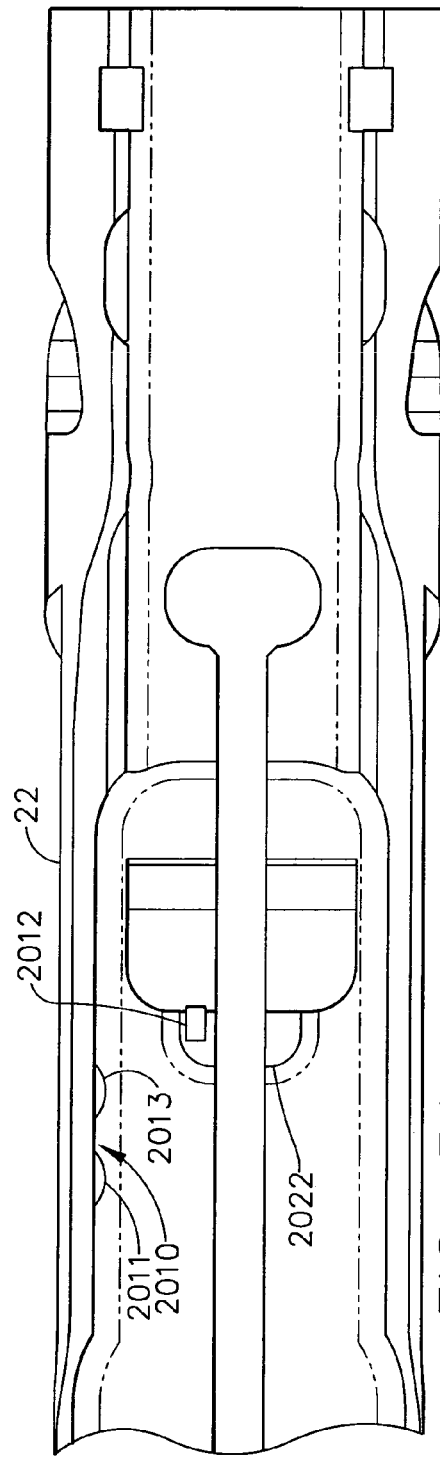

SURGICAL INSTRUMENT HAVING RECORDING CAPABILITIES

CROSS-REFERENCE TO RELATED APPLICATIONS

The present application is related to the following concurrently-filed U.S. patent applications, which are incorporated herein by reference:

U.S. patent application Ser. No. 11/343,498, now U.S. Publication No. 2007/0175958, entitled MOTOR-DRIVEN SURGICAL CUTTING AND FASTENING INSTRUMENT WITH USER FEEDBACK SYSTEM Inventors: Frederick E. Shelton, IV, John Ouwerkerk and Jerome R. Morgan U.S. patent application Ser. No. 11/343,573, now U.S. Pat. No. 7,416,101, entitled MOTOR-DRIVEN SURGICAL CUTTING AND FASTENING INSTRUMENT WITH LOADING FORCE FEEDBACK Inventors: Frederick E. Shelton, IV, John N. Ouwerkerk, Jerome R. Morgan, and Jeffrey S. Swayze U.S. patent application Ser. No. 11/344,035, now U.S. Pat. No. 7,422,139, entitled MOTOR-DRIVEN SURGICAL CUTTING AND FASTENING INSTRUMENT WITH TACTILE POSITION FEEDBACK Inventors: Frederick E. Shelton, IV, John N. Ouwerkerk, Jerome R. Morgan, and Jeffrey S. Swayze U.S. patent application Ser. No. 11/343,447, now U.S. Publication No. 2007/0175957, entitled MOTOR-DRIVEN SURGICAL CUTTING AND FASTENING INSTRUMENT WITH ADAPTIVE USER FEEDBACK Inventors: Frederick E. Shelton, IV, John N. Ouwerkerk, and Jerome R. Morgan U.S. patent application Ser. No. 11/343,562, now U.S. Pat. No. 7,568,603, entitled MOTOR-DRIVEN SURGICAL CUTTING AND FASTENING INSTRUMENT WITH ARTICULATABLE END EFFECTOR Inventors: Frederick E. Shelton, IV and Christoph L. Gillum U.S. patent application Ser. No. 11/344,024, now U.S. Publication No. 2007/0175953, entitled MOTOR-DRIVEN SURGICAL CUTTING AND FASTENING INSTRUMENT WITH MECHANICAL CLOSURE SYSTEM Inventors: Frederick E. Shelton, IV and Christoph L. Gillum U.S. patent application Ser. No. 11/343,321, now U.S. Publication No. 2007/0175955, entitled SURGICAL CUTTING AND FASTENING INSTRUMENT WITH CLOSURE TRIGGER LOCKING MECHANISM Inventors: Frederick E. Shelton, IV and Kevin R. Doll U.S. patent application Ser. No 11/343,563, now U.S. Publication No. 2007/0175951, entitled GEARING SELECTOR FOR A POWERED SURGICAL CUTTING AND FASTENING STAPLING INSTRUMENT Inventors: Frederick E. Shelton, IV, Jeffrey S. Swayze, Eugene L. Timperman U.S. patent application Ser. No. 11/344,020, now U.S. Pat. No. 7,464,846, entitled SURGICAL INSTRUMENT HAVING A REMOVABLE BATTERY Inventors: Frederick E. Shelton, IV, Kevin R. Doll, Jeffrey S. Swayze and Eugene Timperman U.S. patent application Ser. No. 11/343,439, now U.S. Pat. No. 7,644,848, entitled ELECTRONIC LOCKOUTS AND SURGICAL INSTRUMENT INCLUDING SAME Inventors: Jeffrey S. Swayze, Frederick E. Shelton, IV, Kevin R. Doll U.S. patent application Ser. No. 11/343,547, now U.S. Publication No. 2007/0179476, entitled ENDOSCOPIC SURGICAL INSTRUMENT WITH A HANDLE THAT CAN ARTICULATE WITH RESPECT TO THE SHAFT Inventors: Frederick E. Shelton, IV, Jeffrey S. Swayze, Mark S. Ortiz, and Leslie M. Fugikawa U.S. patent application Ser. No. 11/344,021, now U.S. Pat. No. 7,464,849, entitled ELECTRO-MECHANICAL SURGICAL CUTTING AND FASTENING INSTRUMENT HAVING A ROTARY FIRING AND CLOSURE SYSTEM WITH PARALLEL CLOSURE AND ANVIL ALIGNMENT COMPONENTS Inventors: Frederick E. Shelton, IV, Stephen J. Balek and Eugene L. Timperman U.S. patent application Ser. No. 11/343,546, now U.S. Publication No. 2007/0175950, entitled DISPOSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR Inventors: Frederick E. Shelton, IV, Michael S. Cropper, Joshua M. Broehl, Ryan S. Crisp, Jamison J. Float, Eugene L. Timperman U.S. patent application Ser. No. 11/343,545, now U.S. Publication No. 2007/0175949, entitled SURGICAL INSTRUMENT HAVING A FEEDBACK SYSTEM Inventors: Frederick E. Shelton, IV, Jerome R. Morgan, Kevin R. Doll, Jeffrey S. Swayze and Eugene Timperman

BACKGROUND

The present invention relates in general to surgical instruments, and more particularly to minimally invasive surgical instruments capable of recording various conditions of the instrument.

Endoscopic surgical instruments are often preferred over traditional open surgical devices because a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, entitled "SURGICAL STAPLER INSTRUMENT" to Knodel et al., which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling of the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

When endoscopic surgical instruments fail, they are often returned to the manufacturer, or other entity, for analysis of the failure. If the failure resulted in a critical class of defect in the instrument, it is necessary for the manufacturer to determine the cause of the failure and determine whether a design change is required. In that case, the manufacturer may spend many hundreds of man-hours analyzing a failed instrument and attempting to reconstruct the conditions under which it failed based only on the damage to the instrument. It can be expensive and very challenging to analyze instrument failures in this way. Also, many of these analyses simply conclude that the failure was due to improper use of the instrument.

SUMMARY

In one general aspect, the present invention is directed to a surgical instrument. The surgical instrument has an end effector and a trigger in communication with the end effector. The surgical instrument also has a first sensor and an externally accessible memory device in communication with the first sensor. The first sensor has an output that represents a first condition of either the trigger or the end effector. The memory device is configured to record the output of the first sensor. In various embodiments, memory device may include an output port and/or a removable storage medium.

Also, in various embodiments, the output of the first sensor represents a condition of the end effector and the instrument further comprises a second sensor with an output representing a condition of the trigger. The memory device is configured to record the output of the first sensor and the second sensor.

In another general aspect, the present invention is directed to a method of recording the state of a surgical instrument. The method comprises the step of monitoring outputs of a plurality of sensors. The outputs represent conditions of the surgical instrument. The method also comprises the step of recording the outputs to a memory device when at least one of the conditions of the surgical instrument changes. In various embodiments, the method may also comprise the step of providing the recorded outputs of the plurality of sensors to an outside device.

DRAWINGS

Various embodiments of the present invention are described herein by way of example in conjunction with the following figures, wherein FIGS. 1 and 2 are perspective views of a surgical cutting and fastening instrument according to various embodiments of the present invention;

Figure 24A:
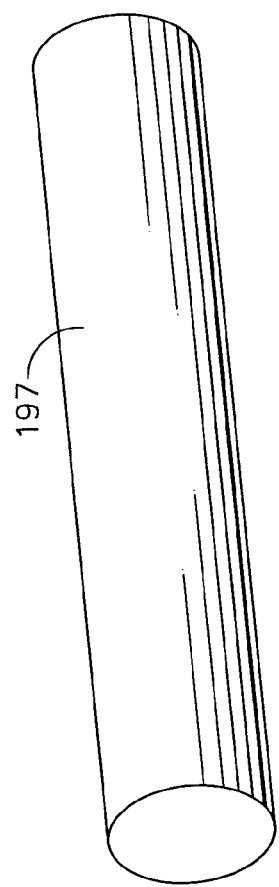
Figure 24B:
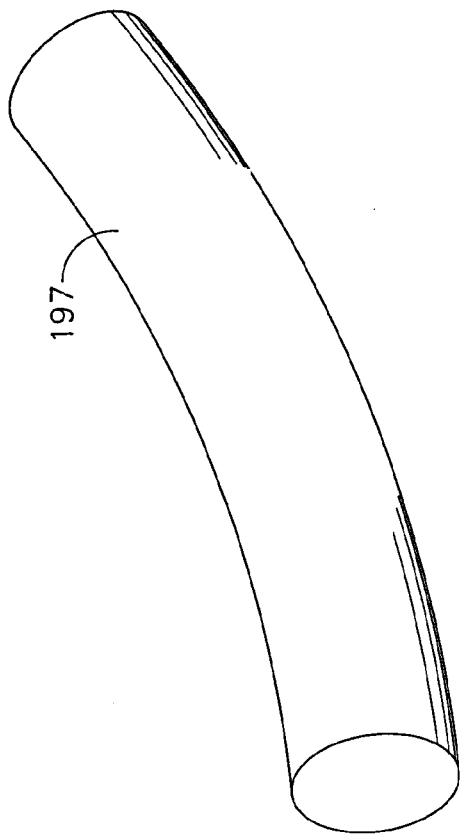
Figure 25:
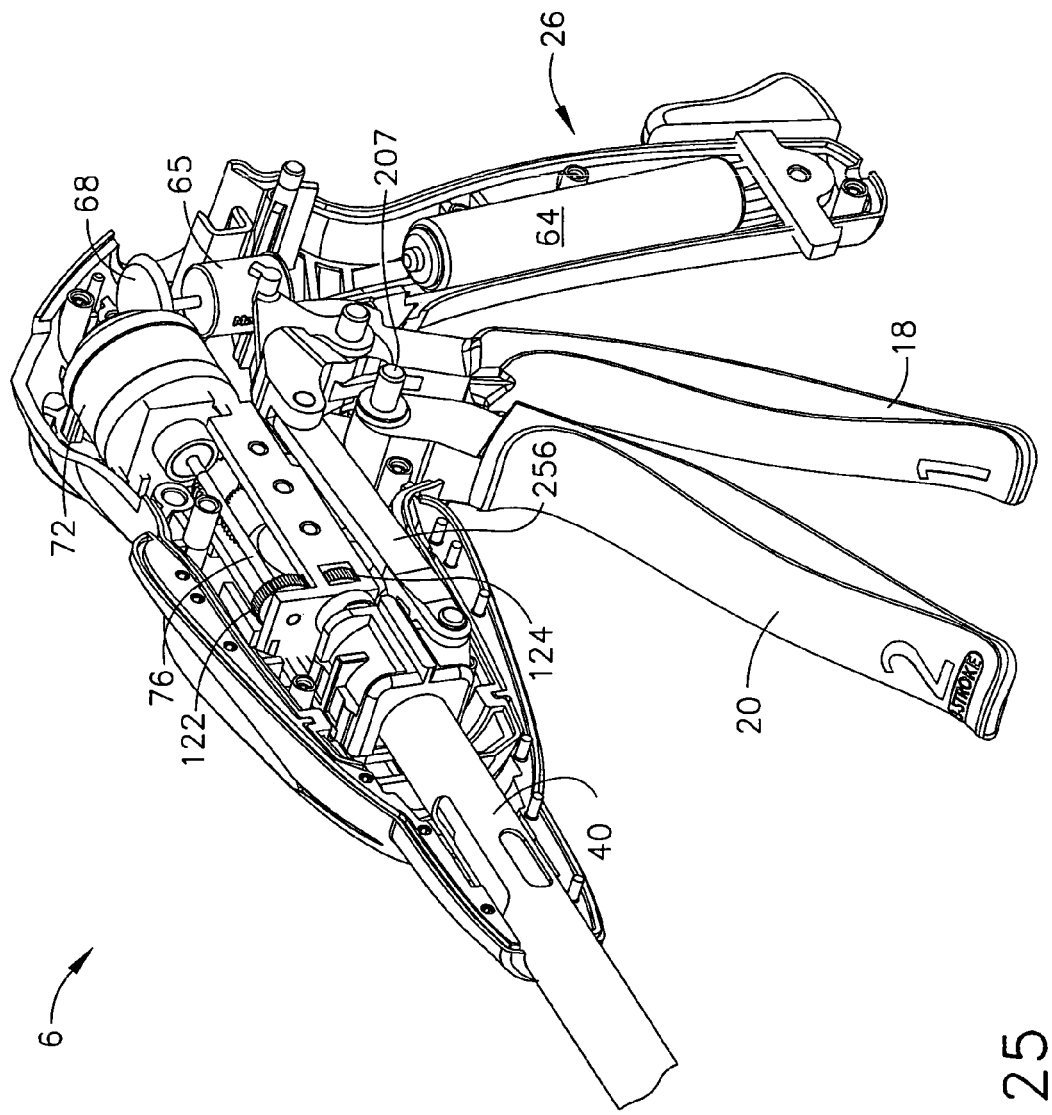
Figure 26:
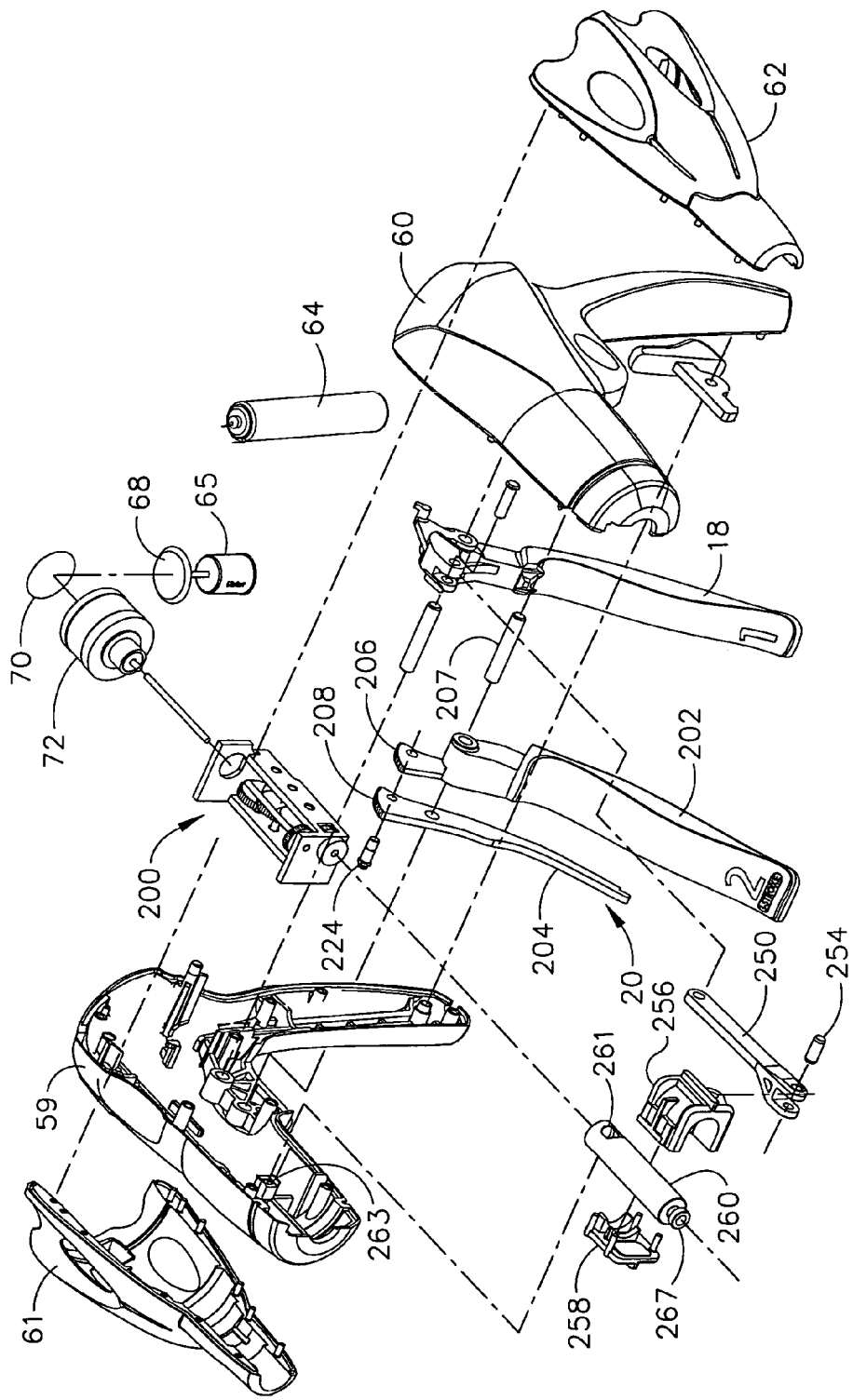
Figure 27:
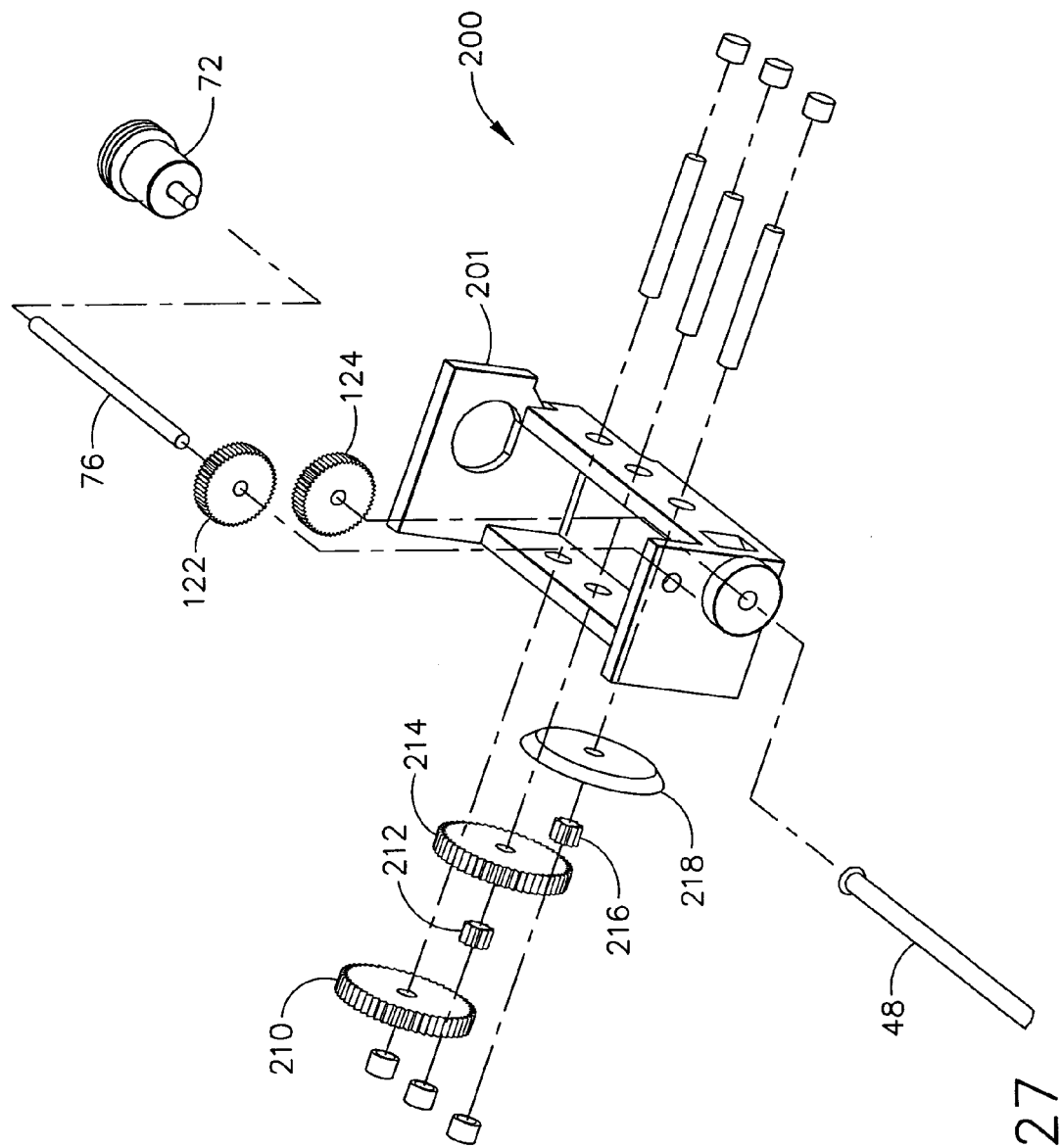
Figure 28:
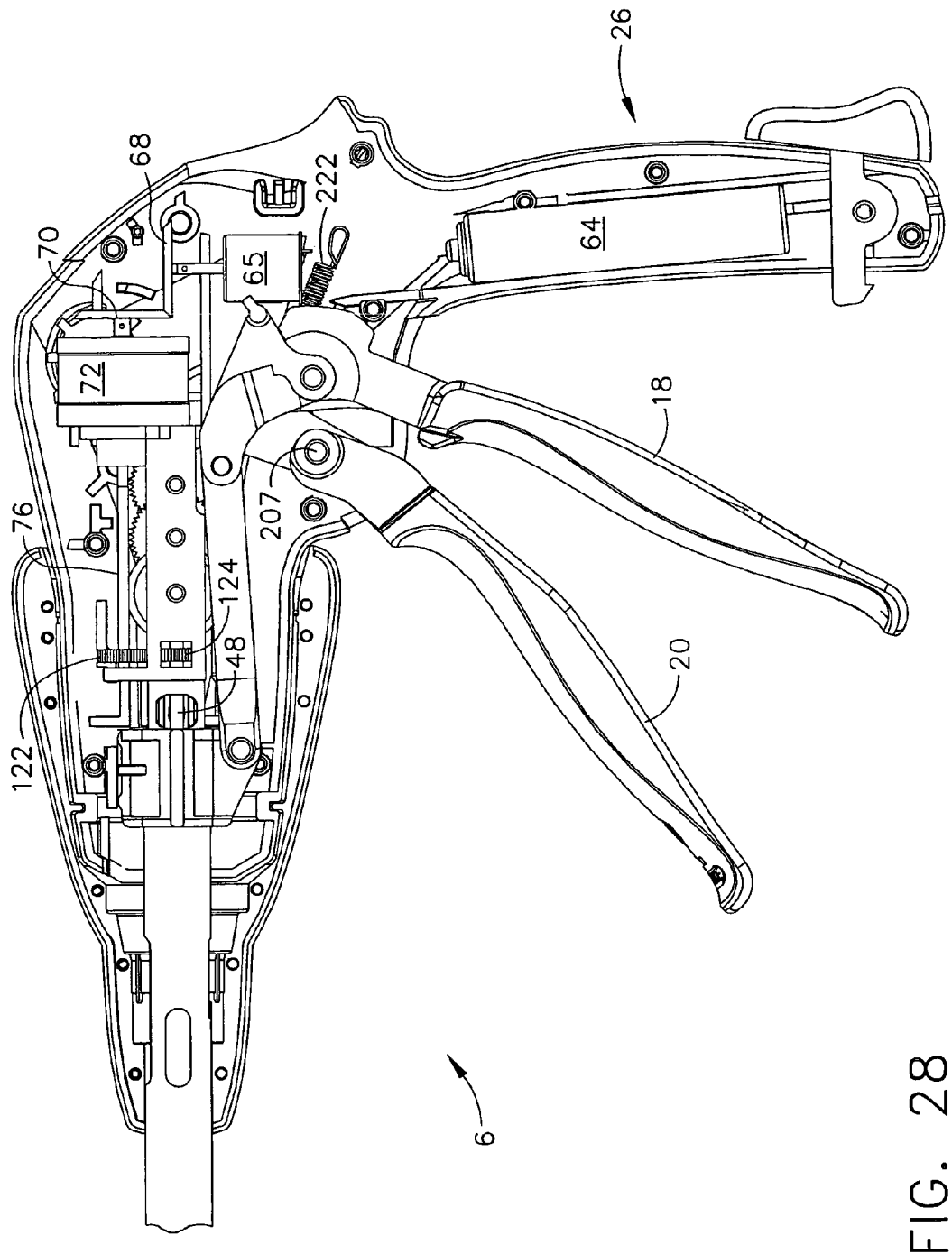
Figure 29:
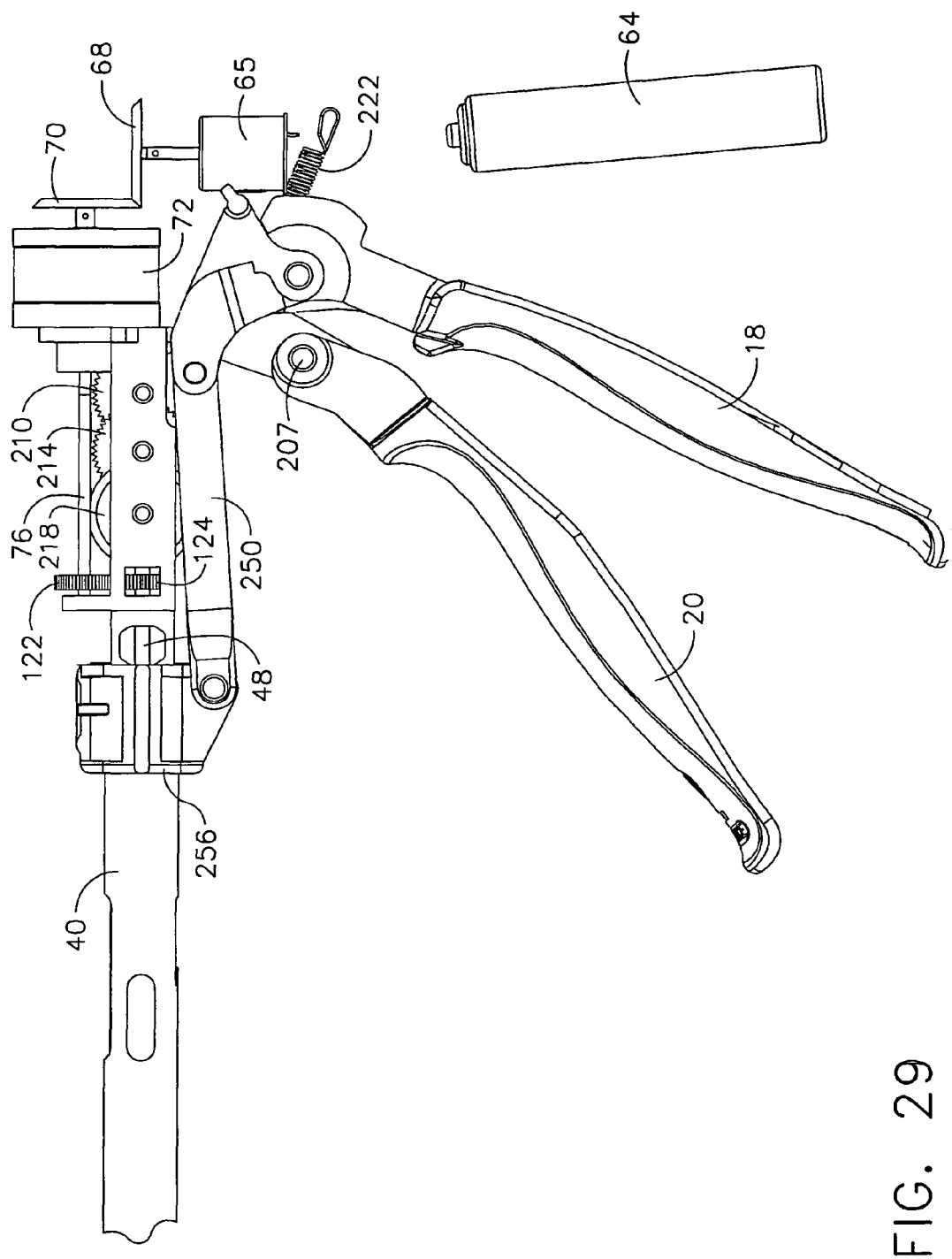
Figure 30:
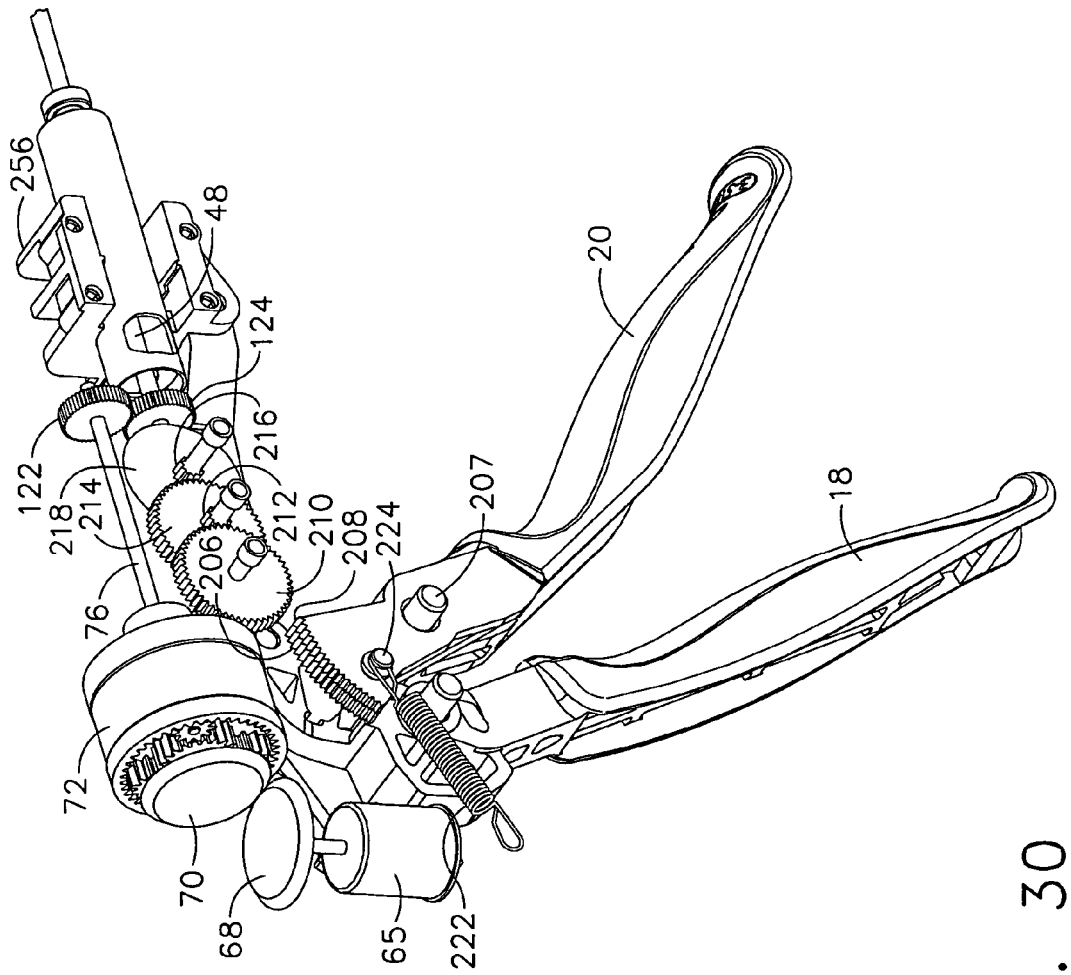
Figure 31:
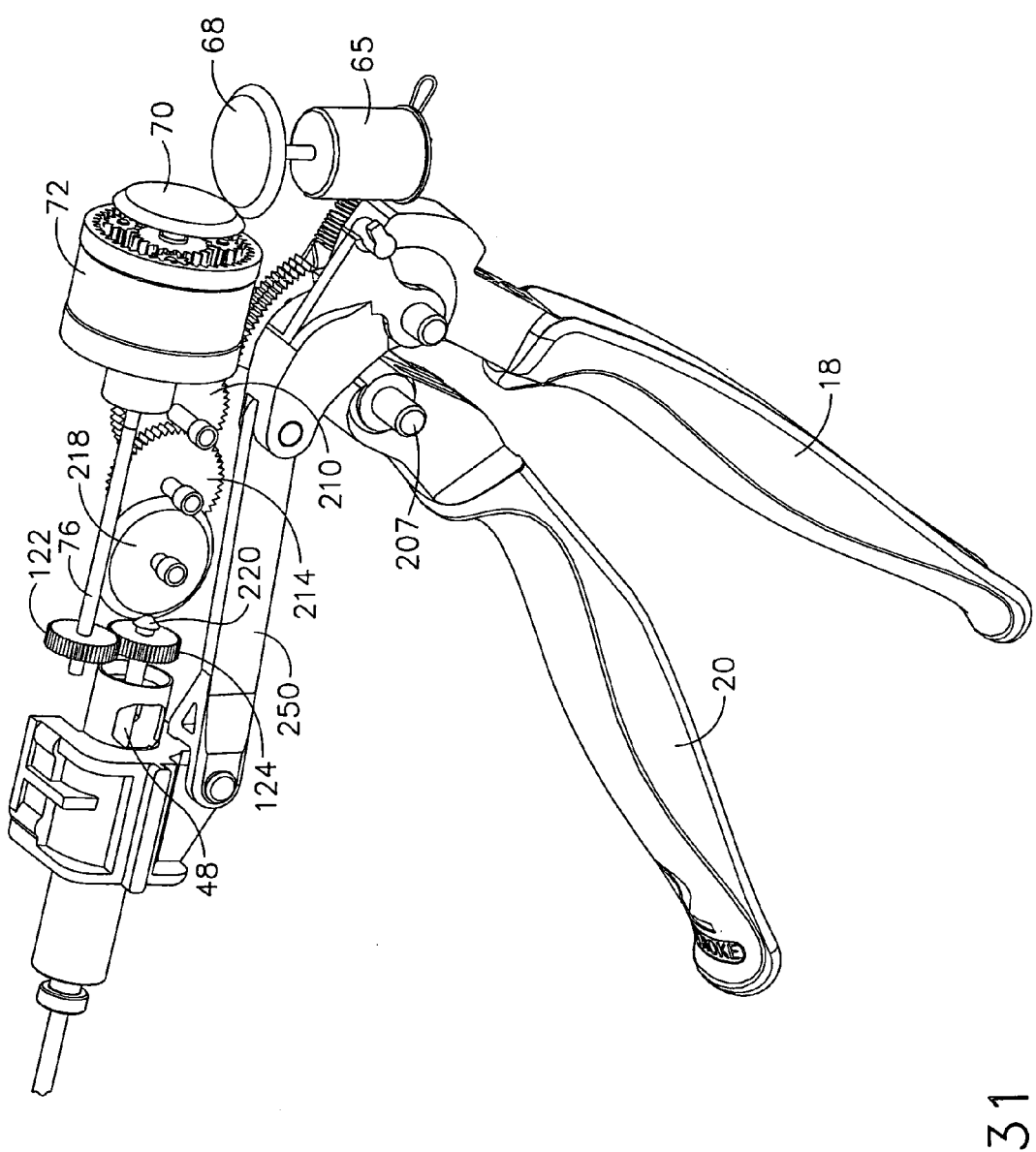
Figure 41:
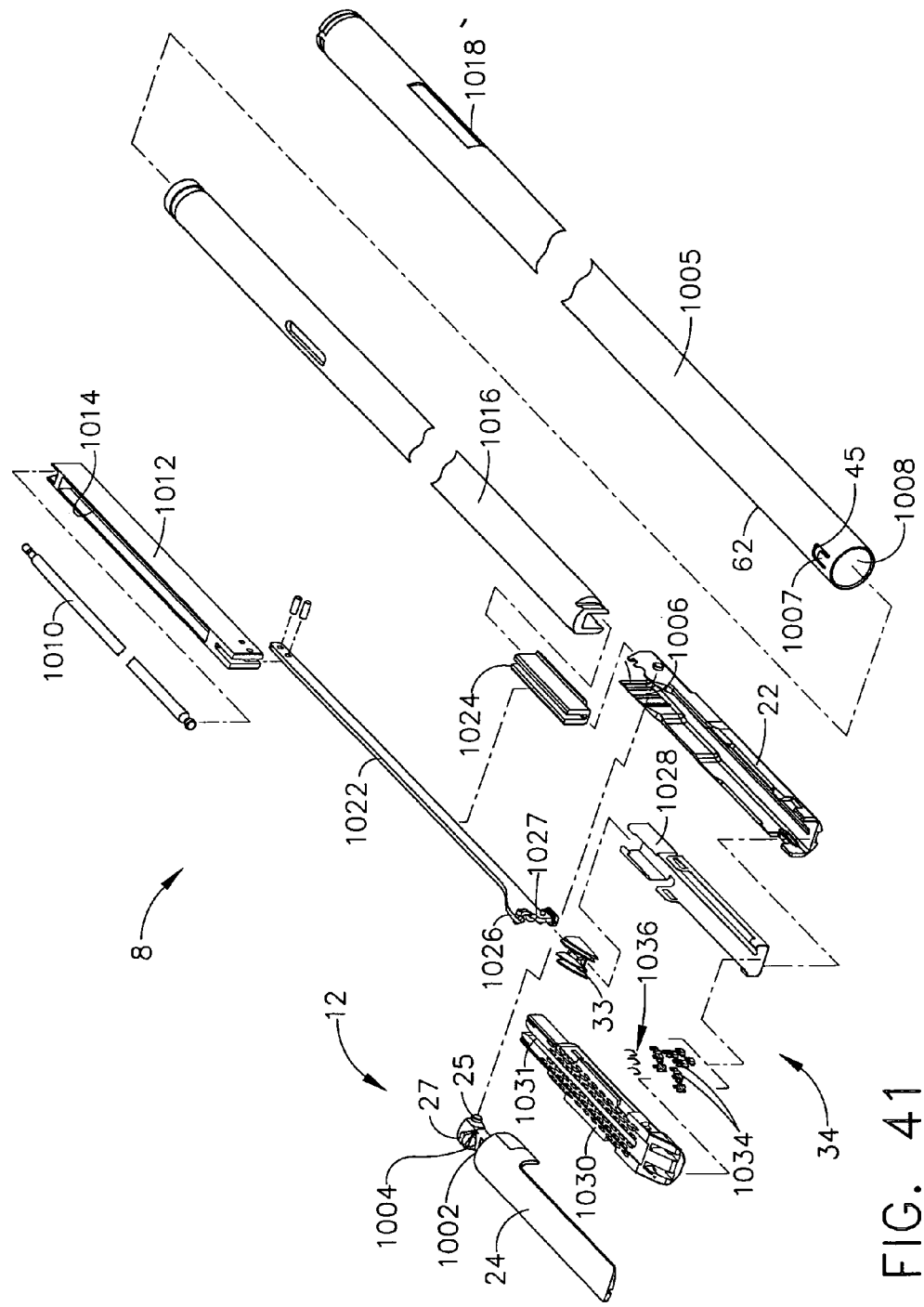
Figure 42:
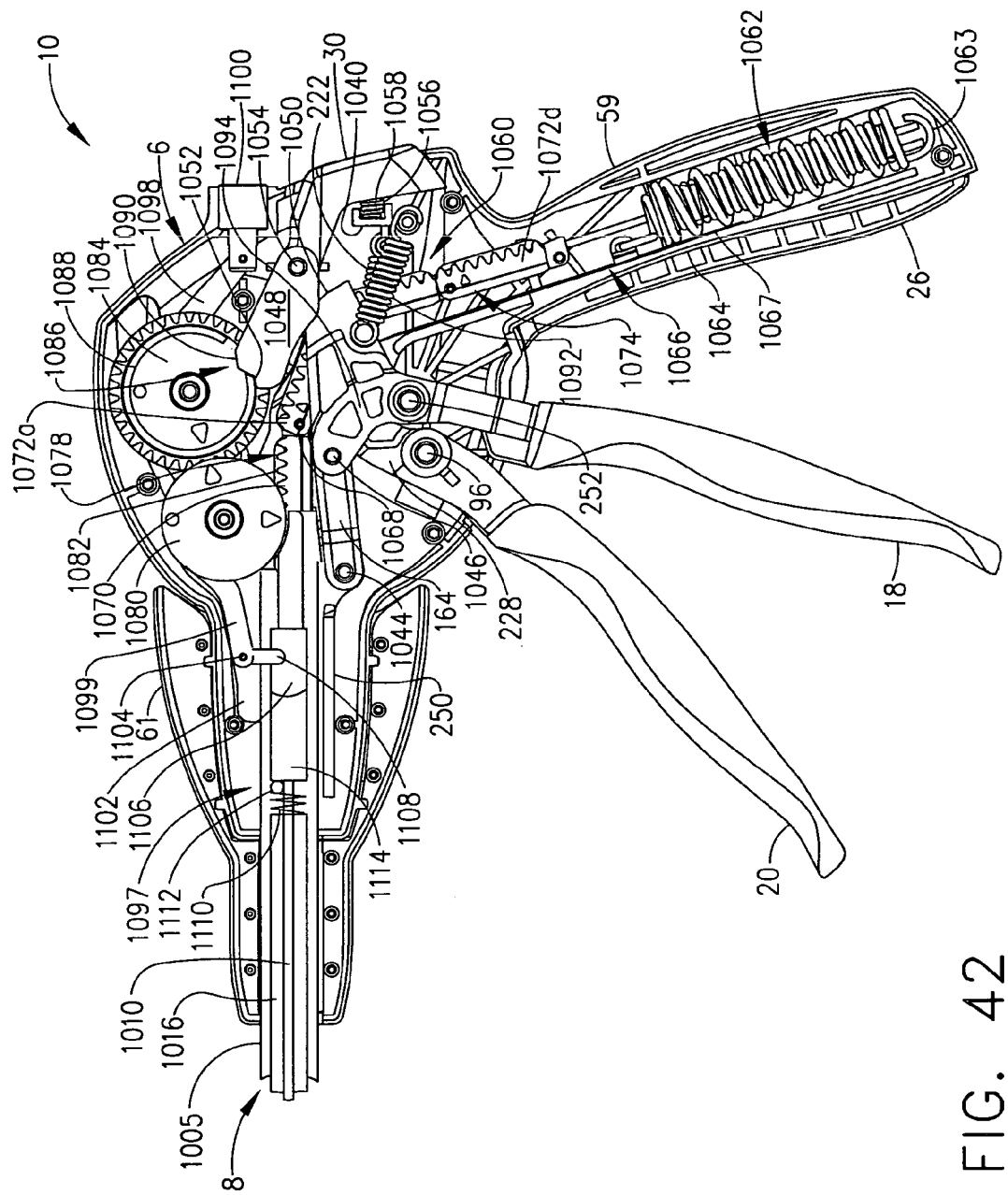
Figure 43:
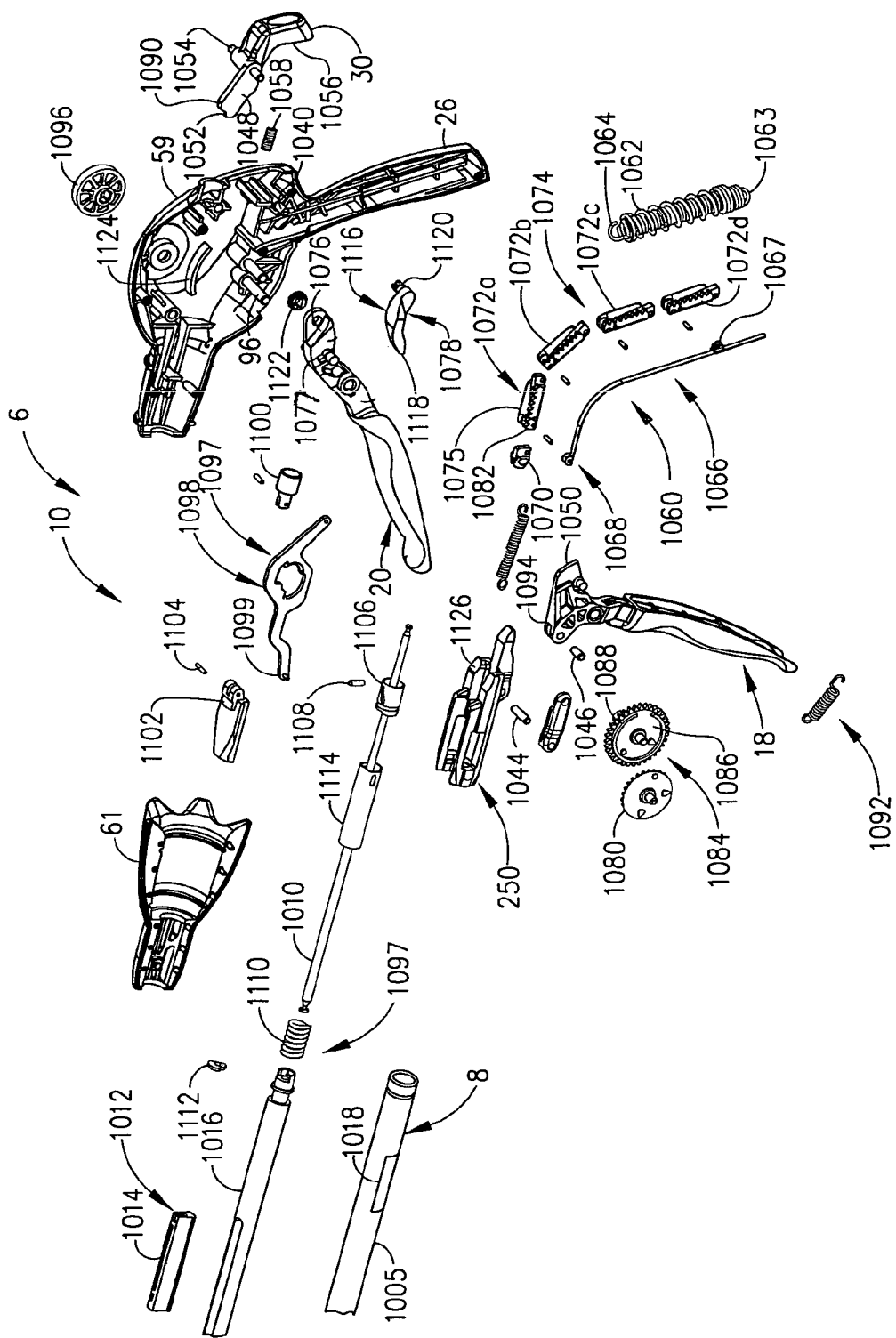
Figure 44:
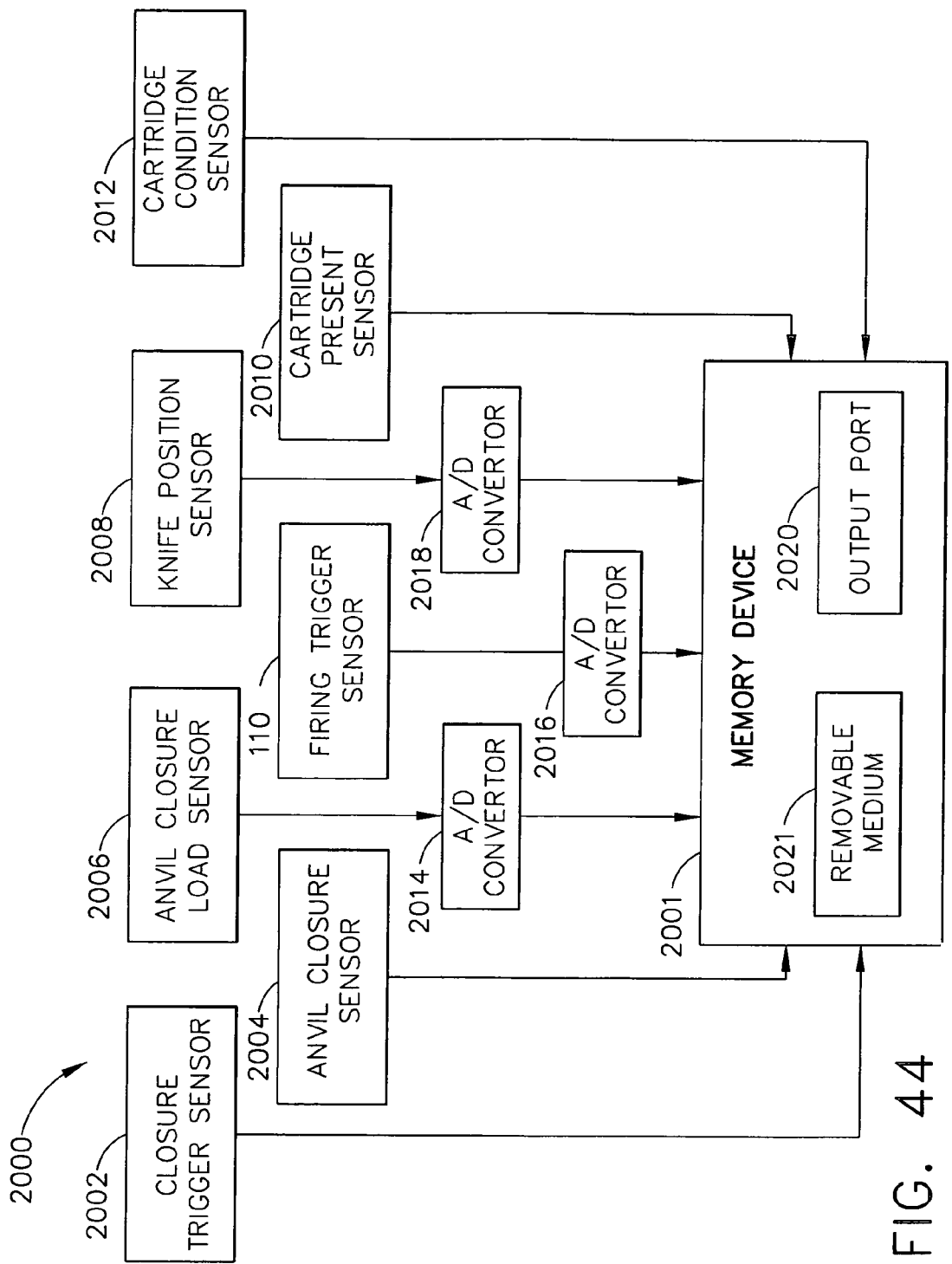
Figure 45:
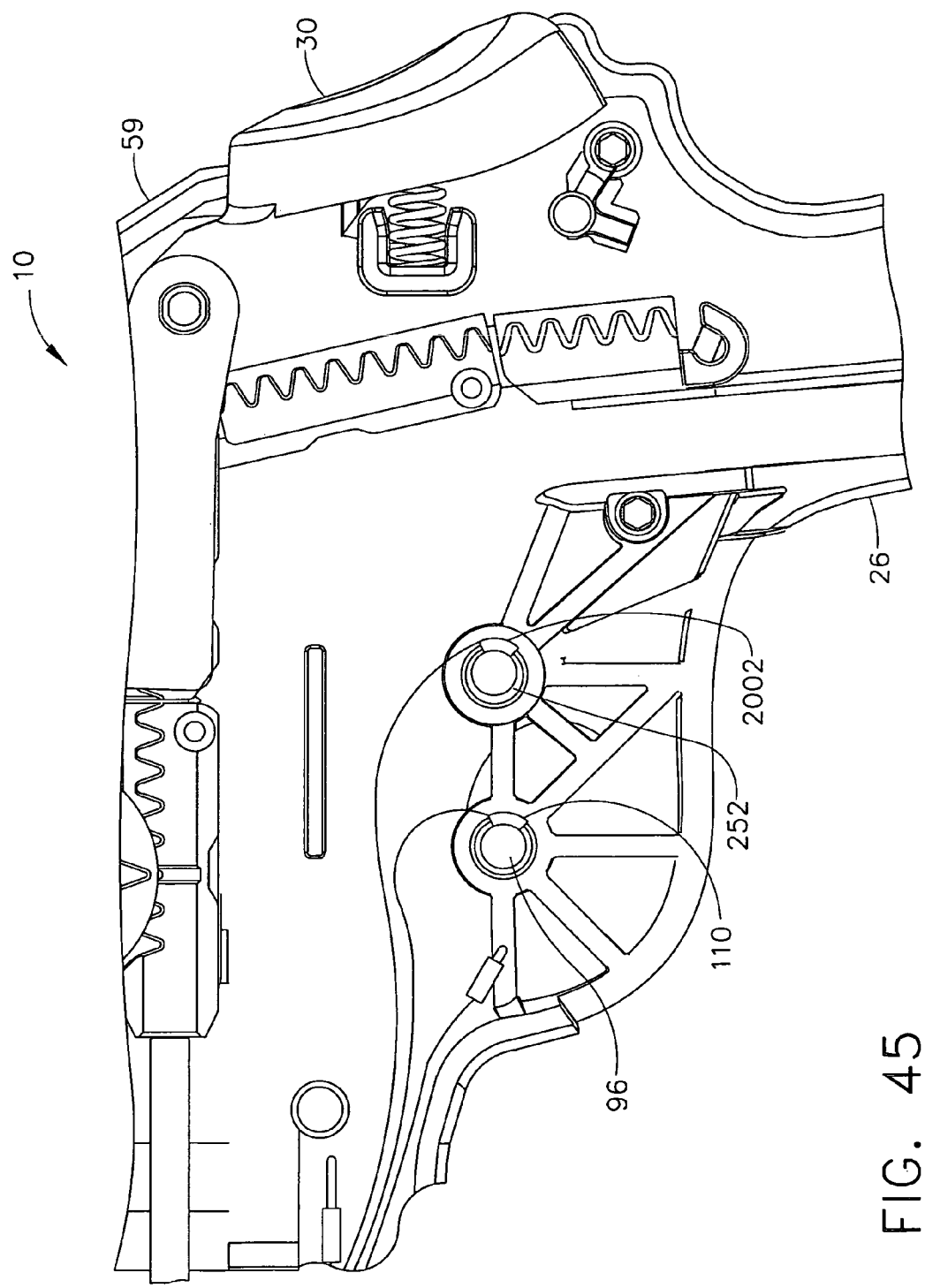
Figure 46:
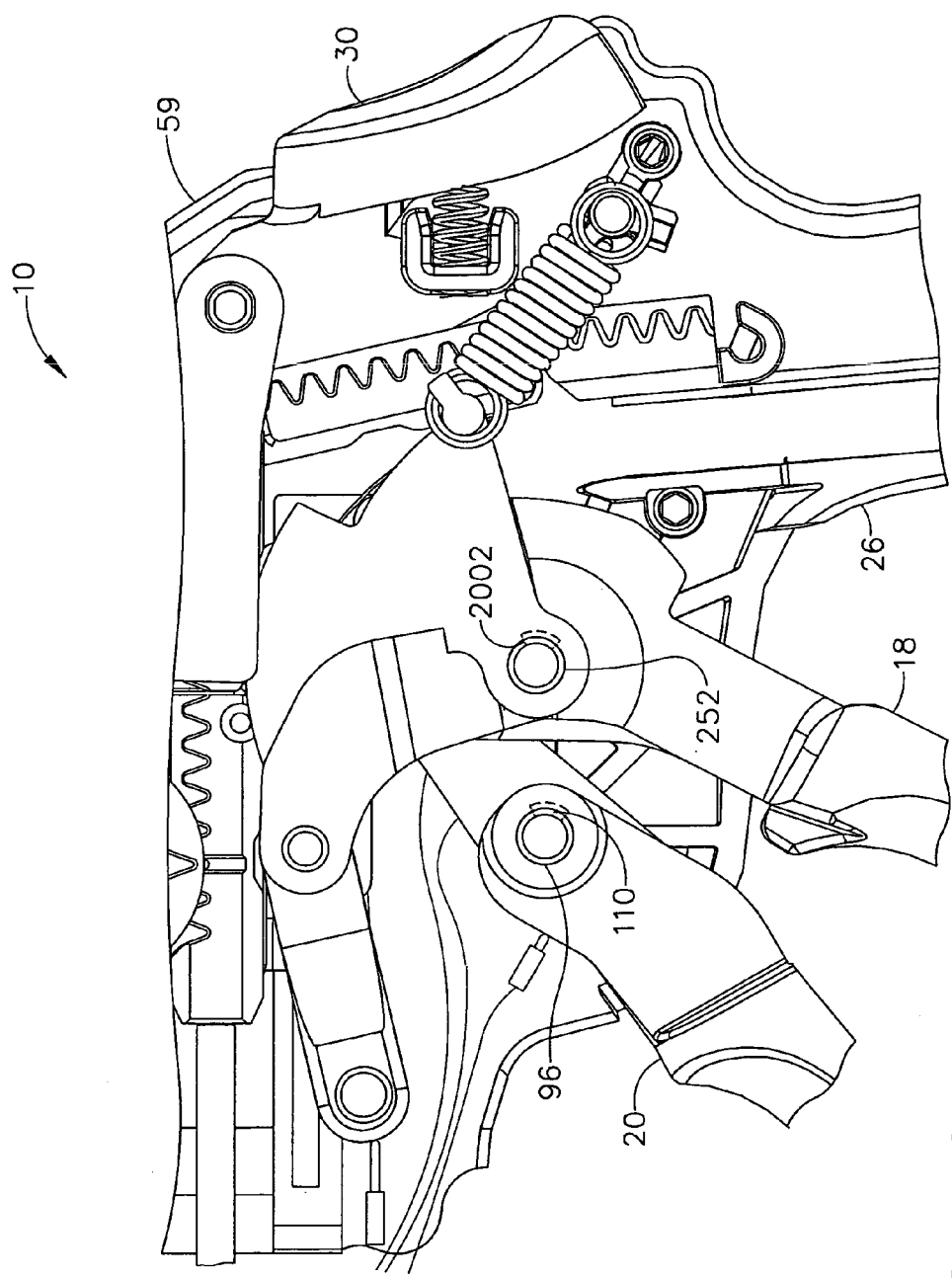
Figure 48:
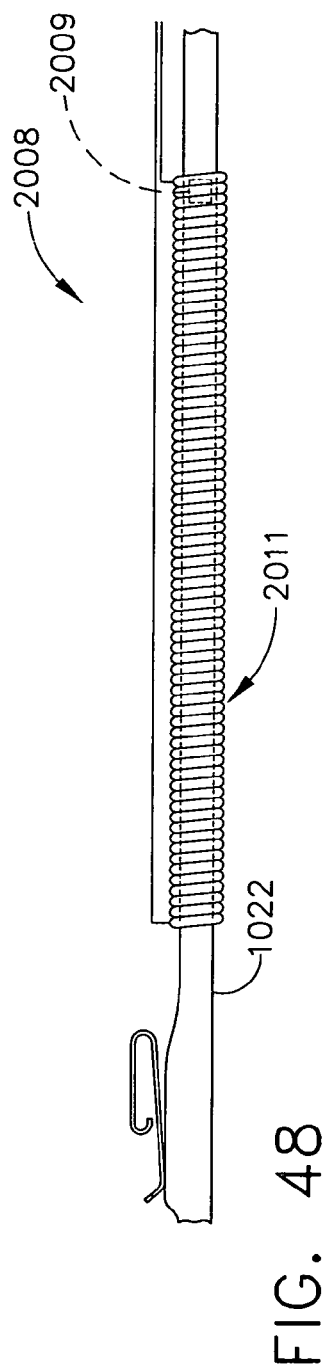
Figure 47:
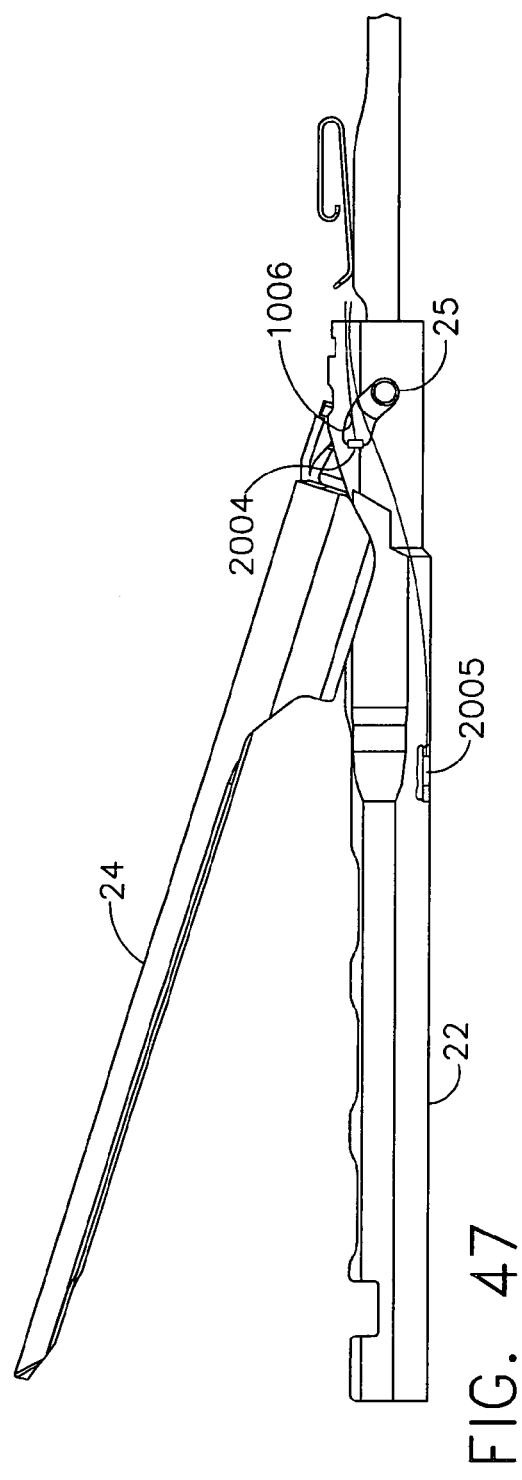
Figure 49:
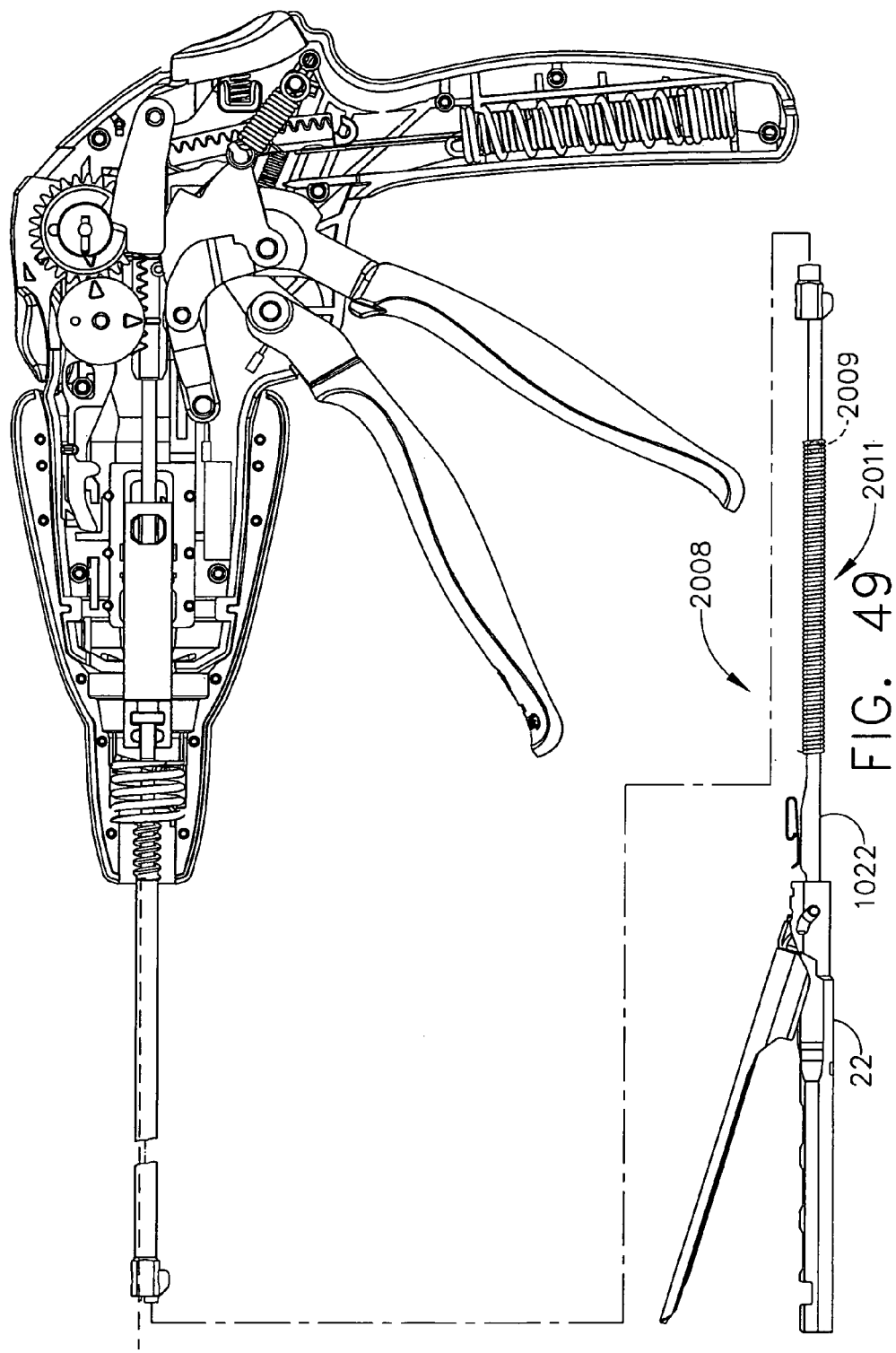
Figure 52A:
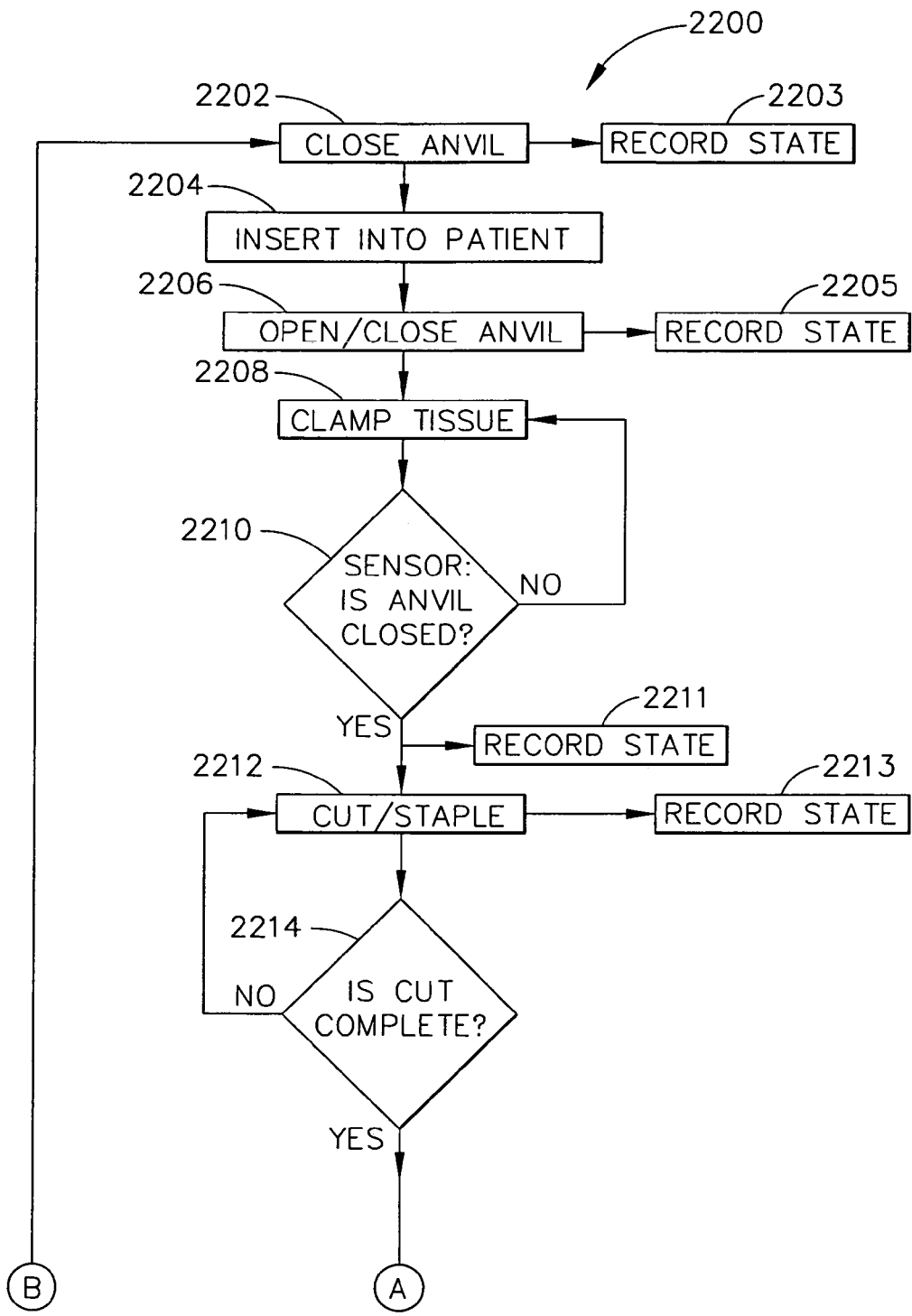
Figure 52B:
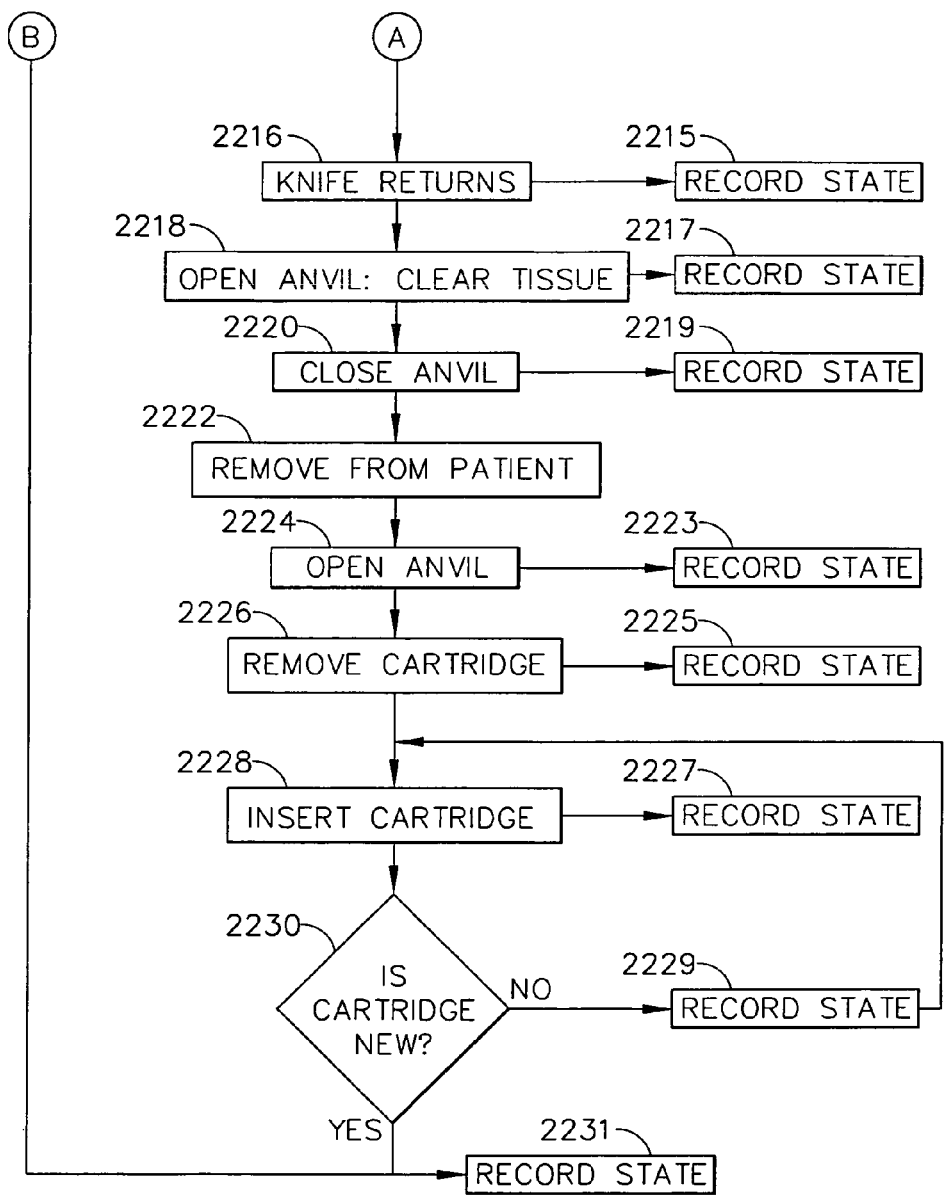
Figure 53:
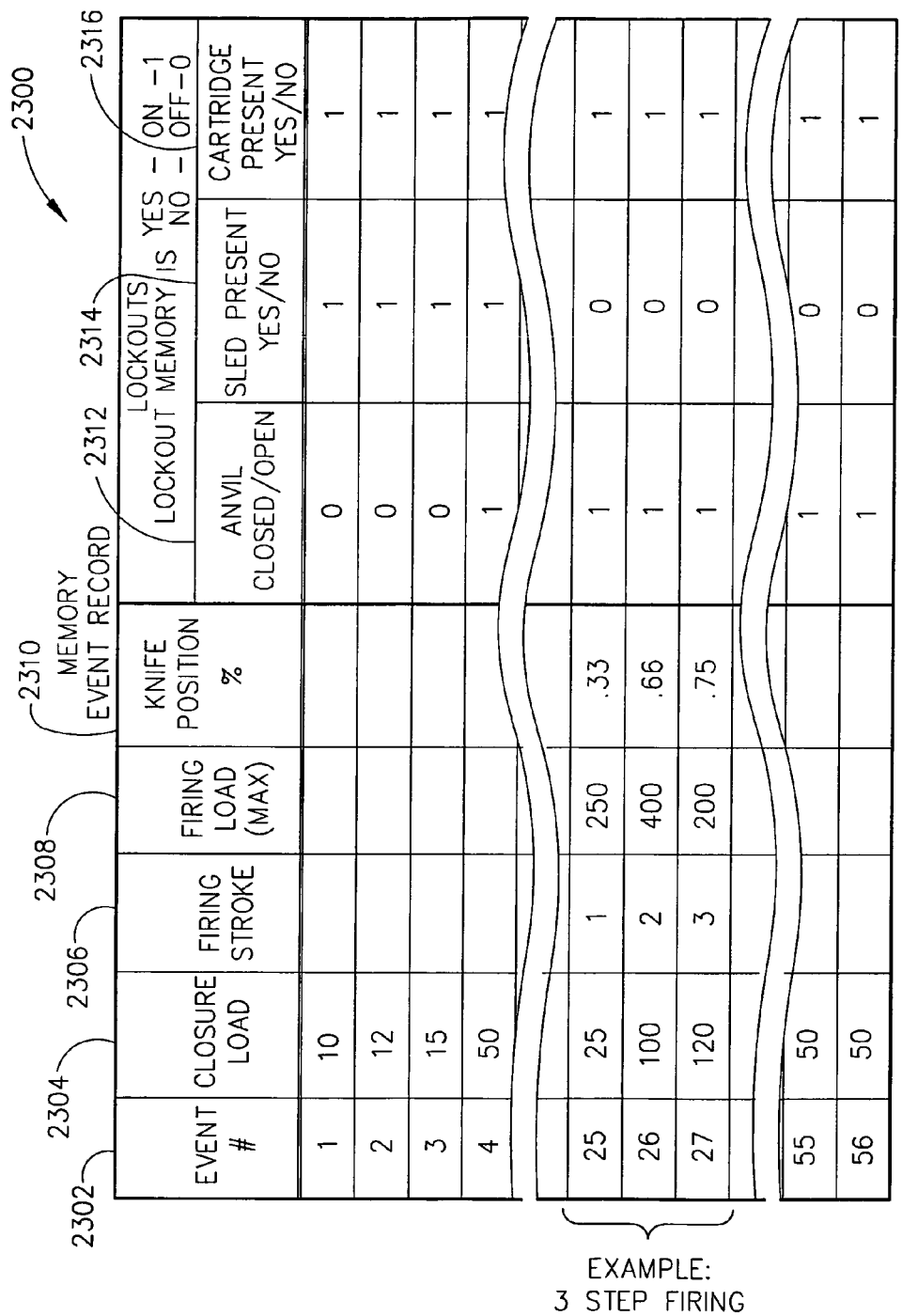

FIGS. 23A-B show a universal joint ("u-joint") that may be employed at the articulation point of the instrument according to various embodiments of the present invention;

FIGS. 24A-B shows a torsion cable that may be employed at the articulation point of the instrument according to various embodiments of the present invention;

FIGS. 25-31 illustrate a surgical cutting and fastening instrument with power assist according to another embodiment of the present invention;

FIGS. 32-36 illustrate a surgical cutting and fastening instrument with power assist according to yet another embodiment of the present invention;

FIGS. 37-40 illustrate a surgical cutting and fastening instrument with tactile feedback to embodiments of the present invention;

FIG. 41 illustrates an exploded view of an end effector and shaft of the instrument according to various embodiments of the present invention;

FIG. 42 illustrates a side view of the handle of a mechanically instrument according to various embodiments of the present invention;

FIG. 43 illustrates an exploded view of the handle of the mechanically actuated instrument of FIG. 42;

FIG. 44 illustrates a block diagram of a recording system for recording various conditions of the instrument according to various embodiments of the present invention;

FIGS. 45-46 illustrate cut away side views of a handle of the instrument showing various sensors according to various embodiments of the present invention;

FIG. 47 illustrates the end effector of the instrument showing various sensors according to various embodiments of the present invention;

FIG. 48 illustrates a firing bar of the instrument including a sensor according to various embodiments of the present invention;

FIG. 49 illustrates a side view of the handle, end effector, and firing bar of the instrument showing a sensor according to various embodiments of the present invention;

FIG. 50 illustrates an exploded view of the staple channel and portions of a staple cartridge of the instrument showing various sensors according to various embodiments of the present invention;

FIG. 51 illustrates a top down view of the staple channel of the instrument showing various sensors according to various embodiments of the present invention;

FIGS. 52A and 52B illustrate a flow chart showing a method for operating the instrument according to various embodiments; and FIG. 53 illustrates a memory chart showing exemplary recorded conditions of the instrument according to various embodiments of the present invention.

DETAILED DESCRIPTION

Figure 1:
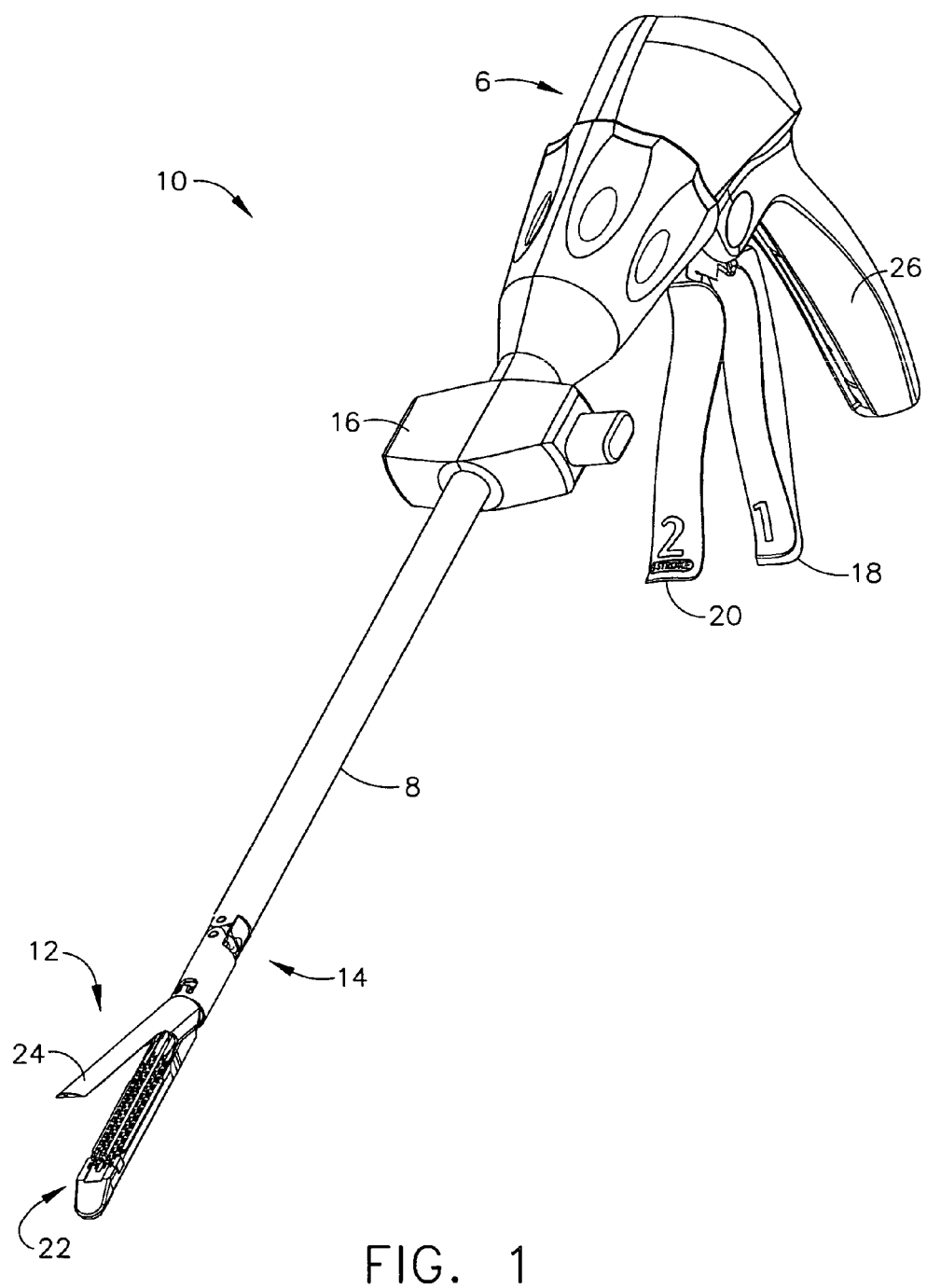
Figure 2:
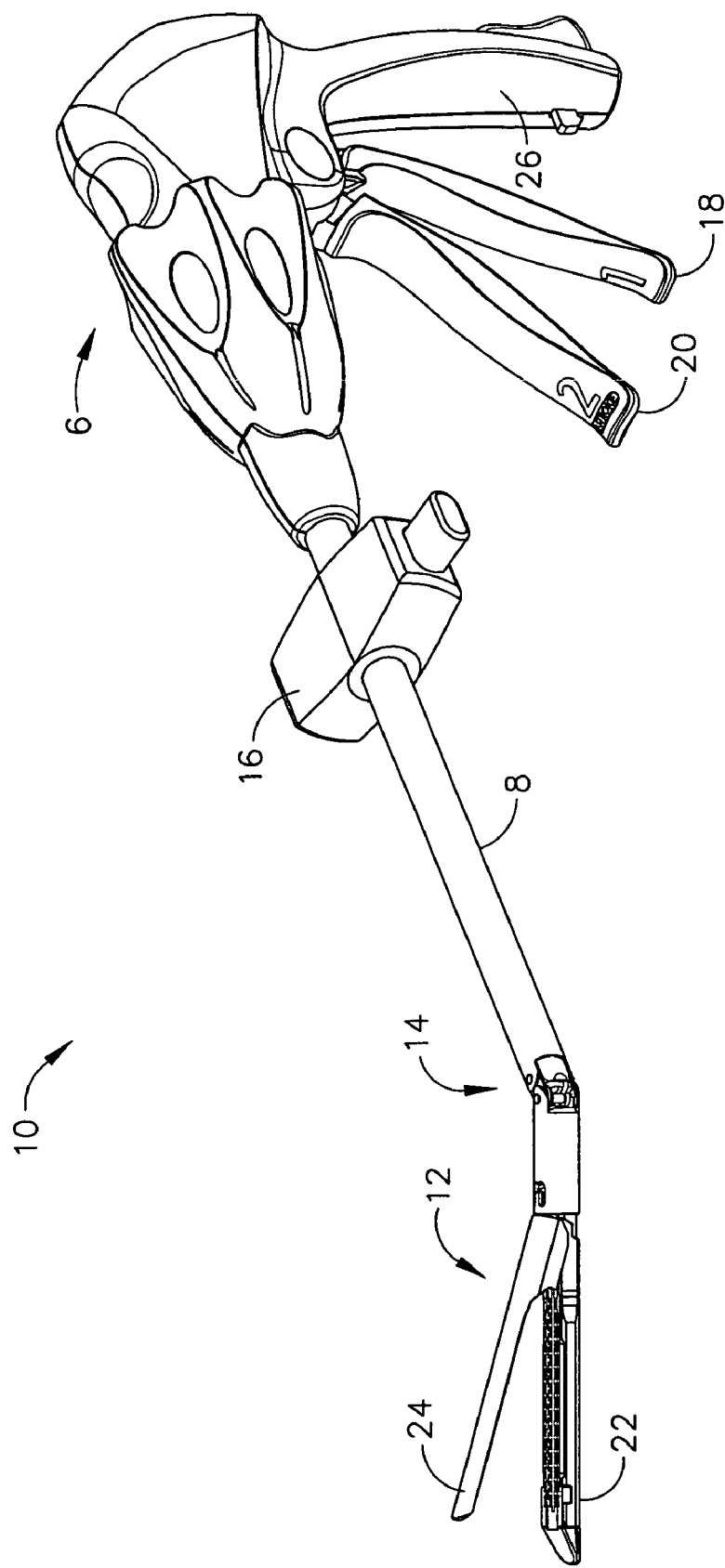

FIGS. 1 and 2 depict a surgical cutting and fastening instrument 10 according to various embodiments of the present invention. The illustrated embodiment is an endoscopic surgical instrument 10 and in general, the embodiments of the instrument 10 described herein are endoscopic surgical cutting and fastening instruments. It should be noted, however, that according to other embodiments of the present invention, the instrument 10 may be a non-endoscopic surgical cutting instrument, such as a laproscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. It will be appreciated that various embodiments may include a non-pivoting end effector, and therefore may not have an articulation pivot 14 or articulation control 16. Also, in the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 towards the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, release button 30 shown in FIGS. 42-43, slide release button 160 shown in FIG. 14, and/or button 172 shown in FIG. 16.

Figure 3:
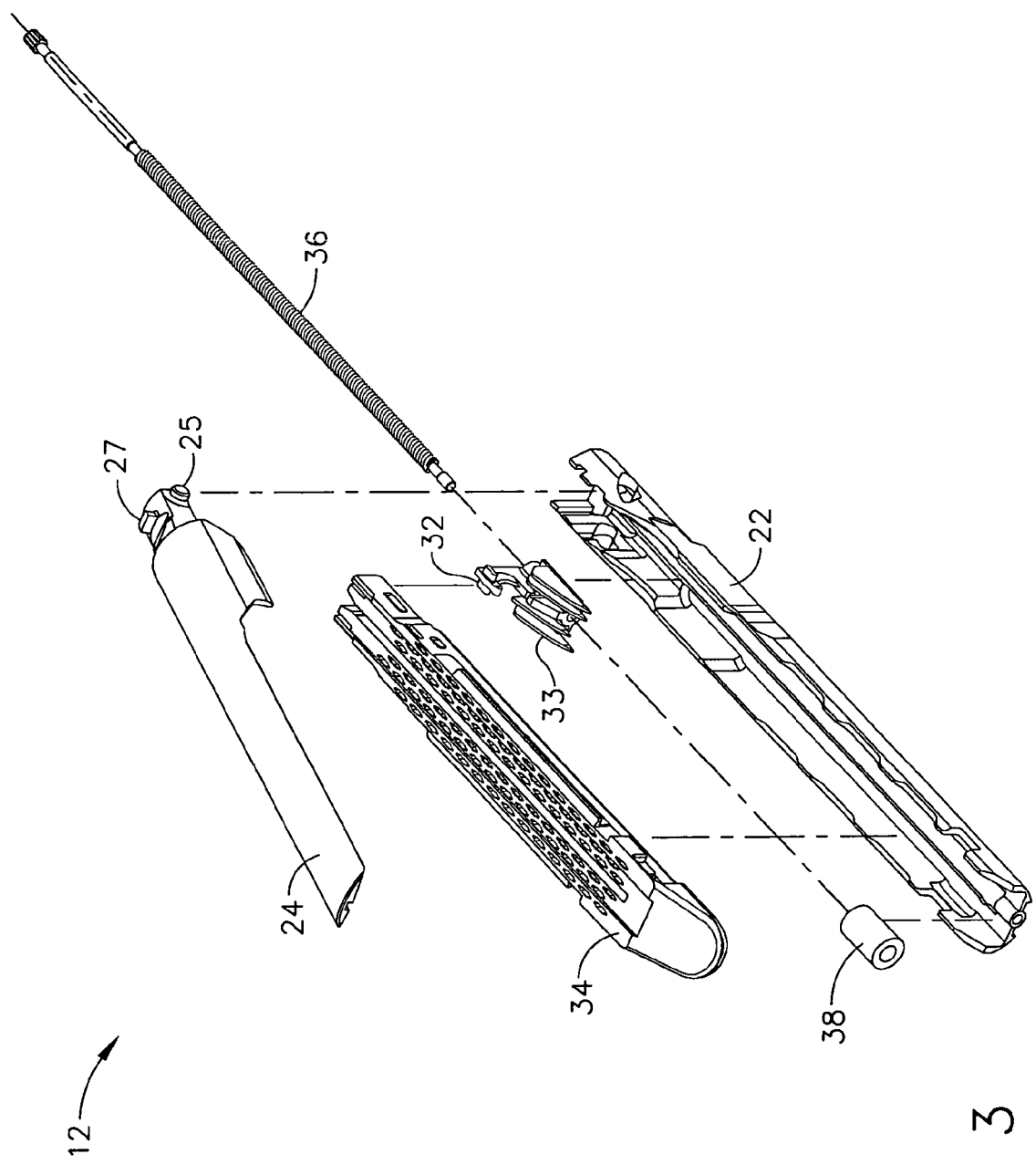
FIGS. 3-5 are exploded views of an end effector and shaft of the instrument according to various embodiments of the present invention.

FIGS. 3-6 show embodiments of a rotary-driven end effector 12 and shaft 8 according to various embodiments. FIG. 3 is an exploded view of the end effector 12 according to various embodiments A shown in the illustrated embodiment the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at pivot pins 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot pins 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples (not shown) of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "SURGICAL STAPLING INSTRUMENT INCORPORATING AN E-BEAM FIRING MECHANISM" to Shelton, IV et al., which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTROSURGICAL HEMOSTATIC DEVICE WITH RECESSED AND/OR OFFSET ELECTRODES" to Yates et al. which are incorporated herein by reference, disclose an endoscopic cutting instrument that uses RF energy to seal the severed tissue. U.S. patent application Ser. No. 11/267,811 to Jerome R. Morgan, et. al, and U.S. patent application Ser. No. 11/267,383 to Frederick E. Shelton, IV, et. al, which are also incorporated herein by reference, disclose cutting instruments that uses adhesives to fasten the severed tissue. Accordingly, although the description herein refers to cutting/stapling operations and the like below, it should be recognized that this is an exemplary embodiment and is not meant to be limiting. Other tissue fastening techniques may also be used.

Figure 4:
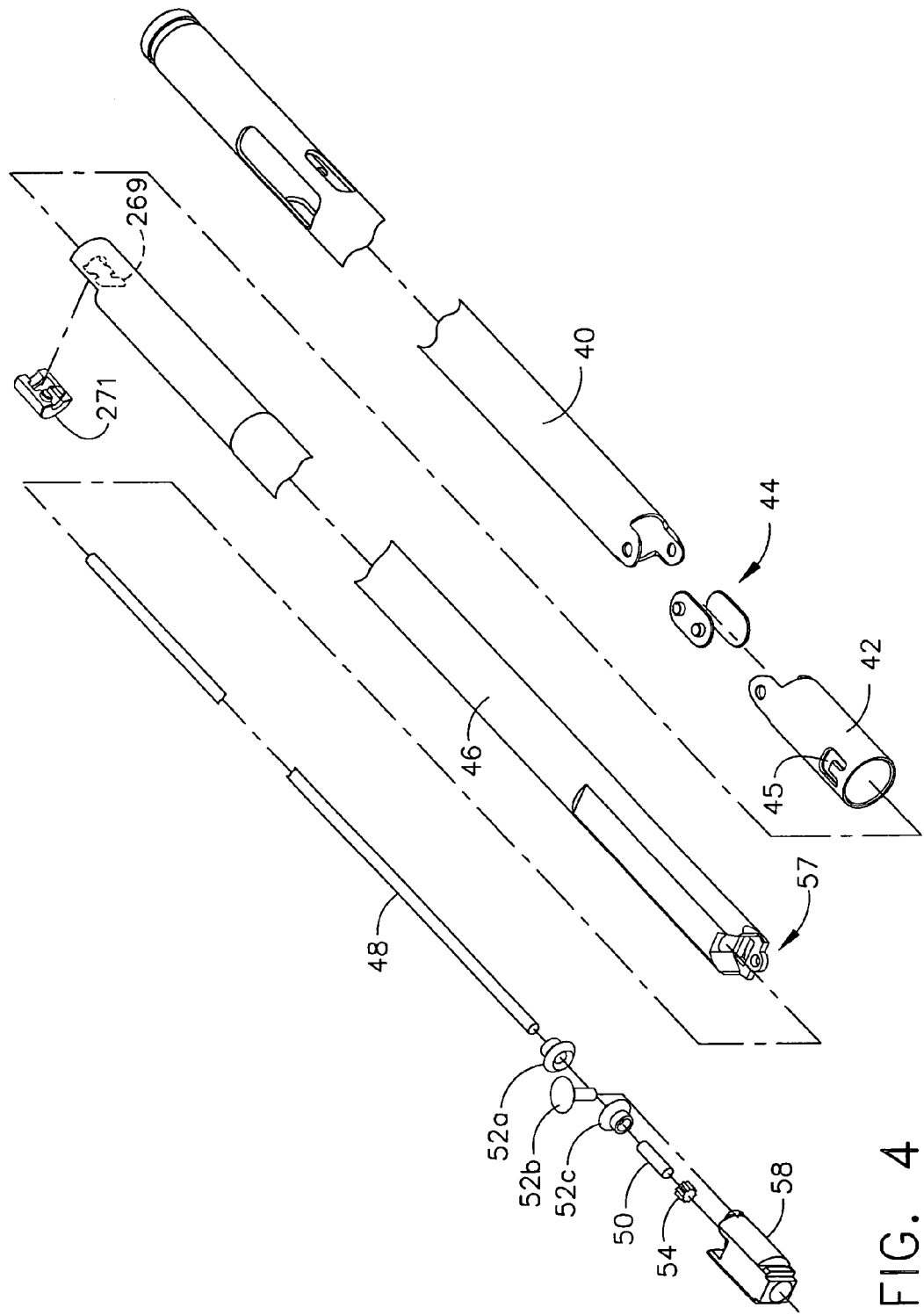
Figure 5:
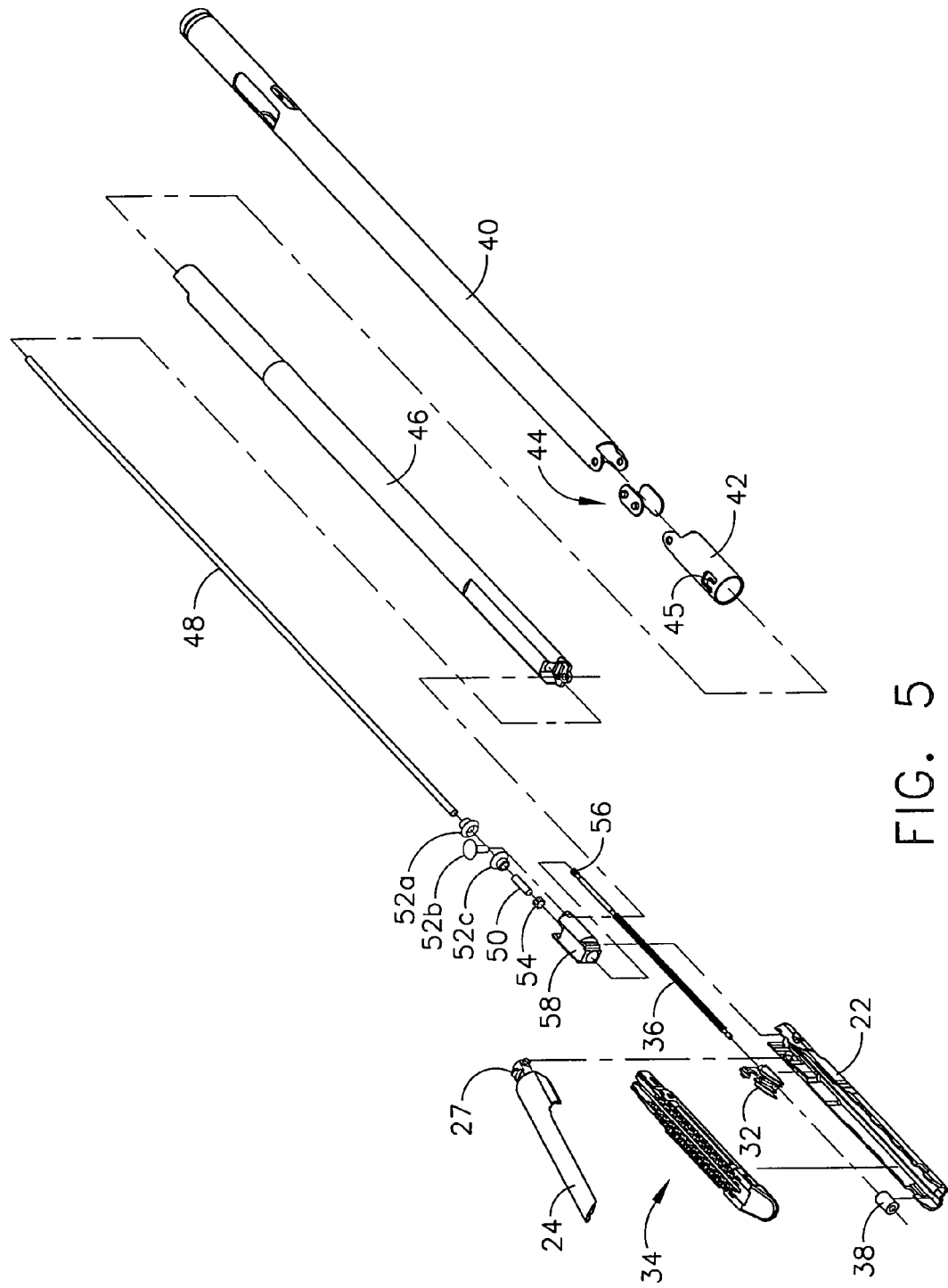
Figure 6:
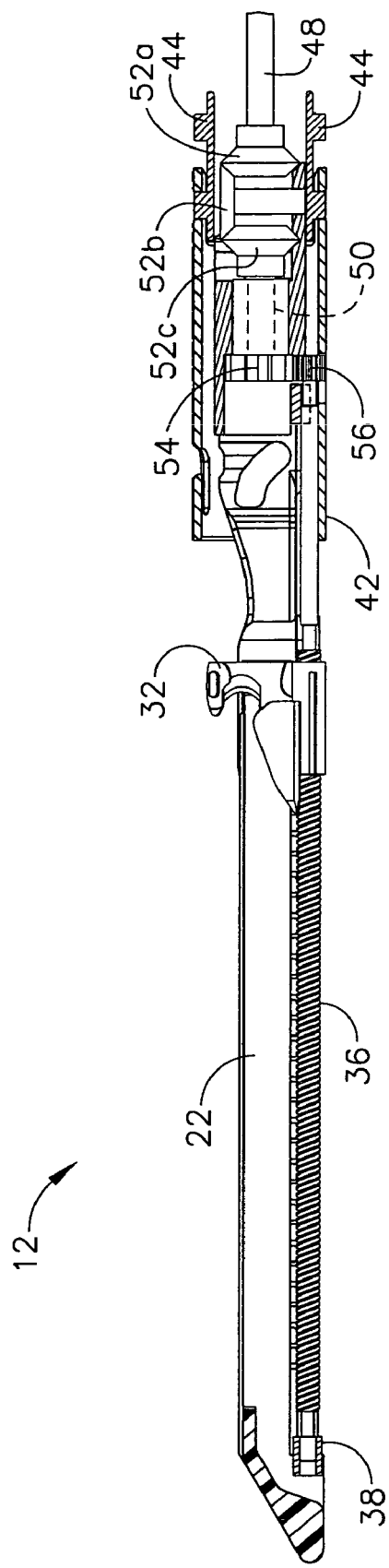
FIG. 6 is a side view of the end effector according to various embodiments of the present invention.
Figure 7:
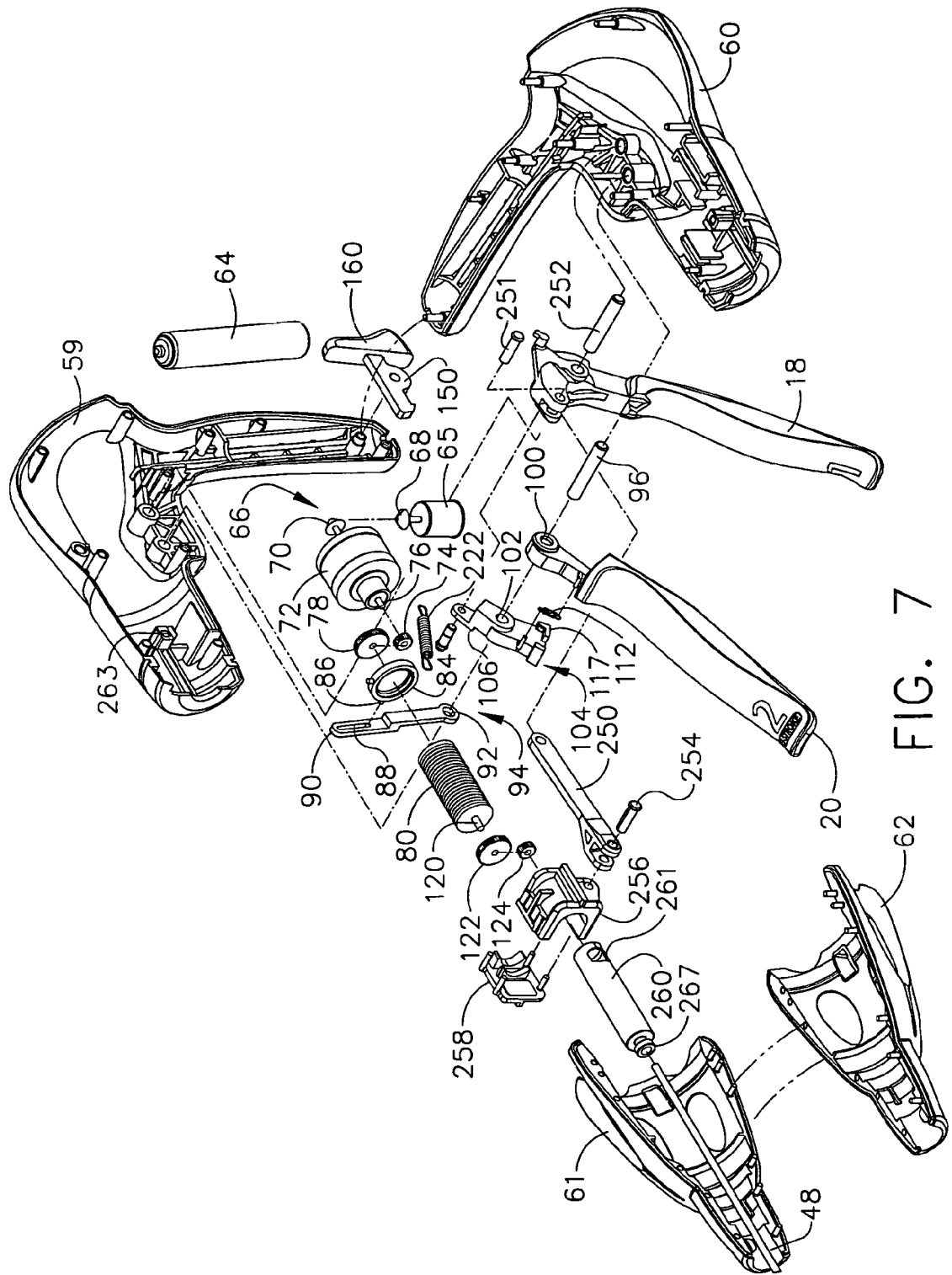
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot link 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector 12. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

As described above, because of the lack of user feedback for the cutting/stapling operation, there is a general lack of acceptance among physicians of motor-driven endocutters where the cutting/stapling operation is actuated by merely pressing a button. In contrast, embodiments of the present invention provide a motor-driven endocutter with user-feedback of the deployment, force and/or position of the cutting instrument 32 in end effector 12.

FIGS. 7-10 illustrate an exemplary embodiment of a motor-driven endocutter, and in particular the handle thereof, that provides user-feedback regarding the deployment and loading force of the cutting instrument 32 in the end effector 12. In addition, the embodiment may use power provided by the user in retracting the firing trigger 20 to power the device (a so-called "power assist" mode). The embodiment may be used with the rotary driven end effector 12 and shaft 8 embodiments described above. As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 (see FIG. 10) in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor sensor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65, for example, at a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector 12 is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
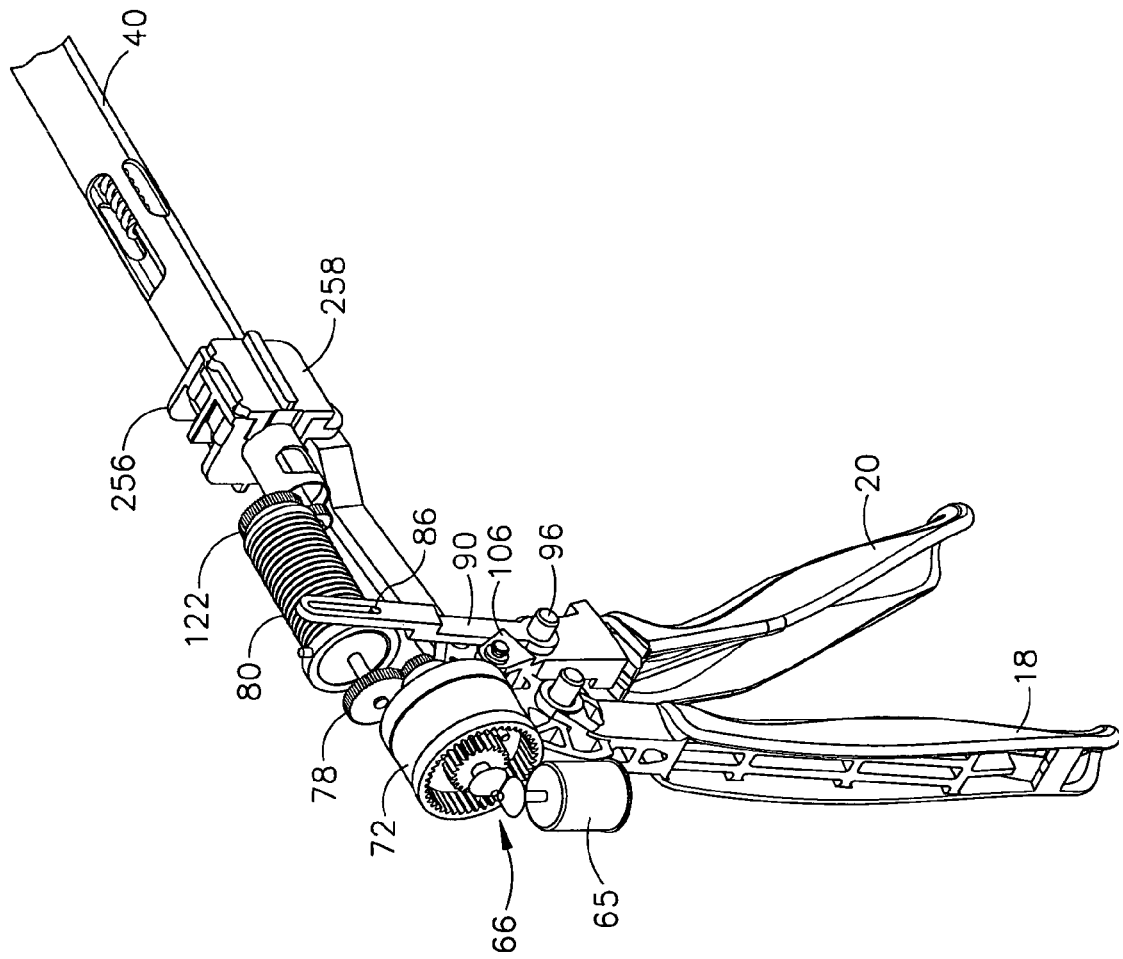
FIGS. 8 and 9 are partial perspective views of the handle according to various embodiments of the present invention.
Figure 9:
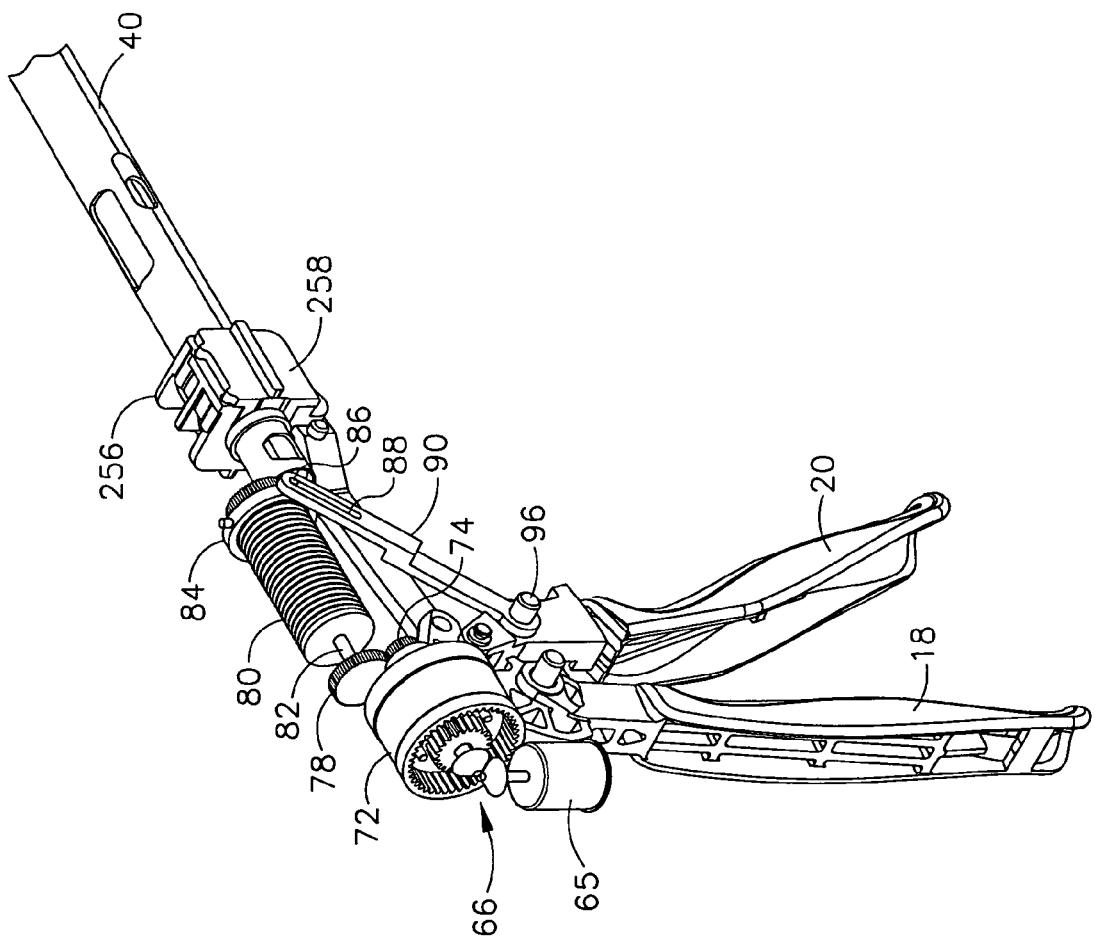

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates counter clockwise as the ring 84 travels from the proximate end of the helical gear drum 80 to the distal end, the middle handle piece 104 will be free to rotate counter clockwise. Thus, as the user draws in the firing trigger 20, the firing trigger 20 will engage the forward motion stop 107 of the middle handle piece 104, causing the middle handle piece 104 to rotate counter clockwise. Due to the backside shoulder 106 engaging the slotted arm 90, however, the middle handle piece 104 will only be able to rotate counter clockwise as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate counter clockwise due to the slotted arm 90.

Figure 10:
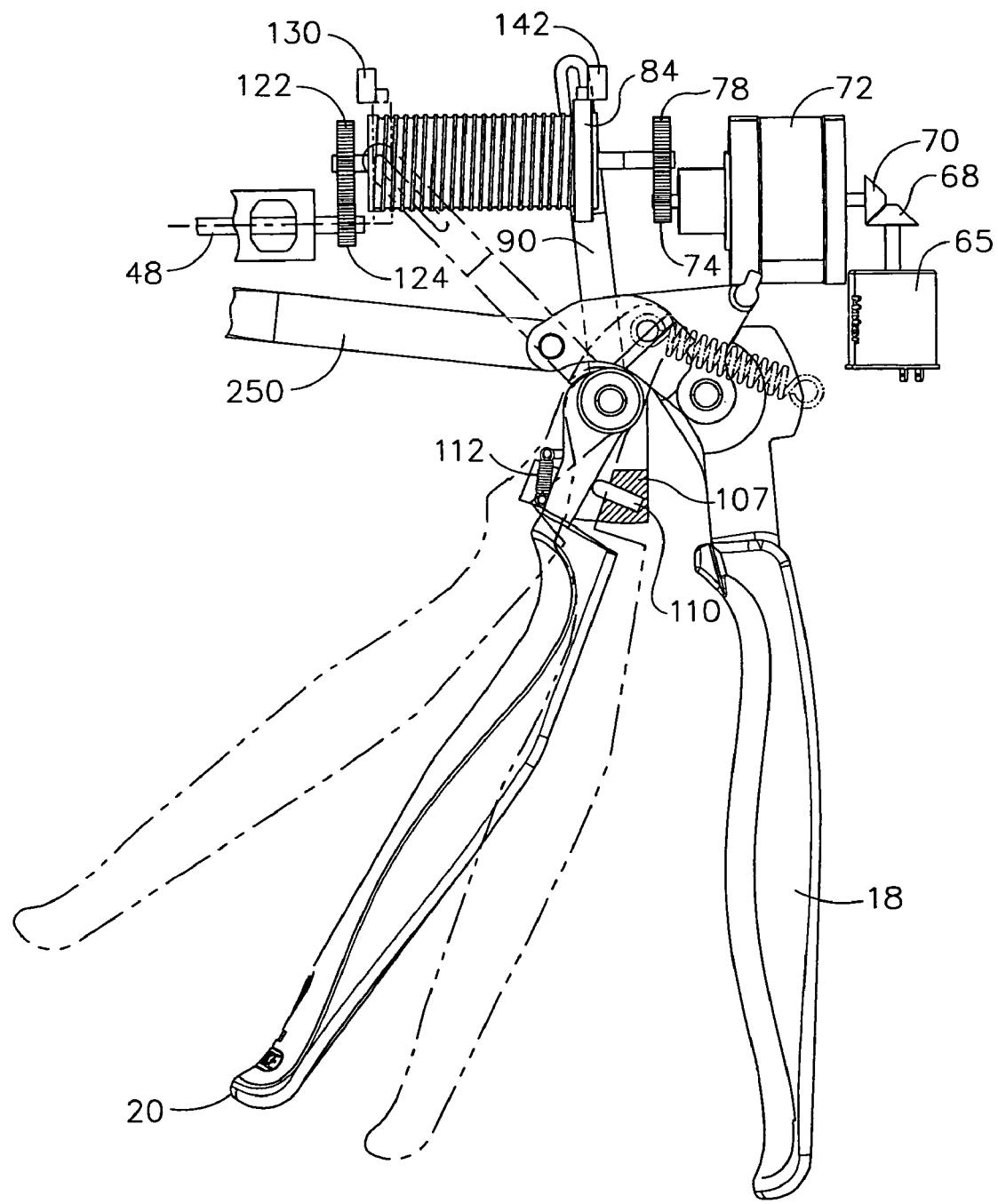
FIG. 10 is a side view of the handle according to various embodiments of the present invention.
Figure 10A:
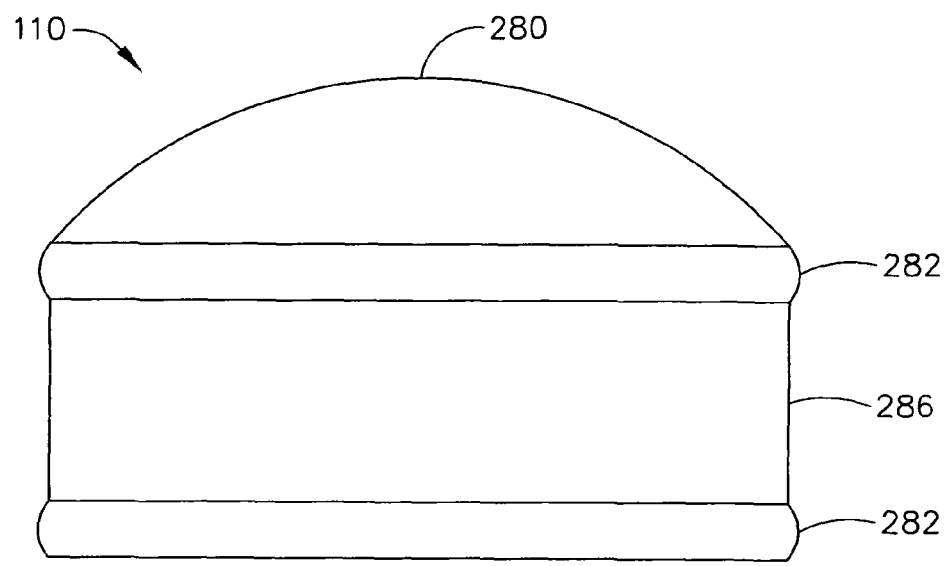
FIGS. 10A and 10B illustrate a proportional sensor that maybe used according to various embodiments of the present invention.
Figure 10B:
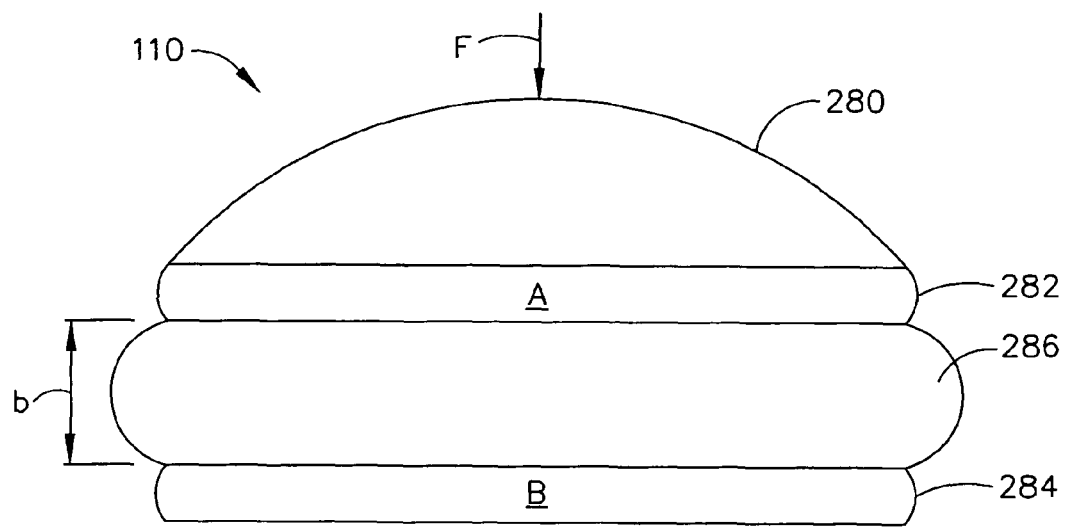

FIGS. 10A and 10B illustrate two states of a variable sensor that may be used as the run motor sensor 110 according to various embodiments of the present invention. The sensor 110 may include a face portion 280, a first electrode (A) 282, a second electrode (B) 284, and a compressible dielectric material 286 between the electrodes 282, 284, such as, for example, an electoactive polymer (EAP). The sensor 110 may be positioned such that the face portion 280 contacts the firing trigger 20 when retracted. Accordingly, when the firing trigger 20 is retracted, the dielectric material 286 is compressed, as shown in FIG. 10B, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pivot pin 251 inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate counterclockwise. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot pins 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot pins 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
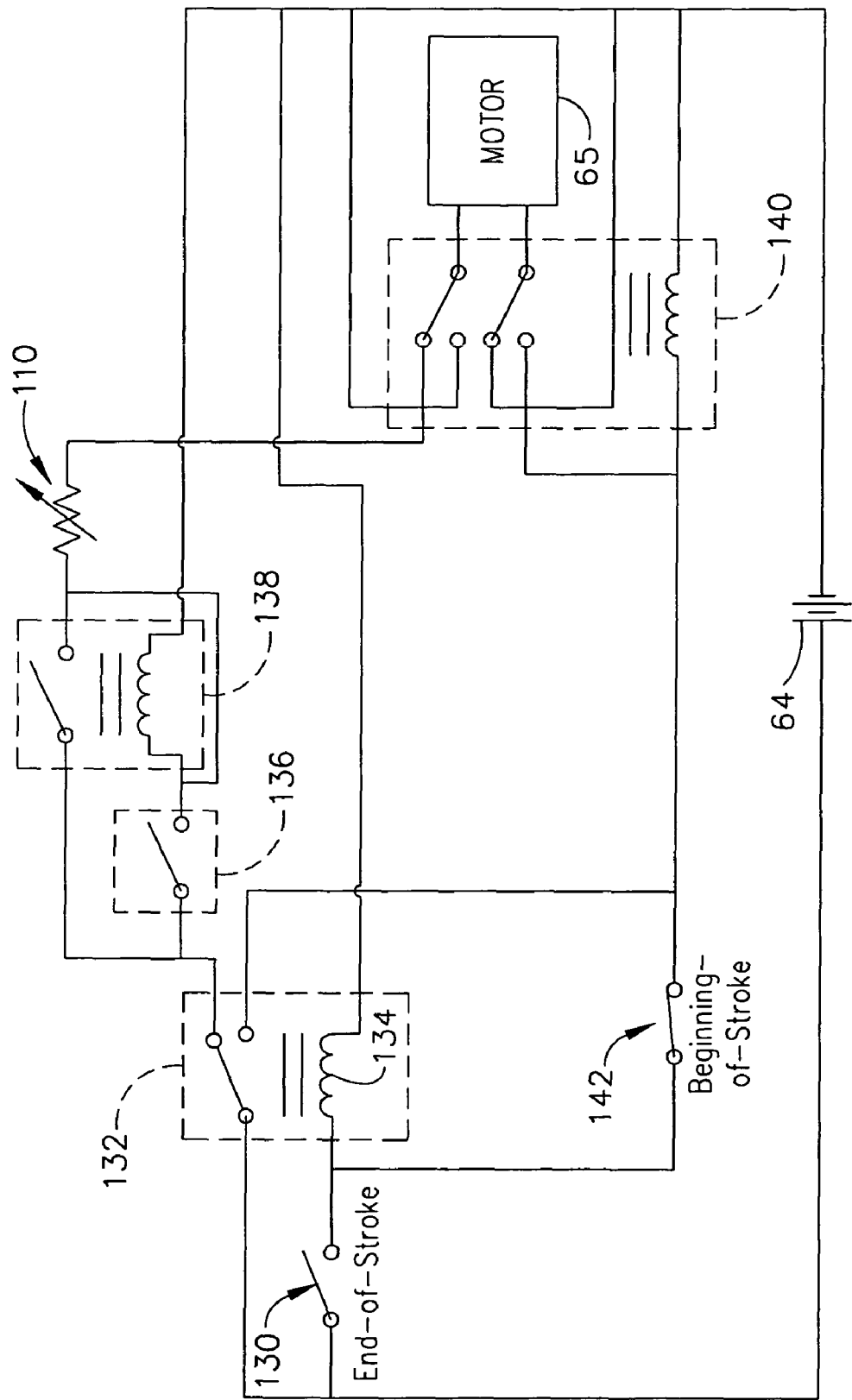
FIG. 11 is a schematic diagram of a circuit used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
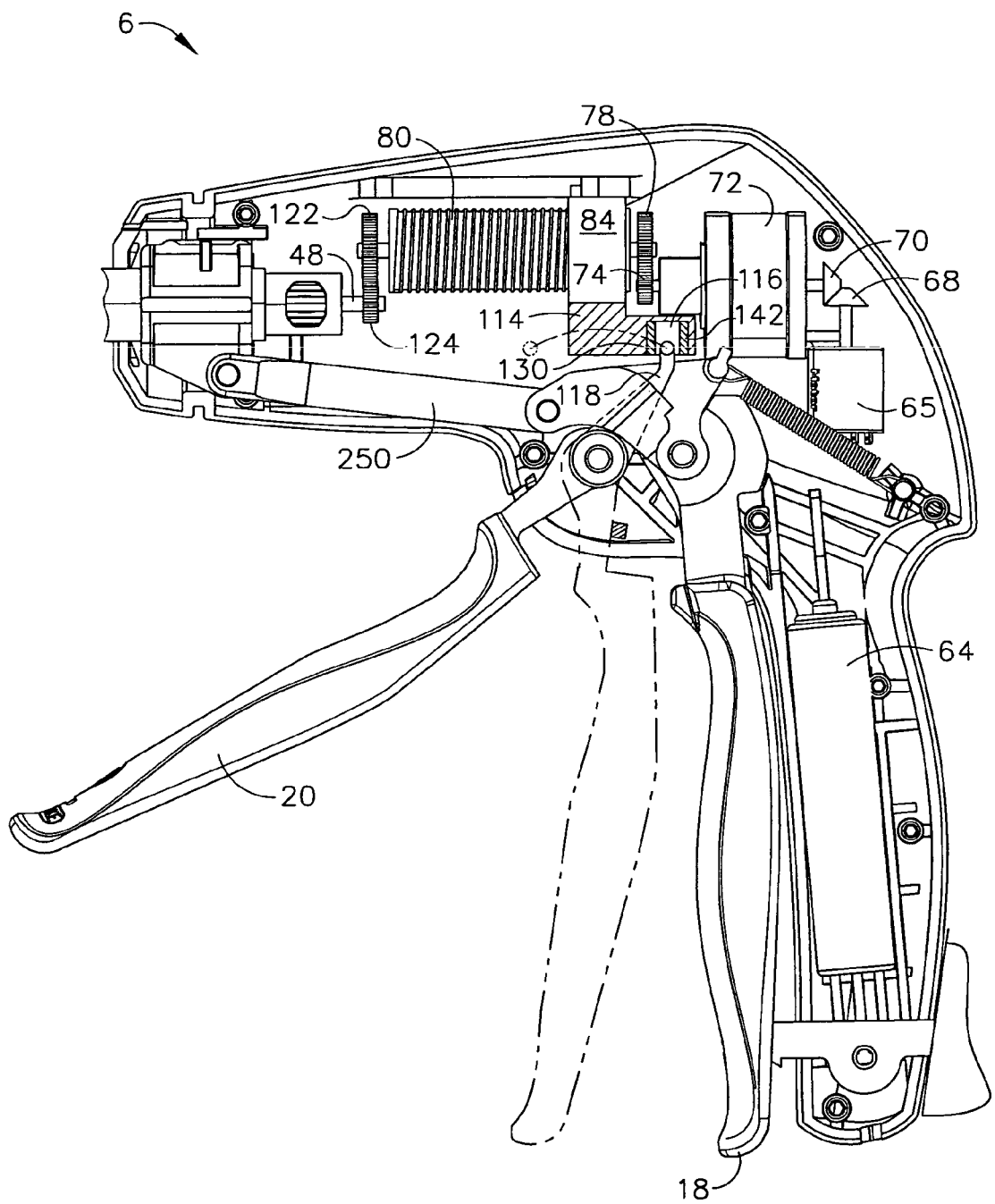
FIGS. 12-13 are side views of the handle according to other embodiments of the present invention.

FIG. 12 is a side-view of the handle 6 of a power-assist motorized endocutter according to another embodiment. The embodiment of FIG. 12 is similar to that of FIGS. 7-10 except that in the embodiment of FIG. 12, there is no slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate counter clockwise with the firing trigger 20 due to the forward motion stop 107 that engages the firing trigger 20. The counter clockwise rotation of the middle piece 104 cause the arm 118 to rotate counter clockwise with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm will contact and thereby trip the stop motor sensor 142. Such actions may reverse and stop the motor 65, respectively as described above.

Figure 13:
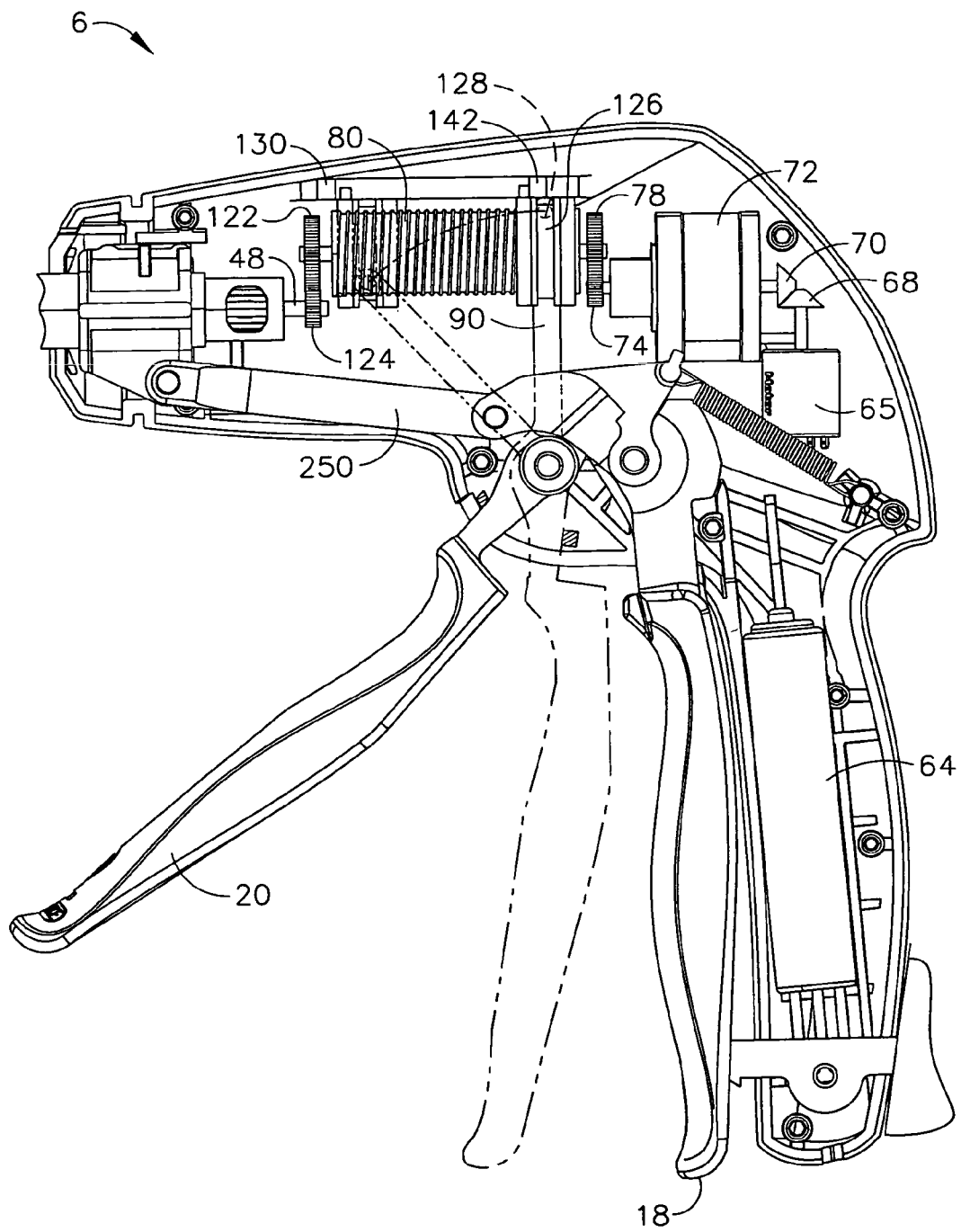

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90 Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates counter clockwise as the ring 84 advances due to the post 128 being disposed in the channel 126, as shown in FIG. 13.

Figure 14:
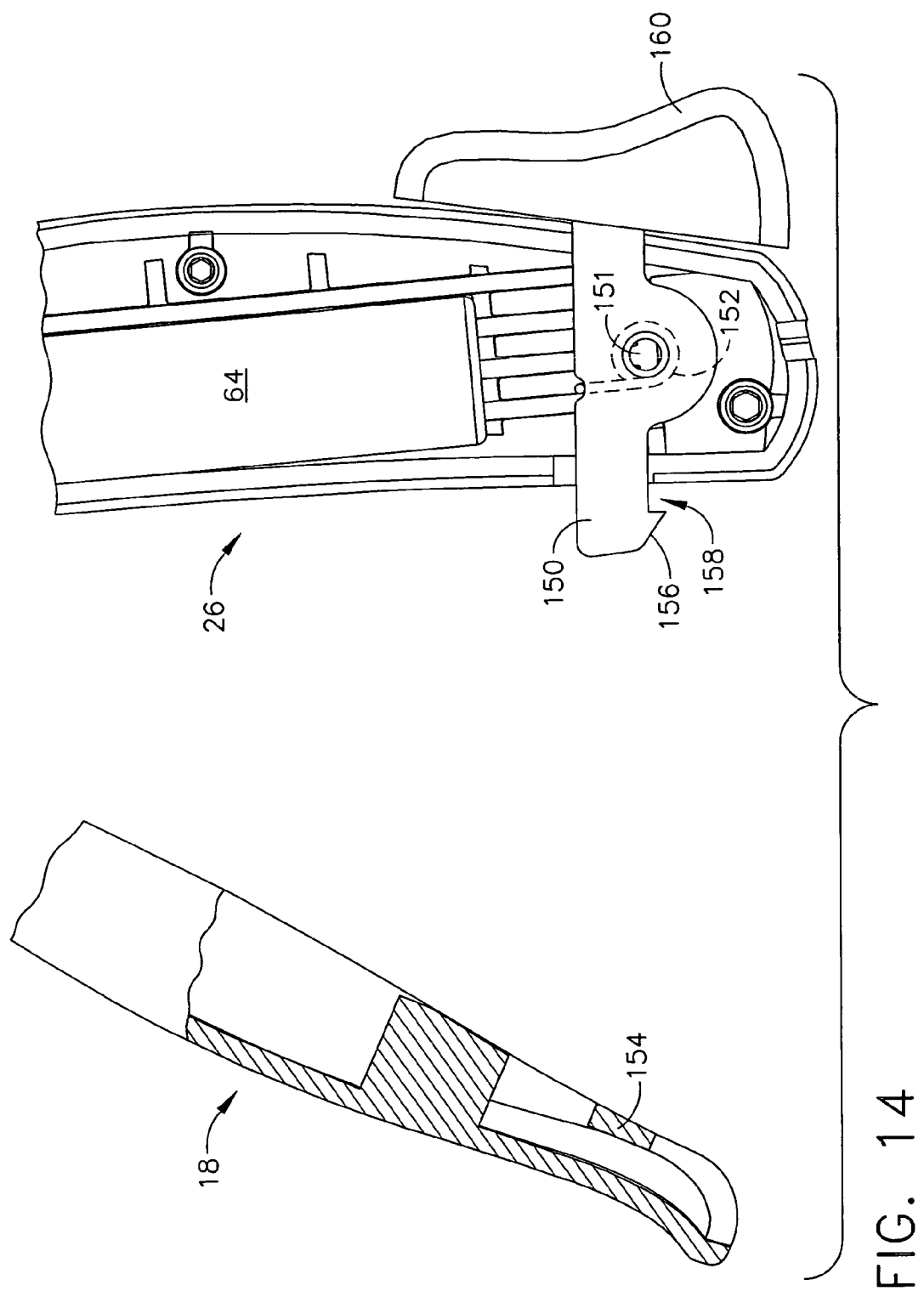
FIGS. 14-22 illustrate different mechanisms for locking the closure trigger according to various embodiments of the present invention.
Figure 15:
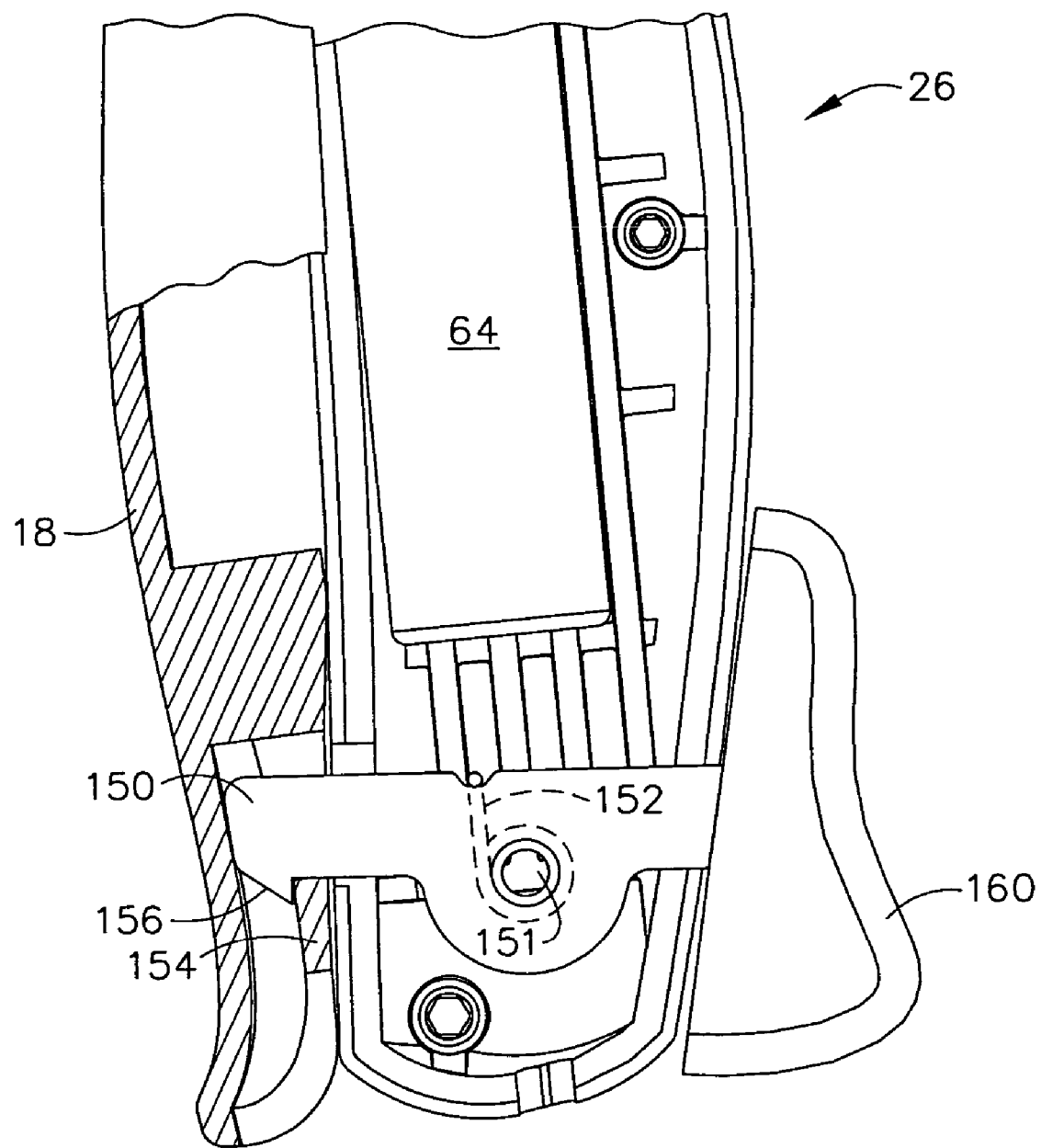

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate counter clockwise about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or clockwise in FIGS. 14-15) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 clockwise such that the closure bar 154 is released from the recessed notch 158.

Figure 16:
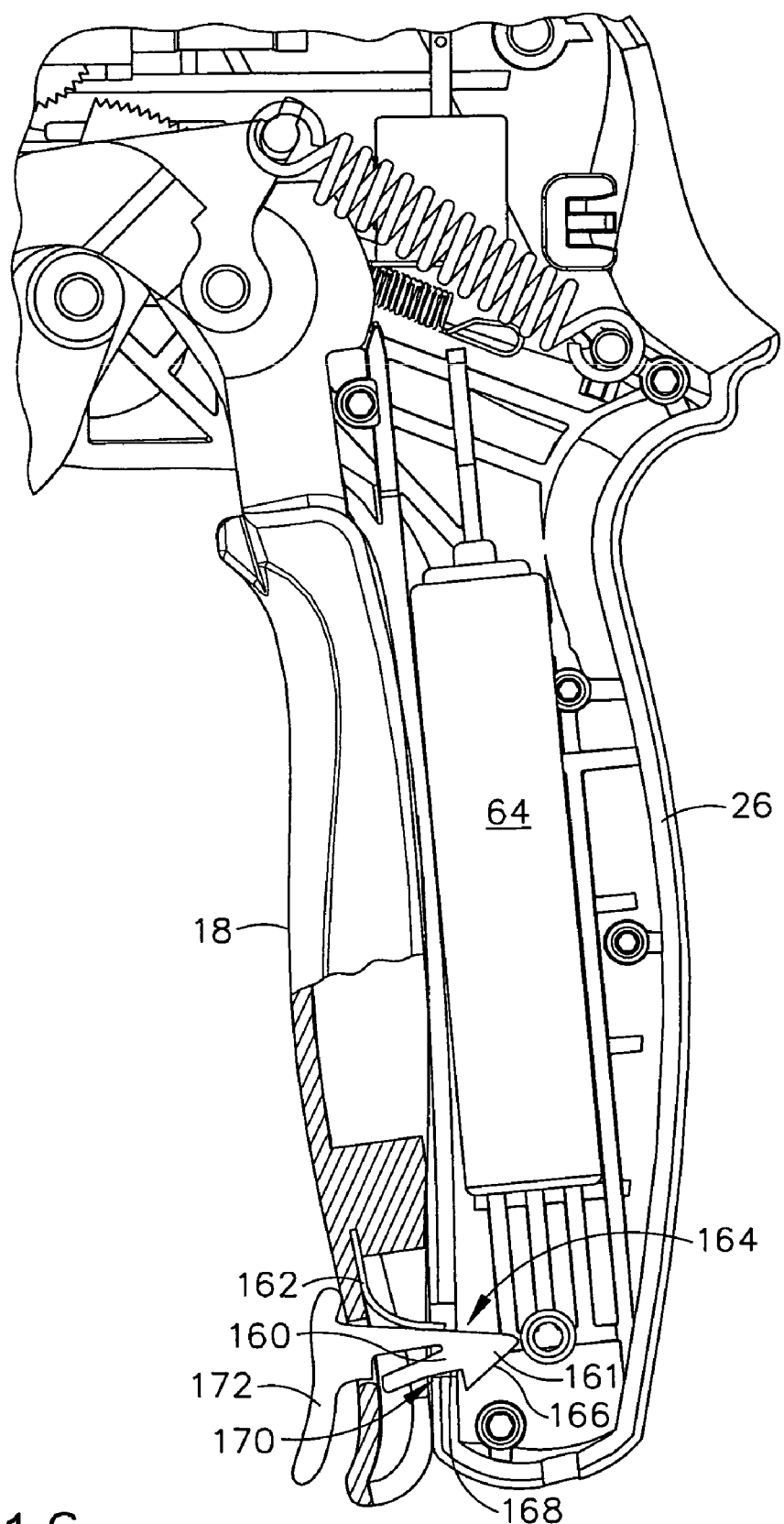

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or clockwise) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate counter clockwise. Eventually the lower chamfered surface 166 fully passes the lower sidewall 168, removing the counter clockwise force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate counter clockwise and allowing the arrow-head portion 161 to slide out of the opening 164.

Figure 17:
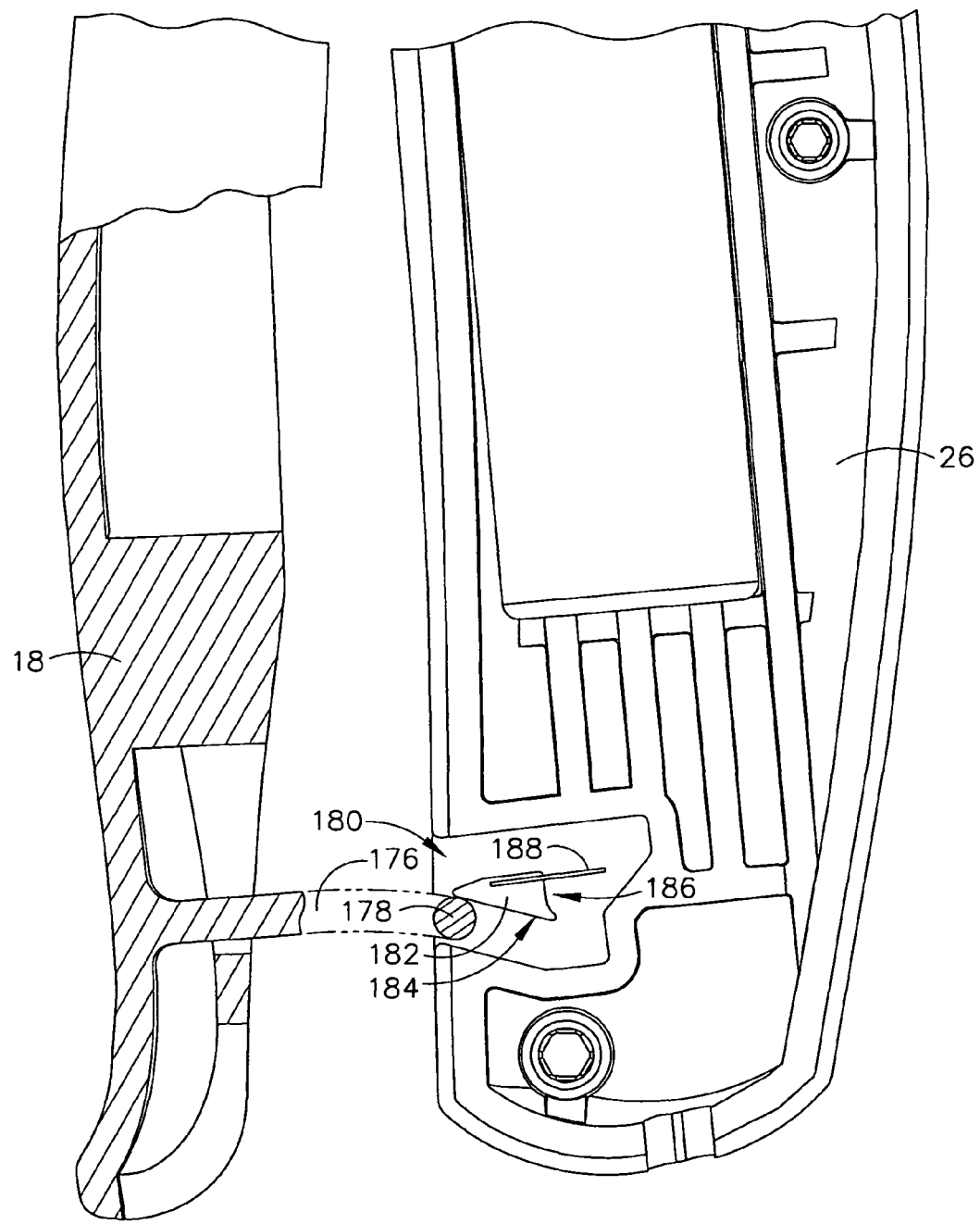
Figure 18:
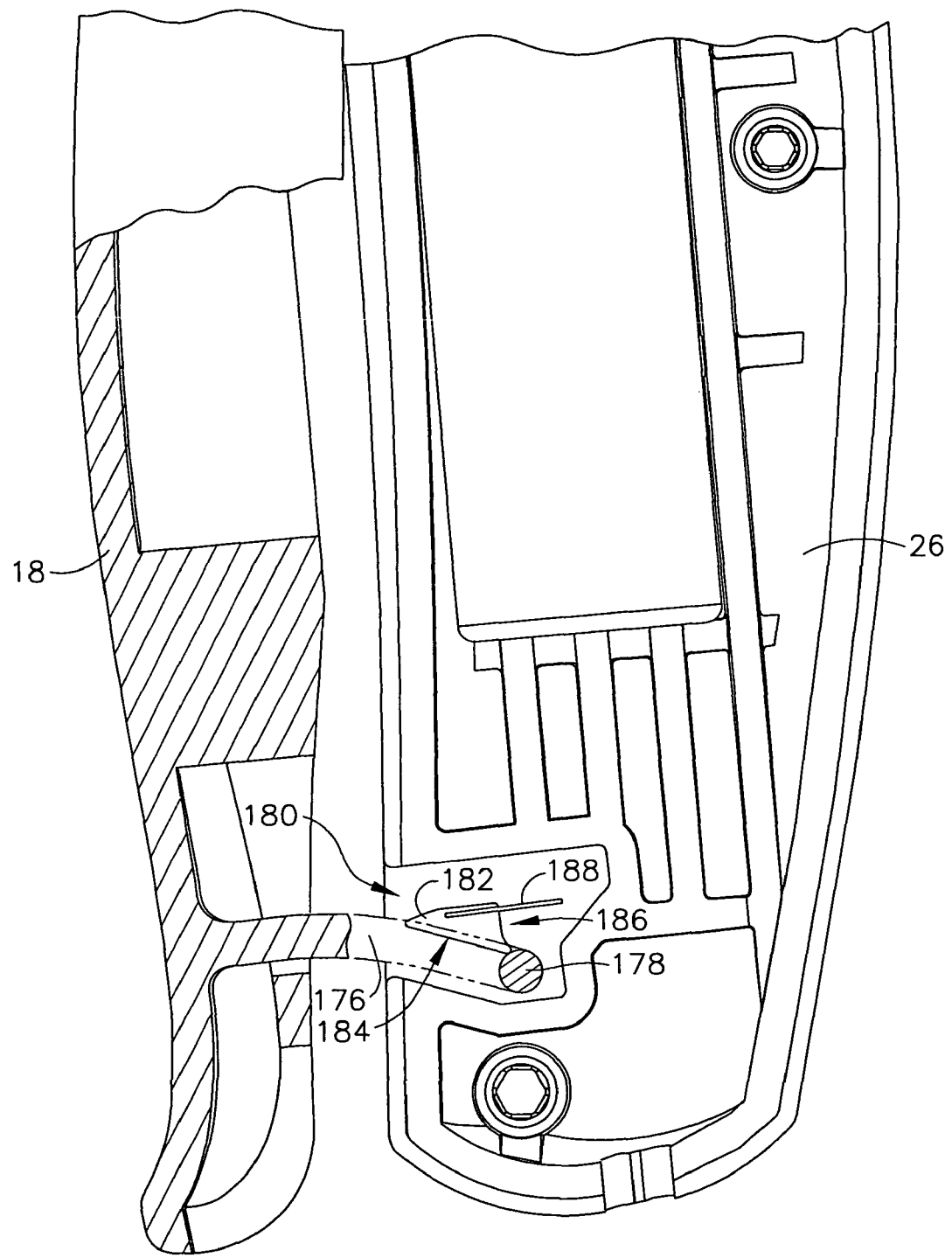
Figure 19:
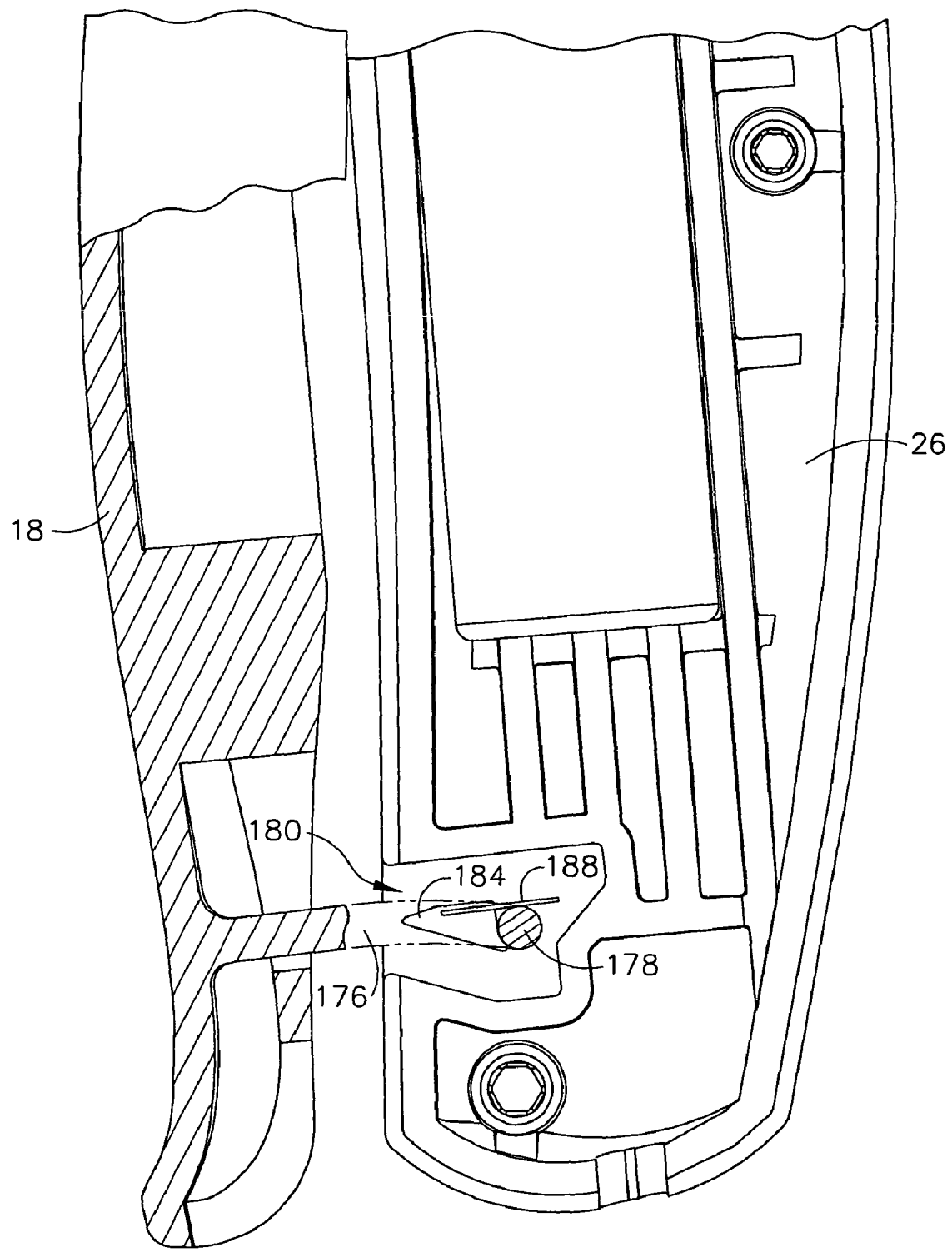

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated clockwise) by the lower surface 184 of the wedge 182, as shown in FIGS. 17 and 18. When the pin 178 fully passes the lower surface 184, the clockwise force on the arm 176 is removed, and the pin 178 is rotated counter clockwise such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
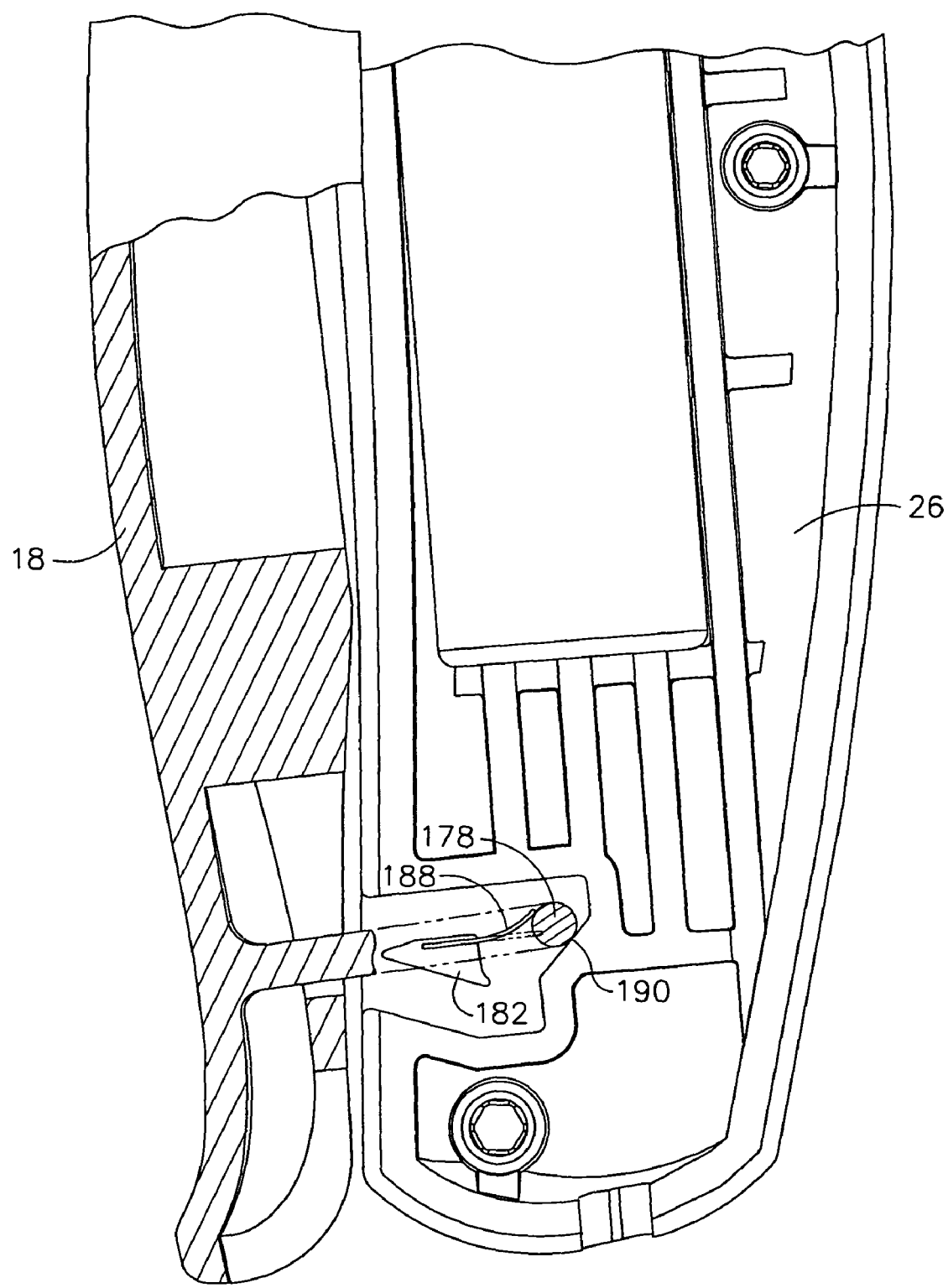
Figure 21:
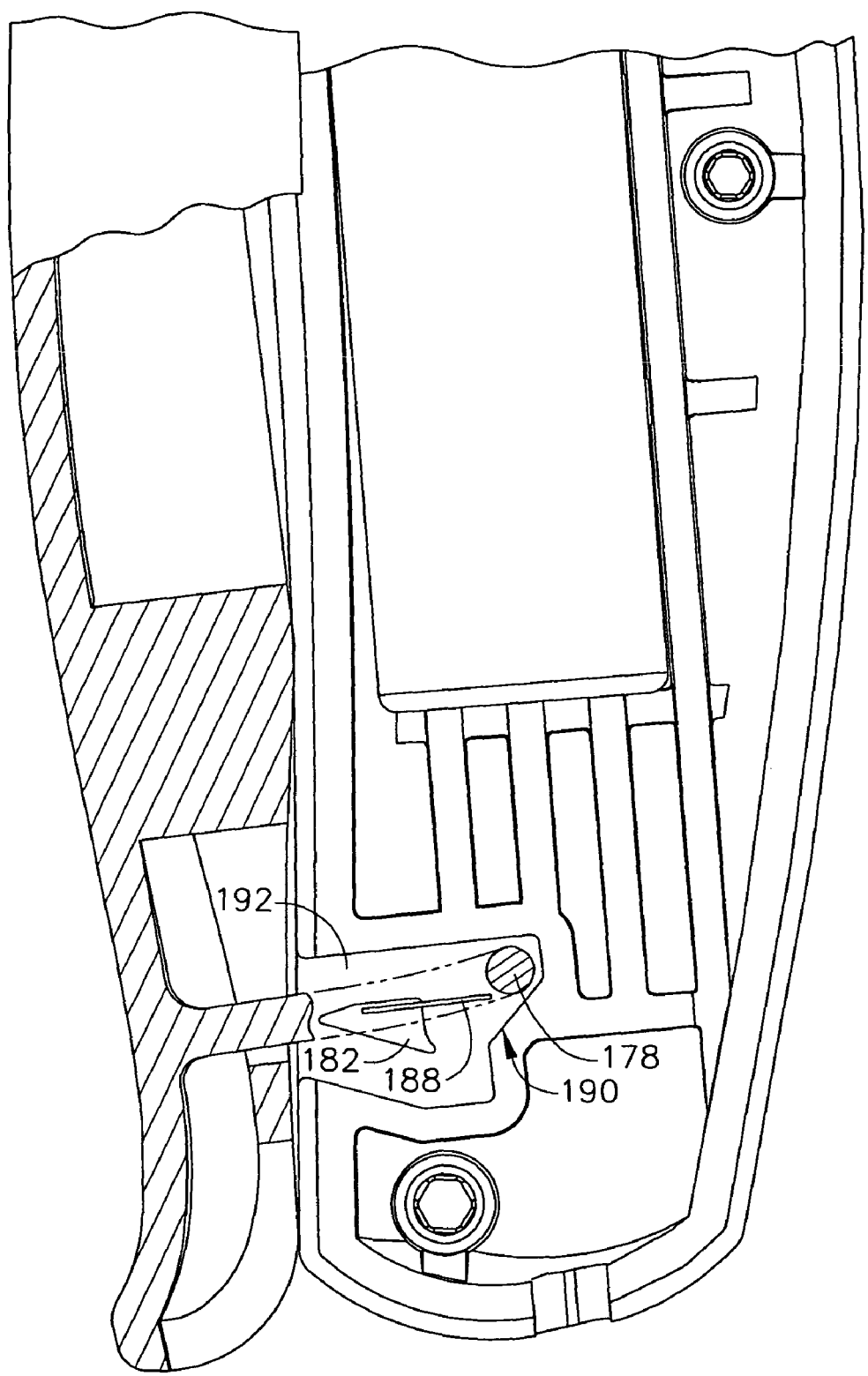
Figure 22:
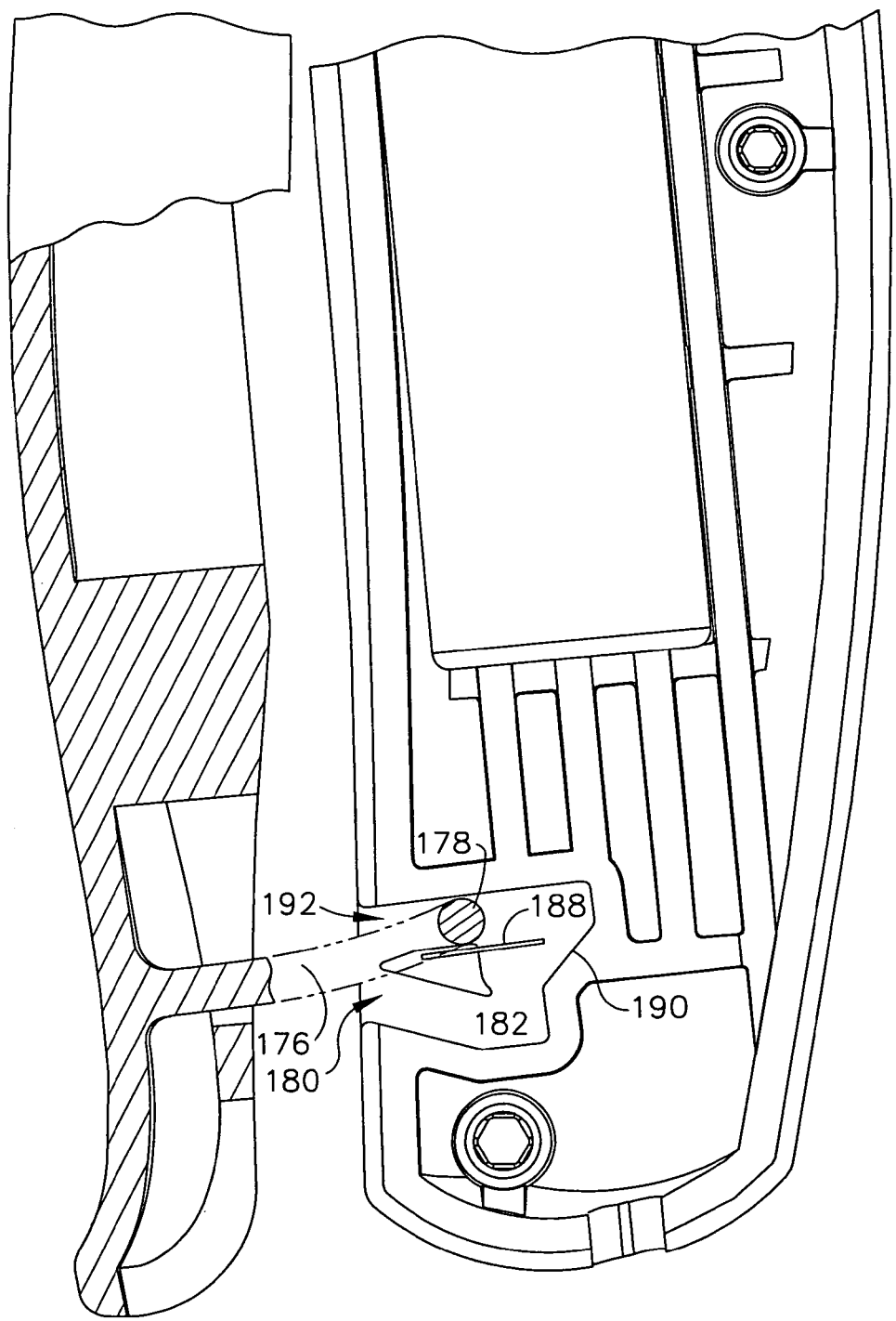

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist according to another embodiment of the present invention. The embodiment of FIGS. 25-31 is similar to that of FIGS. 6-10 except that instead of the helical gear drum 80, the embodiment of FIGS. 23-28 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 23-32 is another power assist motorized instrument 10 that provides feedback to the user regarding the loading force experienced by the instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a counter clockwise direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 68, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate counter clockwise when the motor 65 provides forward drive for the end effector 12 (and to rotate counter clockwise when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate counter clockwise, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife 32) and the end of retraction operation (full retraction of the knife 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the clockwise direction. The upper portion 230 may also include a lower arm 234 that contacts an upper surface of the lower portion 228 of the firing trigger 20 such that when the upper portion 230 is caused to rotate clockwise the lower portion 228 also rotates clockwise, and when the lower portion 228 rotates counter clockwise the upper portion 230 also rotates counter clockwise. Similarly, the lower portion 228 includes a rotational stop 238 that engages a shoulder of the upper portion 230. In that way, when the upper portion 230 is caused to rotate counter clockwise the lower portion 228 also rotates counter clockwise, and when the lower portion 228 rotates clockwise the upper portion 230 also rotates clockwise.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
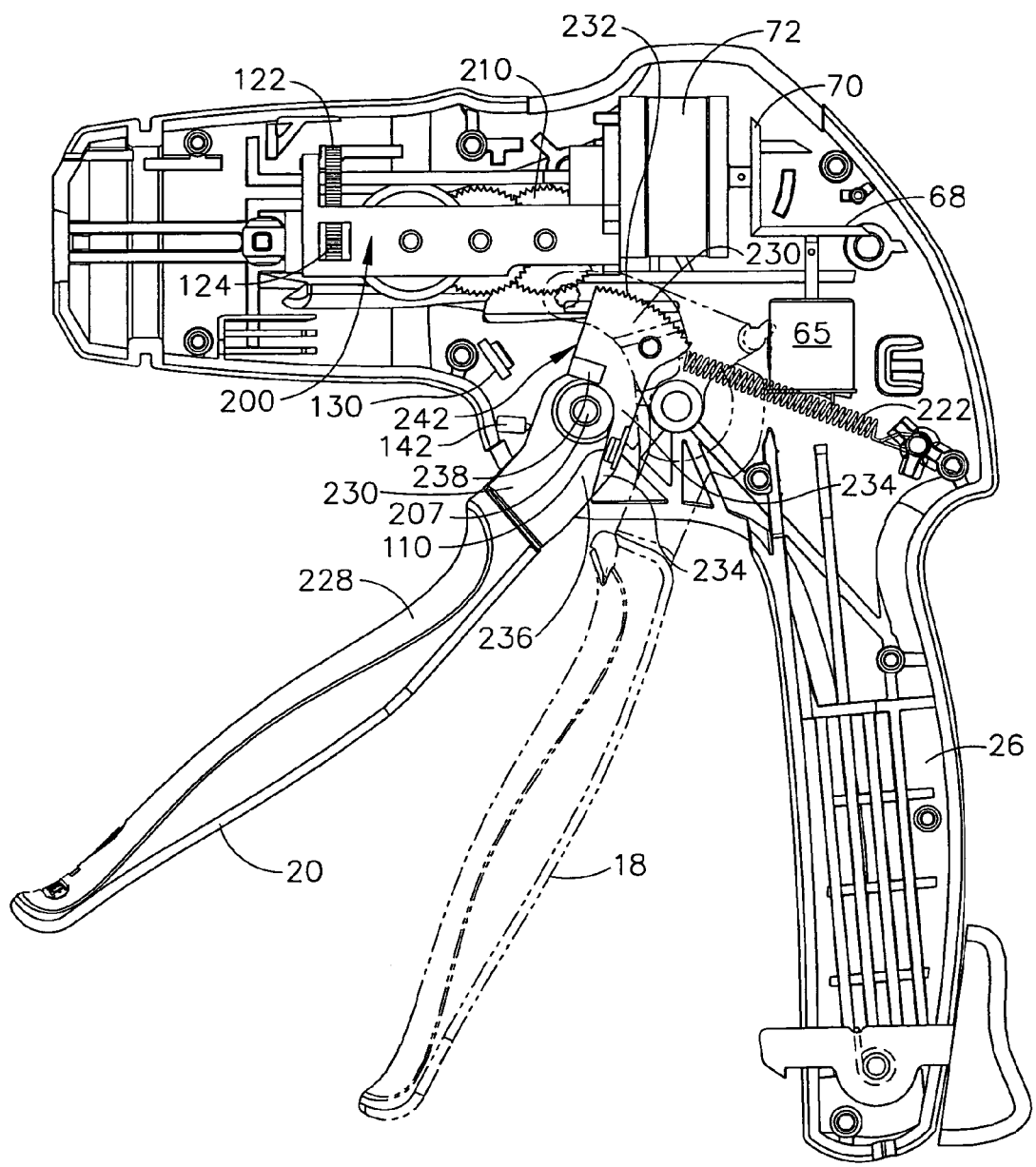
Figure 33:
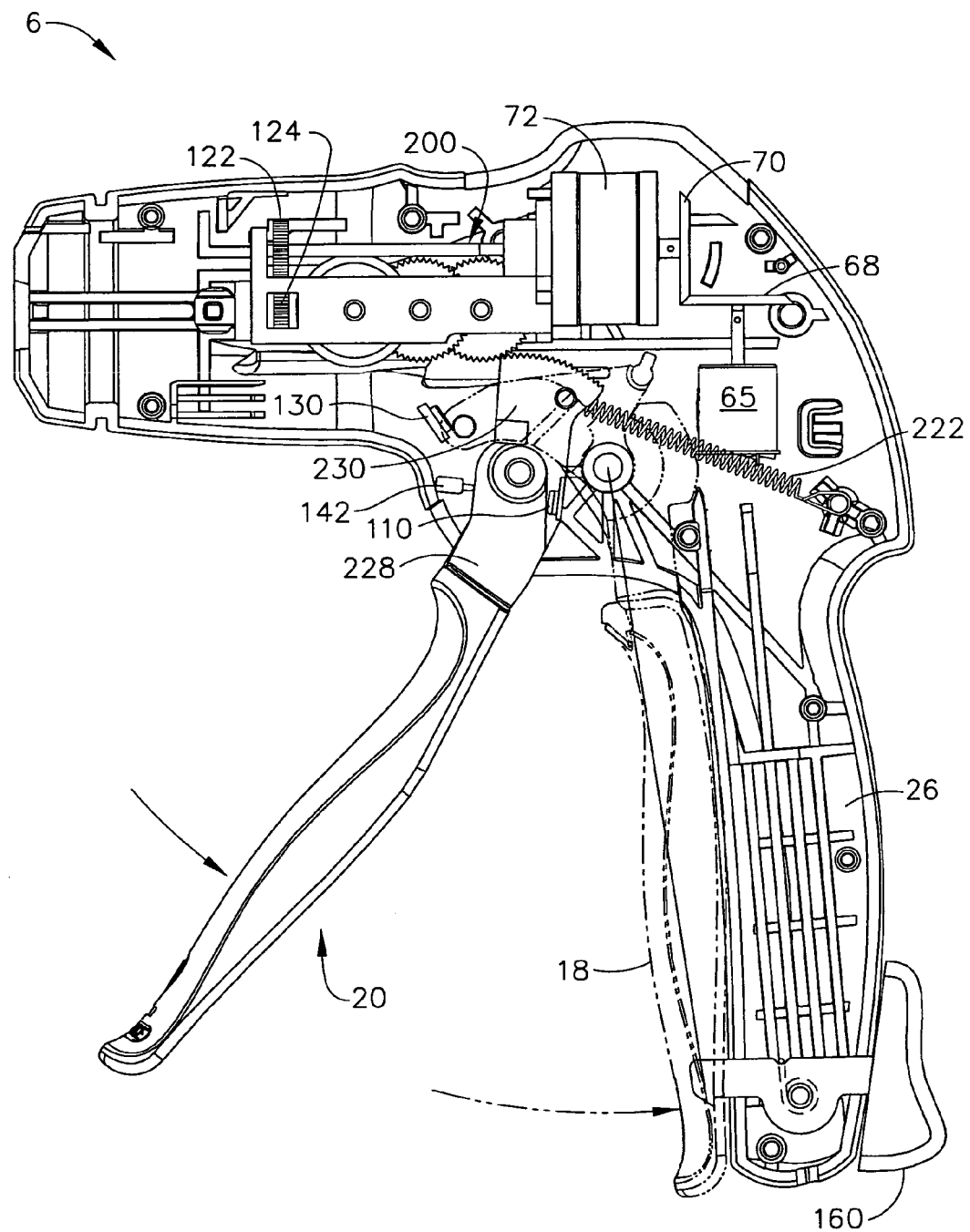
Figure 34:
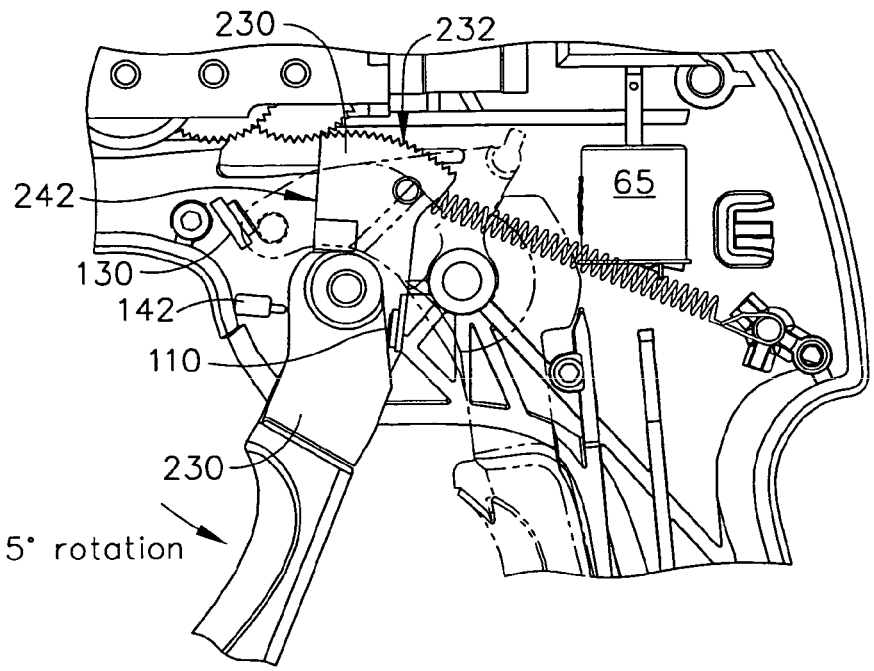
Figure 35:
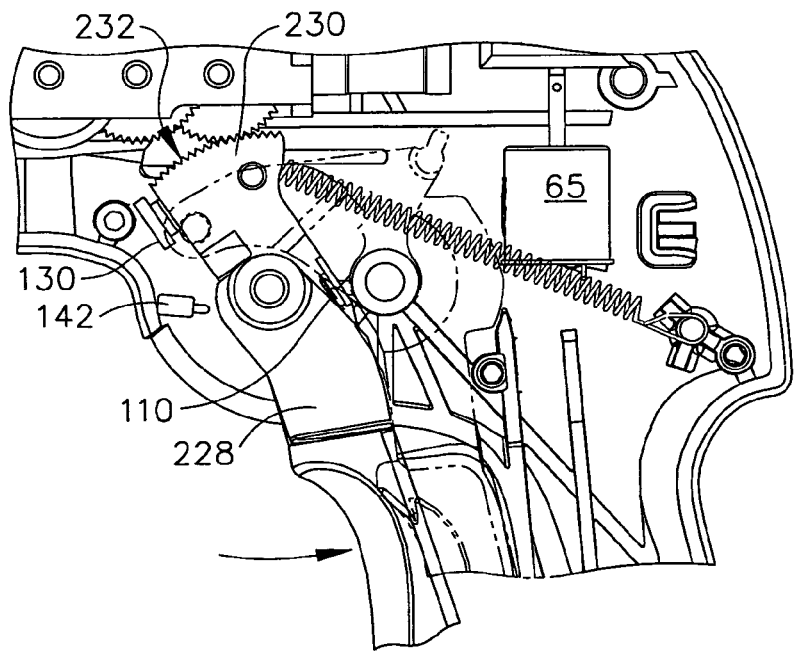
Figure 36:
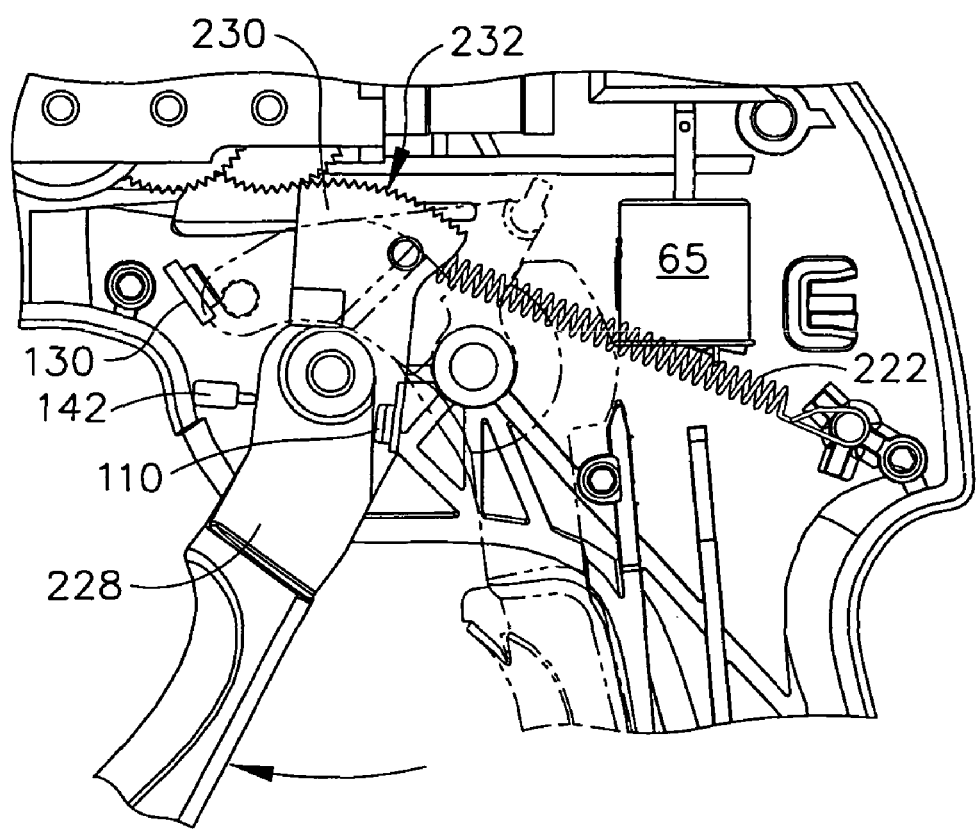

In operation, when an operator retracts the closure trigger 18 into the locked position, the firing trigger 20 is retracted slightly (through mechanisms known in the art, including U.S. Pat. No. 6,978,921 to Frederick Shelton, IV et. al and U.S. Pat. No. 6,905,057 to Jeffery S. Swayze et. al, which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate counter clockwise, which causes the lower portion 228 to also rotate counter clockwise.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly also causes the gears 210-220 in the gear box assembly to reverse direction, which causes the upper portion 230 of the firing trigger 20 to rotate clockwise, which causes the lower portion 228 of the firing trigger 20 to rotate clockwise until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate counter clockwise, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor 65, gear drive train, and end effector 12) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments of the present invention, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
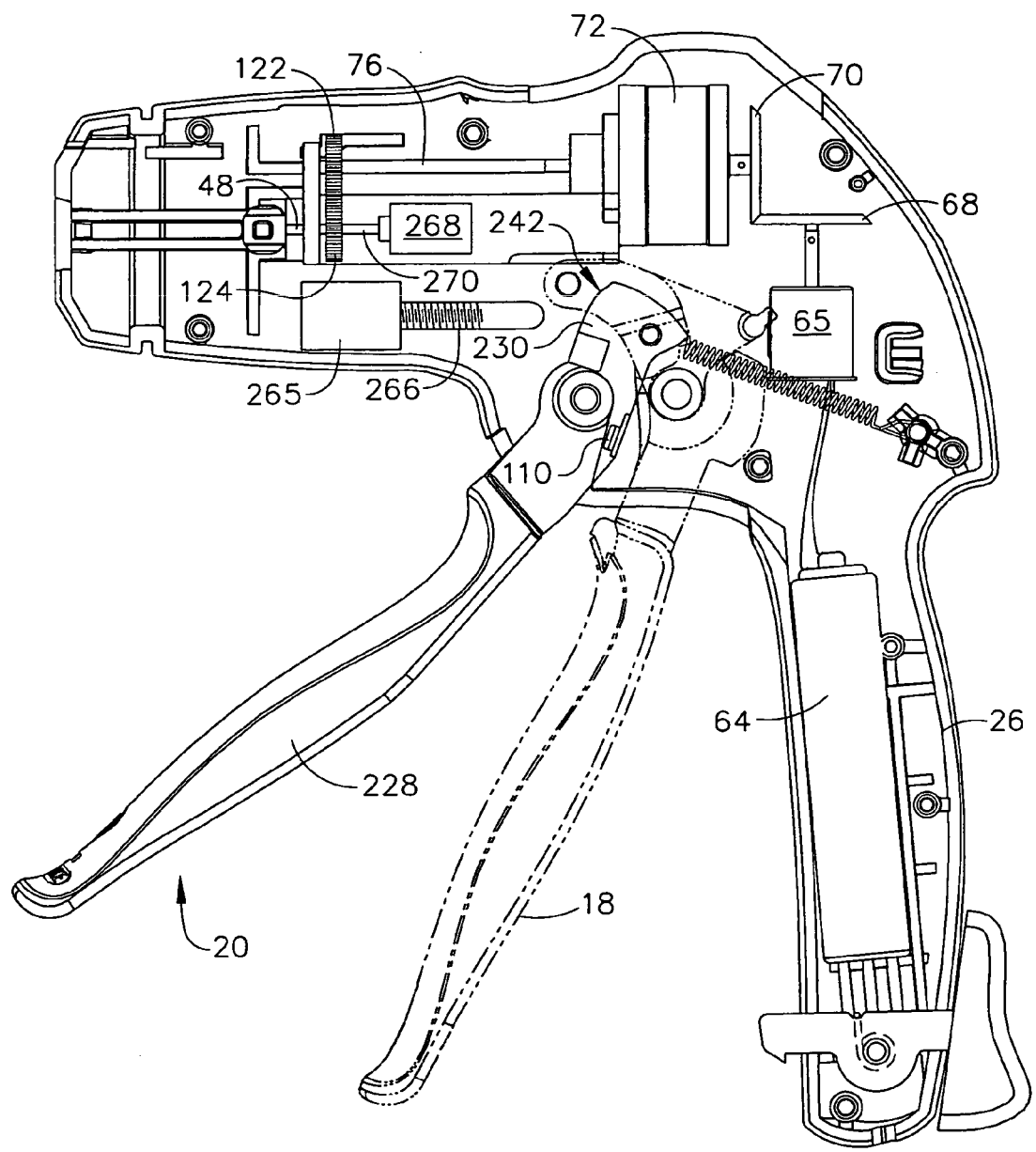
Figure 38:
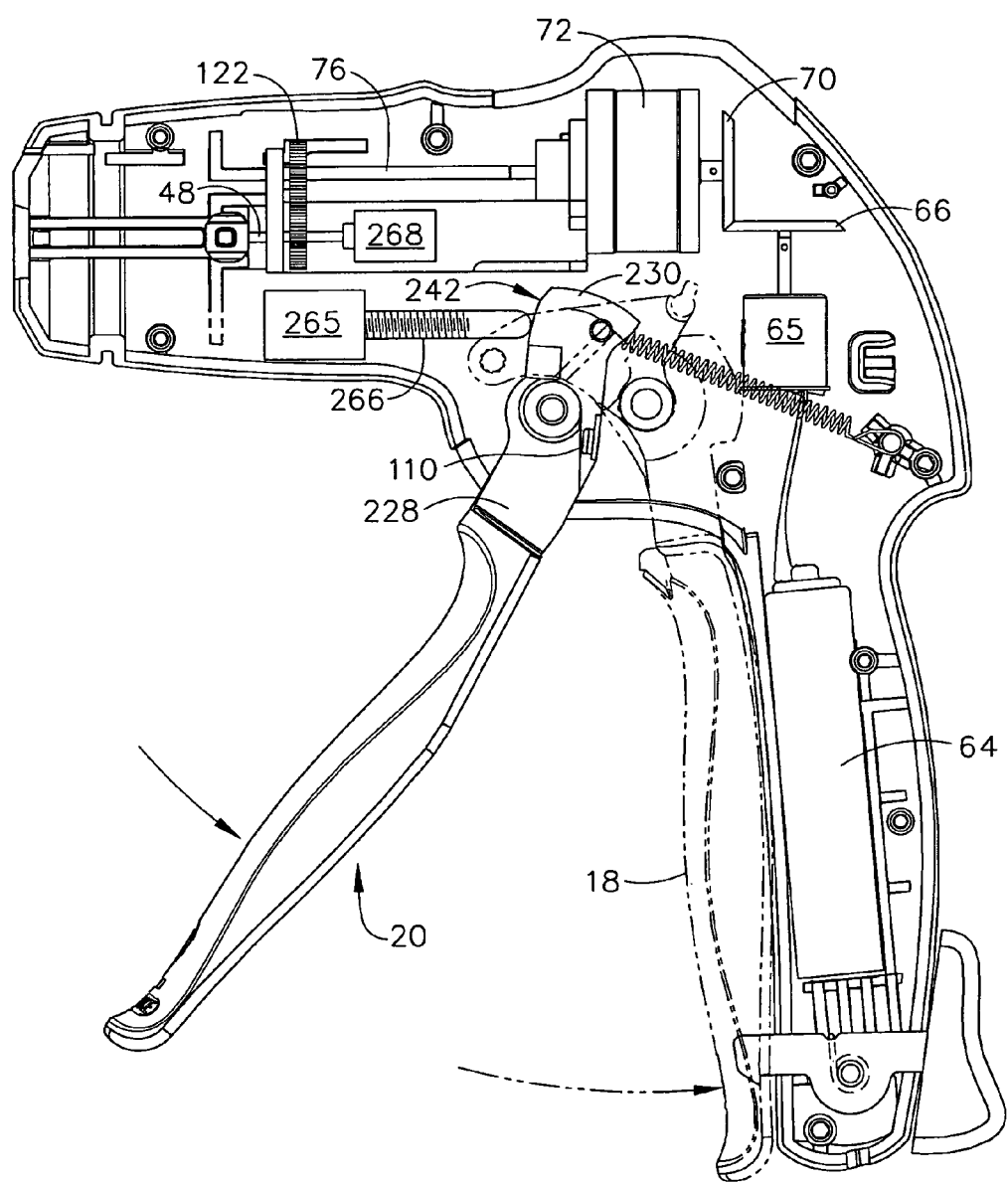
Figure 39:
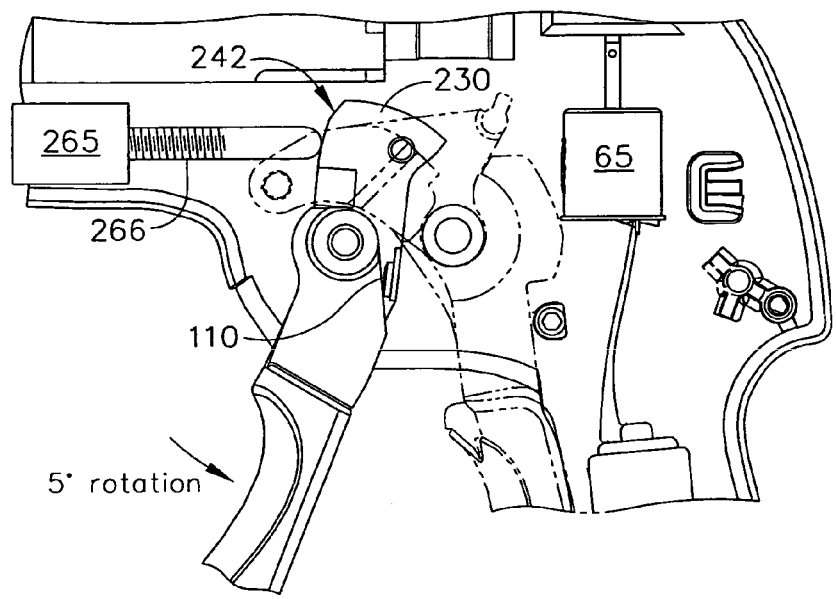
Figure 40:
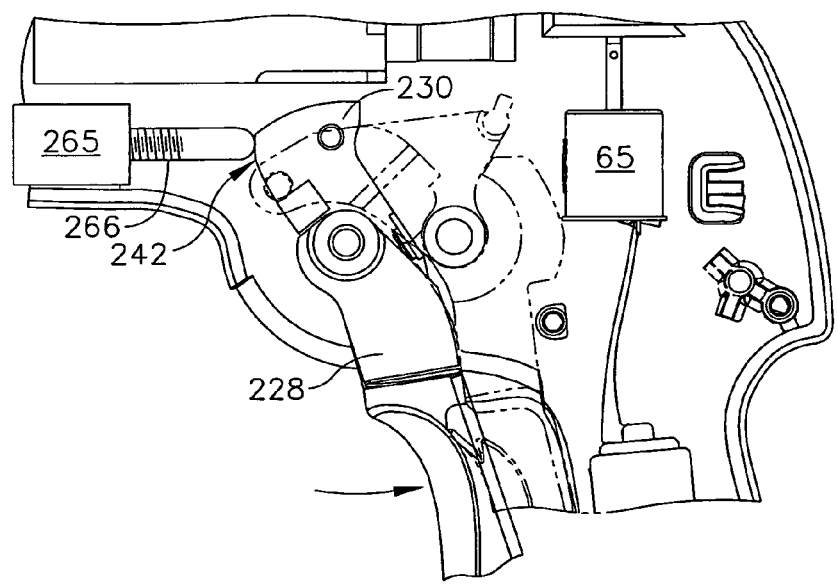

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 20 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g. 5 degrees of rotation) the run motor sensor 110 may be activated such that, as explained above, the sensor 110 sends a signal to the motor 65 to cause it to rotate at a forward speed proportional to the amount of retraction force applied by the operator to the fling trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to cause the second motor 265 to rotate, which causes the threaded rod 266 to retract into the motor 265. This allows the upper portion 230 of the firing trigger 20 to rotate counter clockwise, which allows the lower portion 228 of the firing trigger to also rotate counter clockwise. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate clockwise, which causes the lower portion 228 to rotate clockwise. In that way, the operator may experience a clockwise force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

FIGS. 41-43 illustrate an exemplary embodiment of a mechanically actuated endocutter, and in particular the handle 6, shaft 8 and end effector 12 thereof. Further details of a mechanically actuated endocutter may be found in U.S. patent application Ser. No. 11/052,632 entitled, "Surgical Stapling Instrument Incorporating A Multi-Stroke Firing Mechanism With Automatic End Of Firing Travel Retraction," which is incorporated herein by reference. With reference to FIG. 41, the end effector 12 responds to the closure motion from the handle 6 (not depicted in FIG. 41) first by including an anvil face 1002 connecting to an anvil proximal end 1004 that includes laterally projecting anvil pivot pins 25 that are proximal to a vertically projecting anvil tab 27. The anvil pivot pins 25 translate within kidney shaped openings 1006 in the staple channel 22 to open and close anvil 24 relative to channel 22. The tab 27 engages a bent tab 1007 extending inwardly in tab opening 45 on a distal end 1008 of the closure tube 1005, the latter distally terminating in a distal edge 1008 that pushes against the anvil face 1002. Thus, when the closure tube 1005 moves proximally from its open position, the bent tab 1007 of the closure tube 1005 draws the anvil tab 27 proximally, and the anvil pivot pins 25 follow the kidney shaped openings 1006 of the staple channel 22 causing the anvil 24 to simultaneously translate proximally and rotate upward to the open position. When the closure tube 1005 moves distally, the bent tab 1007 in the tab opening 45 releases from the anvil tab 27 and the distal edge 1008 pushes on the anvil face 1002, closing the anvil 24.

With continued reference to FIG. 41, the shaft 8 and end effector 12 also include components that respond to a firing motion of a firing rod 1010. In particular, the firing rod 1010 rotatably engages a firing trough member 1012 having a longitudinal recess 1014. Firing trough member 1012 moves longitudinally within frame 1016 in direct response to longitudinal motion of firing rod 1010. A longitudinal slot 1018 in the closure tube 1005 operably couples with the right and left exterior side handle pieces 61, 62 of the handle 6 (not shown in FIG. 41). The length of the longitudinal slot 1018 in the closure tube 1005 is sufficiently long to allow relative longitudinal motion with the handle pieces 61, 62 to accomplish firing and closure motions respectively with the coupling of the handle pieces 61, 62 passing on through a longitudinal slot 1020 in the frame 1016 to slidingly engage the longitudinal recess 1014 in the frame trough member 1012.

The distal end of the frame trough member 1012 is attached to a proximal end of a firing bar 1022 that moves within the frame 1016, specifically within a guide 1024 therein, to distally project the knife 32 into the end effector 12. The end effector 12 includes a staple cartridge 34 that is actuated by the knife 32. The staple cartridge 34 has a tray 1028 that holds a staple cartridge body 1030, a wedge sled driver 33, staple drivers 1034 and staples 1036. It will be appreciated that the wedge sled driver 33 longitudinally moves within a firing recess (not shown) located between the cartridge tray 1028 and the cartridge body 1030. The wedge sled driver 33 presents camming surfaces that contact and lift the staple drivers 1034 upward, driving the staples 1036. The staple cartridge body 1030 further includes a proximally open, vertical slot 1031 for passage of the knife 32. Specifically, a cutting surface 1027 is provided along a distal end of knife 32 to cut tissue after it is stapled.

It should be appreciated that the shaft 8 is shown in FIG. 4 as a non-articulating shaft. Nonetheless, applications of the present invention may include instruments capable of articulation, for example, as such shown above with reference to FIGS. 1-4 and described in the following U.S. patents and patent applications, the disclosure of each being hereby incorporated by reference in their entirety: (1) "SURGICAL INSTRUMENT INCORPORATING AN ARTICULATION MECHANISM HAVING ROTATION ABOUT THE LONGITUDINAL AXIS", U.S. Patent Application Publication No. 2005/0006434, by Frederick E. Shelton IV, Brian J. Hemmelgam, Jeffrey S. Swayze, Kenneth S. Wales, filed 9 Jul. 2003; (2) "SURGICAL STAPLING INSTRUMENT INCORPORATING AN ARTICULATION JOINT FOR A FIRING BAR TRACK", U.S. Pat. No. 6,786,382, to Brian J. Hemmelgam; (3) "A SURGICAL INSTRUMENT WITH A LATERAL-MOVING ARTICULATION CONTROL", U.S. Pat. No. 6,981,628, to Jeffrey S. Swayze; (4) "SURGICAL STAPLING INSTRUMENT INCORPORATING A TAPERED FIRING BAR FOR INCREASED FLEXIBILITY AROUND THE ARTICULATION JOINT", U.S. Pat. No. 6,964,363, to Frederick E. Shelton IV, Michael Setser, Bruce Weisenburgh II; and (5) "SURGICAL STAPLING INSTRUMENT HAVING ARTICULATION JOINT SUPPORT PLATES FOR SUPPORTING A FIRING BAR", U.S. Patent Application Publication No. 2005/0006431, by Jeffrey S. Swayze, Joseph Charles Hueil, filed 9 Jul. 2003.

FIGS. 42-43 show an embodiment of the handle 6 that is configured for use in a mechanically actuated endocutter along with the embodiment of the shaft 8 and end effector 12 as shown above in FIG. 41. It will be appreciated that any suitable handle design may be used to mechanically close and fire the end effector 12. In FIGS. 42-43, the handle 6 of the surgical stapling and severing instrument 10 includes a linked transmission firing mechanism 1060 that provides features such as increased strength, reduced handle size, minimized binding, etc.

Closure of the end effector 12 (not shown in FIGS. 42-43) is caused by depressing the closure trigger 18 toward the pistol grip 26 of handle 6. The closure trigger 18 pivots about a closure pivot pin 252 that is coupled to right and left exterior lower side pieces 59, 60 the handle 6, causing an upper portion 1094 of the closure trigger 18 to move forward. The closure tube 1005 receives this closure movement via the closure yoke 250 that is pinned to a closure tube 1042 and to the upper portion 1094 of the closure trigger 18 respectively by a closure yoke pin 1044 and a closure link pin 1046.

In the fully open position of FIG. 42, the upper portion 1094 of the closure trigger 18 contacts and holds a locking arm 1048 of the pivoting closure release button 30 in the position shown. When the closure trigger 18 reaches its fully depressed position, the closure trigger 18 releases the locking arm 1048 and an abutting surface 1050 rotates into engagement with a distal rightward notch 1052 of the pivoting locking arm 1048, holding the closure trigger 18 in this clamped or closed position. A proximal end of the locking arm 1048 pivots about a lateral pivotal connection 1054 with the pieces 59, 60 to expose the closure release button 30. An intermediate, distal side 1056 of the closure release button 30 is urged proximally by a compression spring 1058, which is compressed between a housing structure 1040 and closure release button 30. The result is that the closure release button 30 urges the locking arm 1048 counterclockwise (when viewed from the left) into locking contact with the abutting surface 1050 of closure trigger 18, which prevents unclamping of closure trigger 18 when the linked transmission firing system 1040 is in an un-retracted condition.

With the closure trigger 18 retracted and fully depressed, the firing trigger 20 is unlocked and may be depressed toward the pistol grip 26, multiple times in this embodiment, to effect firing of the end effector 12. As depicted, the linked transmission firing mechanism 1060 is initially retracted, urged to remain in this position by a combination tension/compression spring 1062 that is constrained within the pistol grip 26 of the handle 6, with its nonmoving end 1063 connected to the pieces 59, 60 and a moving end 1064 connected to a downwardly flexed and proximal, retracted end 1067 of a steel band 1066.

A distally-disposed end 1068 of the steel band 1066 is attached to a link coupling 1070 for structural loading, which in turn is attached to a front link 1072a of a plurality of links 1072a-1072d that form a linked rack 1074. Linked rack 1074 is flexible yet has distal links that form a straight rigid rack assembly that may transfer a significant firing force through the firing rod 1010 in the shaft 6, yet readily retract into the pistol grip 26 to minimize the longitudinal length of the handle 6. It should be appreciated that the combination tension/compression spring 1062 increases the amount of firing travel available while essentially reducing the minimum length by half over a single spring.

The firing trigger 20 pivots about a firing trigger pin 96 that is connected to the handle pieces 59, 60. An upper portion 228 of the firing trigger 20 moves distally about the firing trigger pin 96 as the firing trigger 20 is depressed towards pistol grip 26, stretching a proximally placed firing trigger tension spring 222 proximally connected between the upper portion 228 of the firing trigger 20 and the pieces 59, 60. The upper portion 228 of the firing trigger 20 engages the linked rack 1074 during each firing trigger depression by a traction biasing mechanism 1078 that also disengages when the firing trigger 20 is released. Firing trigger tension spring 222 urges the firing trigger 20 distally when released and disengages the traction biasing mechanism 1078.

As the linked transmission firing mechanism 1040 actuates, an idler gear 1080 is rotated clockwise (as viewed from the left side) by engagement with a toothed upper surface 1082 of the linked rack 1074. This rotation is coupled to an indicator gear 1084, which thus rotates counterclockwise in response to the idler gear 1080. Both the idler gear 1080 and indicator gear 1084 are rotatably connected to the pieces 59, 60 of the handle 6. The gear relationship between the linked rack 1074, idler gear 1080 and indicator gear 1084 may be advantageously selected so that the toothed upper surface 1082 has tooth dimensions that are suitably strong and that the indicator gear 1084 makes no more than one revolution during the full firing travel of the linked transmission firing mechanism 1060.

As described in greater detail below, the indicator gear 1084 performs at least four functions. First, when the linked rack 1074 is fully retracted and both triggers 18, 20 are open as shown in FIG. 42, an opening 1086 in a circular ridge 1088 on the l side of the indicator gear 1084 is presented to an upper surface 1090 of the locking arm 1048. Locking arm 1048 is biased into the opening 1086 by contact with the closure trigger 18, which in turn is urged to the open position by a closure tension spring 1092. Closure trigger tension spring 1092 is connected proximally to the upper portion 1094 of the closure trigger 18 and the handle pieces 59, 60, and thus has energy stored during closing of the closure trigger 18 that urges the closure trigger 18 distally to its unclosed position.

A second function of the indicator gear 1084 is that it is connected to the indicating retraction knob 1096 externally disposed on the handle 6. Thus, the indicator gear 1084 communicates the relative position of the firing mechanism 1060 to the indicating retraction knob 1096 so that the surgeon has a visual indication of how many strokes of the firing trigger 20 are required to complete firing.

A third function of the indicator gear 1084 is to longitudinally and angularly move an anti-backup release lever 1098 of an anti-backup mechanism (one-way clutch mechanism) 1097 as the surgical stapling and severing instrument 10 is operated. During the firing strokes, proximal movement of anti-backup release lever 1098 by indicator gear 1084 activates the anti-backup mechanism 1097 that allows distal movement of firing bar 1010 and prevents proximal motion of firing bar 1010. This movement also extends the anti-backup release button 1100 from the proximal end of the handle pieces 59, 60 for the operator to actuate should the need arise for the linked transmission firing mechanism 1060 to be retracted during the firing strokes. After completion of the firing strokes, the indicator gear 1084 reverses direction of rotation as the firing mechanism 1060 retracts. The reversed rotation deactivates the anti-backup mechanism 1097, withdraws the anti-backup release button 1100 into the handle 6, and rotates the anti-backup release lever 1098 laterally to the right to allow continued reverse rotation of the indicator gear 1084.

A fourth function of the indicator gear 1084 is to receive a manual rotation from the indicating retraction knob 1096 (clockwise in the depiction of FIG. 42) to retract the firing mechanism 1060 with anti-backup mechanism 1097 unlocked, thereby overcoming any binding in the firing mechanism 1060 that is not readily overcome by the combination tension/compression spring 1062. This manual retraction assistance may be employed after a partial firing of the firing mechanism 1060 that would otherwise be prevented by the anti-backup mechanism 1097 that withdraws the anti-backup release button 1100 so that the latter may not laterally move the anti-backup release lever 1098.

Continuing with FIGS. 42-43, anti-backup mechanism 1097 consists of the operator accessible anti-backup release lever 1098 operably coupled at the proximal end to the anti-backup release button 1100 and at the distal end to an anti-backup yoke 1102. In particular, a distal end 1099 of the anti-backup release lever 1098 is engaged to the anti-backup yoke 1102 by an anti-backup yoke pin 1104. The anti-backup yoke 1102 moves longitudinally to impart a rotation to an anti-backup cam slot tube 1106 that is longitudinally constrained by the handle pieces 59, 90 and that encompasses the firing rod 1010 distally to the connection of the firing rod 1010 to the link coupling 1070 of the linked rack 1074. The anti-backup yoke 1102 communicates the longitudinal movement from the anti-backup release lever 1098 via a cam slot tube pin 1108 to the anti-backup cam slot tube 1106. That is, longitudinal movement of cam slot tube pin 1108 in an angled slot in the anti-backup cam slot tube 1106 rotates the anti-backup cam slot tube 1106.

Trapped between a proximal end of the frame 1016 and the anti-backup cam slot tube 1106 respectively are an anti-backup compression spring 1110, an anti-backup plate 1112, and an anti-backup cam tube 1114. As depicted, proximal movement of the firing rod 1010 causes the anti-backup plate 1112 to pivot top to the rear, presenting an increased frictional contact to the firing rod 1010 that resists further proximal movement of the firing rod 1010.

This anti-backup plate 1112 pivots in a manner similar to that of a screen door lock that holds open a screen door when the anti-backup cam slot tube 1106 is closely spaced to the anti-backup cam tube 1114. Specifically, the anti-backup compression spring 1110 is able to act upon a top surface of the plate 1112 to tip the anti-backup plate 1112 to its locked position. Rotation of the anti-backup cam slot tube 1106 causes a distal camming movement of the anti-backup cam tube 1114 thereby forcing the top of the anti-backup plate 1112 distally, overcoming the force from the anti-backup compression spring 1110, thus positioning the anti-backup plate 1112 in an untipped (perpendicular), unlocked position that allows proximal retraction of the firing rod 1010.

With particular reference to FIG. 43, the traction biasing mechanism 1078 is depicted as being composed of a pawl 1116 that has a distally projecting narrow tip 1118 and a rightwardly projecting lateral pin 1120 at its proximal end that is rotatably inserted through a hole 1076 in the upper portion 230 of the firing trigger 20. On the right side of the firing trigger 20 the lateral pin 1120 receives a biasing member, depicted as biasing wheel 1122. As the firing trigger 20 translates fore and aft, the biasing wheel 1122 traverses an arc proximate to the right half piece 59 of the handle 6, overrunning at its distal portion of travel a biasing ramp 1124 integrally formed in the right half piece 59. The biasing wheel 1122 may advantageously be formed from a resilient, frictional material that induces a counterclockwise rotation (when viewed from the left) into the lateral pin 1120 of the pawl 1116, thus traction biasing the distally projecting narrow tip 1118 downward into a ramped central track 1075 of the nearest link 1072a-d to engage the linked rack 1074.

As the firing trigger 20 is released, the biasing wheel 1122 thus tractionally biases the pawl 1116 in the opposite direction, raising the narrow tip 1118 from the ramped central track 1075 of the linked rack 1074. To ensure disengagement of the tip 1118 under high load conditions and at nearly full distal travel of the pawl 1116, the right side of the pawl 1116 ramps up onto a proximally and upwardly facing beveled surface 1126 on the rightside of the closure yoke 250 to disengage the narrow tip 1118 from the ramped central track 1075. If the firing trigger 20 is released at any point other than full travel, the biasing wheel 1122 is used to lift the narrow tip 1118 from the ramped central track 1075. Whereas a biasing wheel 1122 is depicted, it should be appreciated that the shape of the biasing member or wheel 1122 is illustrative and may be varied to accommodate a variety of shapes that use friction or traction to engage or disengage the firing of the end effector 12.

Various embodiments of the surgical instrument 10 have the capability to record instrument conditions at one or more times during use. FIG. 44 shows a block diagram of a system 2000 for recording conditions of the instrument 10. It will be appreciated that the system 2000 may be implemented in embodiments of the instrument 10 having motorized or motor-assisted firing, for example, as described above with reference to FIGS. 1-40, as well as embodiments of the instrument 10 having mechanically actuated firing, for example, as described above with reference to FIGS. 41-43.

The system 2000 may include various sensors 2002, 2004, 2006, 2008, 2010, 2012 for sensing instrument conditions. The sensors may be positioned, for example, on or within the instrument 10. In various embodiments, the sensors may be dedicated sensors that provide output only for the system 2000, or may be dual-use sensors that perform other functions with in the instrument 10. For example, sensors 110, 130, 142 described above may be configured to also provide output to the system 2000.

Directly or indirectly, each sensor provides a signal to the memory device 2001, which records the signals as described in more detail below. The memory device 2001 may be any kind of device capable of storing or recording sensor signals. For example, the memory device 2001 may include a microprocessor, an Electrically Erasable Programmable Read Only Memory (FEPROM), or any other suitable storage device. The memory device 2001 may record the signals provided by the sensors in any suitable way. For example, in one embodiment, the memory device 2001 may record the signal from a particular sensor when that signal changes states. In another embodiment, the memory device 2001 may record a state of the system 2000, e.g., the signals from all of the sensors included in the system 2000, when the signal from any sensor changes states. This may provide a snap-shot of the state of the instrument 10. In various embodiments, the memory device 2001 and/or sensors may be implemented to include 1-WIRE bus products available from DALLAS SEMICONDUCTOR such as, for example, a 1-WIRE EEPROM.

In various embodiments, the memory device 2001 is externally accessible, allowing an outside device, such as a computer, to access the instrument conditions recorded by the memory device 2001. For example, the memory device 2001 may include a data port 2020. The data port 2020 may provide the stored instrument conditions according to any wired or wireless communication protocol in, for example, serial or parallel format. The memory device 2001 may also include a removable medium 2021 in addition to or instead of the output port 2020. The removable medium 2021 may be any kind of suitable data storage device that can be removed from the instrument 10. For example, the removable medium 2021 may include any suitable kind of flash memory, such as a Personal Computer Memory Card International Association (PCMCIA) card, a COMPACTFLASH card, a MULTIMEDIA card, a FLASHMEDIA card, etc. The removable medium 2021 may also include any suitable kind of disk-based storage including, for example, a portable hard drive, a compact disk (CD), a digital video disk (DVD), etc.

The closure trigger sensor 2002 senses a condition of the closure trigger 18. FIGS. 45 and 46 show an exemplary embodiment of the closure trigger sensor 2002. In FIGS. 45 and 46, the closure trigger sensor 2002 is positioned between the closure trigger 18 and closure pivot pin 252. It will be appreciated that pulling the closure trigger 18 toward the pistol grip 26 causes the closure trigger 18 to exert a force on the closure pivot pin 252. The sensor 2002 may be sensitive to this force, and generate a signal in response thereto, for example, as described above with respect to sensor 110 and FIGS. 10A and 10B. In various embodiments, the closure trigger sensor 2002 may be a digital sensor that indicates only whether the closure trigger 18 is actuated or not actuated. In other various embodiments, the closure trigger sensor 2002 may be an analog sensor that indicates the force exerted on the closure trigger 18 and/or the position of the closure trigger 18. If the closure trigger sensor 2002 is an analog sensor, an analog-to-digital converter may be logically positioned between the sensor 2002 and the memory device 2001. Also, it will be appreciated that the closure trigger sensor 2002 may take any suitable form and be placed at any suitable location that allows sensing of the condition of the closure trigger.

The anvil closure sensor 2004 may sense whether the anvil 24 is closed. FIG. 47 shows an exemplary anvil closure sensor 2004. The sensor 2004 is positioned next to, or within the kidney shaped openings 1006 of the staple channel 22 as shown. As the anvil 24 is closed, anvil pivot pins 25 slides through the kidney shaped openings 1006 and into contact with the sensor 2004, causing the sensor 2004 to generate a signal indicating that the anvil 24 is closed. The sensor 2004 may be any suitable kind of digital or analog sensor including a proximity sensor, etc. It will be appreciated that when the anvil closure sensor 2004 is an analog sensor, an analog-to-digital converter may be included logically between the sensor 2004 and the memory device 2001.

Anvil closure load sensor 2006 is shown placed on an inside bottom surface of the staple channel 22. In use, the sensor 2006 may be in contact with a bottom side of the staple cartridge 34 (not shown in FIG. 46). As the anvil 24 is closed, it exerts a force on the staple cartridge 34 which is transferred to the sensor 2006. In response, the sensor 2006 generates a signal. The signal may be an analog signal proportional to the force exerted on the sensor 2006 by the staple cartridge 34 and due to the closing of the anvil 24. Referring the FIG. 44, the analog signal may be provided to an analog-to-digital converter 2014, which converts the analog signal to a digital signal before providing it to the memory device 2001. It will be appreciated that embodiments where the sensor 2006 is a digital or binary sensor may not include analog-to-digital converter 2014.

The firing trigger sensor 110 senses the position and/or state of the firing trigger 20. In motorized or motor-assisted embodiments of the instrument, the firing trigger sensor may double as the run motor sensor 110 described above. In addition, the firing trigger sensor 110 may take any of the forms described above, and may be analog or digital. FIGS. 45 and 46 show an additional embodiment of the firing trigger sensor 110. In FIGS. 45 and 46, the firing trigger sensor is mounted between firing trigger 20 and firing trigger pivot pin 96. When firing trigger 20 is pulled, it will exert a force on firing trigger pivot pin 96 that is sensed by the sensor 110. Referring to FIG. 44, In embodiments where the output of the firing trigger sensor 110 is analog, analog-to-digital converter 2016 is included logically between the firing trigger sensor 110 and the memory device 2001.

The knife position sensor 2008 senses the position of the knife 32 or cutting surface 1027 within the staple channel 22. FIGS. 47 and 48 show embodiments of a knife position sensor 2008 that are suitable for use with the mechanically actuated shaft 8 and end effector 12 shown in FIG. 41. The sensor 2008 includes a magnet 2009 coupled to the firing bar 1022 of the instrument 10. A coil 2011 is positioned around the firing bar 1022, and may be installed; for example, along the longitudinal recess 1014 of the firing trough member 1012 (see FIG. 41). As the knife 32 and cutting surface 1027 are reciprocated through the staple channel 22, the firing bar 1022 and magnet 2009 may move back and forth through the coil 2011. This motion relative to the coil induces a voltage in the coil proportional to the position of the firing rod within the coil and the cutting edge 1027 within the staple channel 22. This voltage may be provided to the memory device 2001, for example, via analog-to-digital converter 2018.

In various embodiments, the knife position sensor 2008 may instead be implemented as a series of digital sensors (not shown) placed at various positions on or within the shaft 8. The digital sensors may sense a feature of the firing bar 1022 such as, for example, magnet 2009, as the feature reciprocates through the shaft 8. The position of the firing bar 1022, within the shaft 8, and by extension, the position of the knife 32 within the staple channel 22, may be approximated as the position of the last digital sensor tripped.

It will be appreciated that the knife position may also be sensed in embodiments of the instrument 10 having a rotary driven end effector 12 and shaft 8, for example, as described above, with reference to FIGS. 3-6. An encoder, such as encoder 268, may be configured to generate a signal proportional to the rotation of the helical screw shaft 36, or any other drive shaft or gear. Because the rotation of the shaft 36 and other drive shafts and gears is proportional to the movement of the knife 32 through the channel 22, the signal generated by the encoder 268 is also proportional to the movement of the knife 32. Thus, the output of the encoder 268 may be provided to the memory device 2001.

The cartridge present sensor 2010 may sense the presence of the staple cartridge 34 within the staple channel 22. In motorized or motor-assisted instruments, the cartridge present sensor 2010 may double as the cartridge lock-out sensor 136 described above with reference to FIG. 11. FIGS. 50 and 51 show an embodiment of the cartridge present sensor 2010. In the embodiment shown, the cartridge present sensor 2010 includes two contacts, 2011 and 2013. When no cartridge 34 is present, the contacts 2011, 2013 form an open circuit. When a cartridge 34 is present, the cartridge tray 1028 of the staple cartridge sensor 2010 may output a logic zero. When the circuit is closed, the sensor 2010 may output a logic one. The output of the sensor 2010 is provided to memory device 2001, as shown in FIG. 44.

The cartridge condition sensor 2012 may indicate whether a cartridge 34 installed within the staple channel 22 has been fired or spent. As the knife 32 is translated through the end effector 12, it pushes the sled 33, which fires the staple cartridge. Then the knife 32 is translated back to its original position, leaving the sled 33 at the distal end of the cartridge. Without the sled 33 to guide it, the knife 32 may fall into lock-out pocket 2022. Sensor 2012 may sense whether the knife 32 is present in the lock-out pocket 2022, which indirectly indicates whether the cartridge 34 has been spent. It will be appreciated that in various embodiments, sensor 2012 may directly sense the present of the sled at the proximate end of the cartridge 34, thus eliminating the need for the knife 32 to fall into the lock-out pocket 2022.

FIGS. 52A and 52B depict a process flow 2200 for operating embodiments of the surgical instrument 10 configured as an endocutter and having the capability to record instrument conditions according to various embodiments. At box 2202, the anvil 24 of the instrument 10 may be closed. This causes the closure trigger sensor 2002 and or the anvil closure sensor 2006 to change state. In response, the memory device 2001 may record the state of all of the sensors in the system 2000 at box 2203. At box 2204, the instrument 10 may be inserted into a patient. When the instrument is inserted, the anvil 24 may be opened and closed at box 2206, for example, to manipulate tissue at the surgical site. Each opening and closing of the anvil 24 causes the closure trigger sensor 2002 and/or the anvil closure sensor 2004 to change state. In response, the memory device 2001 records the state of the system 2000 at box 2205.

At box 2208, tissue is clamped for cutting and stapling. If the anvil 24 is not closed at decision block 2210, continued clamping is required. If the anvil 24 is closed, then the sensors 2002, 2004 and/or 2006 may change state, prompting the memory device 2001 to record the state of the system at box 2213. This recording may include a closure pressure received from sensor 2006. At box 2212, cutting and stapling may occur. Firing trigger sensor 110 may change state as the firing trigger 20 is pulled toward the pistol grip 26. Also, as the knife 32 moves through the staple channel 22, knife position sensor 2008 will change state. In response, the memory device 2001 may record the state of the system 2000 at box 2013.

When the cutting and stapling operations are complete, the knife 32 may return to a pre-firing position. Because the cartridge 34 has now been fired, the knife 32 may fall into lock-out pocket 2022, changing the state of cartridge condition sensor 2012 and triggering the memory device 2001 to record the state of the system 2000 at box 2015. The anvil 24 may then be opened to clear the tissue. This may cause one or more of the closure trigger sensor 2002, anvil closure sensor 2004 and anvil closure load sensor 2006 to change state, resulting in a recordation of the state of the system 2000 at box 2017. After the tissue is cleared, the anvil 24 may be again closed at box 2220. This causes another state change for at least sensors 2002 and 2004, which in turn causes the memory device 2001 to record the state of the system at box 2019. Then the instrument 10 may be removed from the patient at box 2222.

If the instrument 10 is to be used again during the same procedure, the anvil may be opened at box 2224, triggering another recordation of the system state at box 2223. The spent cartridge 34 may be removed from the end effector 12 at box 2226. This causes cartridge present sensor 2010 to change state and cause a recordation of the system state at box 2225. Another cartridge 34 may be inserted at box 2228. This causes a state change in the cartridge present sensor 2010 and a recordation of the system state at box 2227. If the other cartridge 34 is a new cartridge, indicated at decision block 2230, its insertion may also cause a state change to cartridge condition sensor 2012. In that case, the system state may be recorded at box 2231.

FIG. 53 shows an exemplary memory map 2300 from the memory device 2001 according to various embodiments. The memory map 2300 includes a series of columns 2302, 2304, 2306, 2308, 2310, 2312, 2314, 2316 and rows (not labeled). Column 2302 shows an event number for each of the rows. The other columns represent the output of one sensor of the system 2000. All of the sensor readings recorded at a given time may be recorded in the same row under the same event number. Hence, each row represents an instance where one or more of the signals from the sensors of the system 2000 are recorded.

Column 2304 lists the closure load recorded at each event. This may reflect the output of anvil closure load sensor 2006. Column 2306 lists the firing stroke position. This may be derived from the knife position sensor 2008. For example, the total travel of the knife 32 may be divided into partitions. The number listed in column 2306 may represent the partition where the knife 32 is currently present. The firing load is listed in column 2308. This may be derived from the firing trigger sensor 110. The knife position is listed at column 2310. The knife position may be derived from the knife position sensor 2008 similar to the firing stroke. Whether the anvil 24 is open or closed may be listed at column 2312. This value may be derived from the output of the anvil closure sensor 2004 and/or the anvil closure load sensor 2006. Whether the sled 33 is present, or whether the cartridge 34 is spent, may be indicated at column 2314. This value may be derived from the cartridge condition sensor 2012. Finally, whether the cartridge 34 is present may be indicated a column 2316. This value may be derived from cartridge present sensor 2010. It will be appreciated that various other values may be stored at memory device 2001 including, for example, the end and beginning of firing strokes, for example, as measured by sensors 130, 142.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although the embodiments described above have advantages for an endoscopically employed surgical severing and stapling instrument 100, a similar embodiments may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is believed that the present invention may find use in any procedure where access is limited to a small incision, including but not limited to laparoscopic procedures, as well as open procedures.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

We claim:

1. A surgical instrument comprising:
    an end effector to engage tissue, the end effector comprising a staple channel and an anvil pivotably translatable relative to the staple channel, wherein at least one of the anvil and the staple channel define a longitudinal channel;
    a reciprocating knife positioned to slide distally through the longitudinal channel when the anvil is pivoted to a position substantially parallel to the staple channel;
    a shaft extending proximally from the end effector;
    a handle coupled to a proximal portion of the shaft;
    a trigger coupled to the handle, wherein the trigger is in communication with the end effector to actuate the anvil and the reciprocating knife;
    a first sensor having an output representing a first condition of the trigger;
    a second sensor having an output representing a position of the anvil;
    a third sensor having an output representing a position of the reciprocating knife; and
    an externally accessible memory device in communication with the first, second and third sensors, wherein the memory device is configured to record the output of the first, second and third sensors.

2. The surgical instrument of claim 1, wherein the memory device comprises an output port.

3. The surgical instrument of claim 1, wherein the memory device comprises a removable medium.

4. The surgical instrument of claim 1, wherein the surgical instrument further comprises a second sensor in communication with the memory device, the second sensor having an output representing a second condition of at least one of the group consisting of the trigger and the end effector, wherein the memory device is further configured to record the output of the second sensor.

5. The surgical instrument of claim 4, wherein the memory device is configured to record the output of the first sensor and the output of the second sensor when the first condition changes and when the second condition changes.

6. The surgical instrument of claim 1, wherein the first condition indicates whether an anvil of the end effector is in an open position or a closed position.

7. The surgical instrument of claim 1, wherein the first condition indicates at least one of the group consisting of a position of a knife within the end effector, a position of the trigger, a pressure exerted on the trigger, and a pressure exerted by the end effector.

8. The surgical instrument of claim 1, further comprising a motorized drive system in communication with the trigger and the end effector.

9. The surgical instrument of claim 1, further comprising a mechanical drive system in communication with the trigger and the end effector.

10. The surgical instrument of claim 1, wherein the memory device comprises at least one of the group consisting of a microcontroller and an electrically erasable programmable read only memory (EEPROM).

11. The surgical instrument of claim 1, wherein the first sensor is a binary sensor.

12. The surgical instrument of claim 1, wherein the first sensor is an analog sensor.

13. The surgical instrument of claim 12, wherein the surgical instrument further comprises an analog-to-digital converter in communication with the first sensor and the memory device.

* * * * *

UNITED STATES PATENT AND TRADEMARK OFFICE
CERTIFICATE OF CORRECTION

PATENT NO. : 7,845,537 B2
APPLICATION NO. : 11/343803
DATED : December 7, 2010
INVENTOR(S) : Shelton, IV et al.

It is certified that error appears in the above-identified patent and that said Letters Patent is hereby corrected as shown below:

In the Specification

Column 25, line 32: After "of the staple cartridge" Insert -- 34 contacts the contacts 2011, 2013, a closed circuit is formed. When the circuit is open, the --

Signed and Sealed this
Seventeenth Day of September, 2013

Teresa Stanek Rea
*Deputy Director of the United States Patent and Trademark Office*